United States Patent
Richards-Kortum et al.

[11] Patent Number: 6,095,982
[45] Date of Patent: *Aug. 1, 2000

[54] SPECTROSCOPIC METHOD AND APPARATUS FOR OPTICALLY DETECTING ABNORMAL MAMMALIAN EPITHELIAL TISSUE

[75] Inventors: Rebecca Richards-Kortum; Nirmala Ramanujam; Anita Mahadevan, all of Austin; Michele Follen Mitchell, Houston, all of Tex.

[73] Assignee: Board of Regents, The University of Texas System, Austin, Tex.

[*] Notice: This patent is subject to a terminal disclaimer.

[21] Appl. No.: 08/988,840

[22] Filed: Dec. 11, 1997

Related U.S. Application Data

[63] Continuation of application No. 08/403,446, Mar. 14, 1995, Pat. No. 5,697,373.

[51] Int. Cl.⁷ ................................................. A61B 6/00
[52] U.S. Cl. ............................ 600/476; 600/473; 356/301
[58] Field of Search .................................. 600/407, 310, 600/342, 473, 475, 476, 477, 478; 250/461.2, 459.1; 606/3, 14–16; 356/301, 303, 318; 607/88–93

[56] References Cited

U.S. PATENT DOCUMENTS

| | | | |
|---|---|---|---|
| 4,479,499 | 10/1984 | Alfano et al. . | |
| 4,556,057 | 12/1985 | Hiruma et al. | 128/303.1 |
| 4,648,892 | 3/1987 | Kittrell et al. | 65/4.21 |
| 4,675,529 | 6/1987 | Kushida | 250/458.1 |
| 4,755,684 | 7/1988 | Leiner et al. | 250/461.1 |
| 4,786,813 | 11/1988 | Svanberg et al. | 250/461.1 |
| 4,798,463 | 1/1989 | Koshi . | |
| 4,832,483 | 5/1989 | Verma | 356/39 |
| 4,913,142 | 4/1990 | Kittrell et al. | 606/7 |
| 4,930,516 | 6/1990 | Alfano et al. . | |
| 4,967,745 | 11/1990 | Hayes et al. | 128/303.1 |
| 4,973,848 | 11/1990 | Kolobanov et al. | 250/458.1 |
| 5,003,977 | 4/1991 | Suzuki et al. | 128/633 |
| 5,009,655 | 4/1991 | Daignault, Jr. et al. | 606/7 |

(List continued on next page.)

FOREIGN PATENT DOCUMENTS

| | | |
|---|---|---|
| 0 359 433 | 3/1990 | European Pat. Off. . |
| 0 608 987 A1 | 8/1994 | European Pat. Off. ..... G01N 33/574 |
| 0 650 694 | 5/1995 | European Pat. Off. . |
| 1151436 | 6/1989 | Japan ............................... A61B 5/00 |
| WO 88/05908 | 8/1988 | WIPO ............................ G01N 15/14 |
| WO 90/06718 | 6/1990 | WIPO . |
| WO 90/12536 | 11/1990 | WIPO . |
| WO 92/15008 | 9/1992 | WIPO . |
| WO 93/03672 | 3/1993 | WIPO . |
| WO 94/26168 | 11/1994 | WIPO . |
| WO 95/26673 | 10/1995 | WIPO ............................. A61B 5/00 |

OTHER PUBLICATIONS

K. Schomacker et al., "Ultraviolet Laser–Induced Fluorescence of Colonic Tissue: Basic Biology and Diagnostic Potential," *Lasers in Surgery and Medicine*, 12:63–78, 1992.

(List continued on next page.)

*Primary Examiner*—Marvin M. Lateef
*Assistant Examiner*—Shawna J Shaw
*Attorney, Agent, or Firm*—Fulbright & Jaworski

[57] ABSTRACT

A method and apparatus for detecting tissue abnormality, particularly precancerous cervical tissue, through fluorescence or Raman spectroscopy, or a combination of fluorescence and Raman spectroscopy. In vivo fluorescence measurements were followed by in vitro NIR Raman measurements on human cervical biopsies. Fluorescence spectra collected at 337, 380 and 460 nm excitation were used to develop a diagnostic method to differentiate between normal and dysplastic tissues. Using a fluorescence diagnostic method, a sensitivity and specificity of 80% and 67% were observed for differentiating squamous intraepithelial lesions (SILs) from all other tissues. In accordance with another aspect of the invention, using Raman scattering peaks observed at selected wavenumbers, SILs were separated from other tissues with a sensitivity and specificity of 88% and 100%. In addition, inflammation and metaplasia samples are correctly separated from the SILs.

46 Claims, 25 Drawing Sheets

U.S. PATENT DOCUMENTS

| | | | |
|---|---|---|---|
| 5,014,707 | 5/1991 | Schwarz et al. | 128/633 |
| 5,026,368 | 6/1991 | Adair | 606/15 |
| 5,034,010 | 7/1991 | Kittrell et al. | 606/15 |
| 5,036,853 | 8/1991 | Jeffcoat et al. | 128/634 |
| 5,038,039 | 8/1991 | Wong et al. | 250/339 |
| 5,042,494 | 8/1991 | Alfano et al. | 128/665 |
| 5,046,501 | 9/1991 | Crilly | 128/665 |
| 5,062,431 | 11/1991 | Potter | 128/665 |
| 5,092,331 | 3/1992 | Nakamura et al. | 128/634 |
| 5,104,392 | 4/1992 | Kittrell et al. | 606/15 |
| 5,106,387 | 4/1992 | Kittrell et al. | 606/15 |
| 5,115,137 | 5/1992 | Andersson-Engels et al. | 250/461.2 |
| 5,125,404 | 6/1992 | Kittrell | 128/634 |
| 5,131,398 | 7/1992 | Alfano et al. | 128/665 |
| 5,168,162 | 12/1992 | Oong et al. | 250/339 |
| 5,174,297 | 12/1992 | Dalkuzono | 128/665 |
| 5,192,278 | 3/1993 | Hayes et al. | 606/15 |
| 5,199,431 | 4/1993 | Kittrell et al. | 128/634 |
| 5,201,318 | 4/1993 | Rava et al. | 128/665 |
| 5,251,613 | 10/1993 | Adair | 128/6 |
| 5,261,410 | 11/1993 | Alfano et al. | 128/664 |
| 5,280,788 | 1/1994 | Janes et al. | 128/665 |
| 5,290,275 | 3/1994 | Kittrell et al. | 606/15 |
| 5,293,872 | 3/1994 | Alfano et al. . | |
| 5,303,026 | 4/1994 | Strobl et al. | 356/318 |
| 5,304,173 | 4/1994 | Kittrell et al. | 606/15 |
| 5,318,023 | 6/1994 | Vari et al. | 128/633 |
| 5,318,024 | 6/1994 | Kittrell et al. | 128/634 |
| 5,337,745 | 8/1994 | Benaron . | |
| 5,345,941 | 9/1994 | Rava et al. | 128/665 |
| 5,348,003 | 9/1994 | Caro | 128/633 |
| 5,348,018 | 9/1994 | Alfano et al. | 128/65 |
| 5,369,496 | 11/1994 | Alfano et al. . | |
| 5,377,676 | 1/1995 | Vari et al. . | |
| 5,386,827 | 2/1995 | Chance et al. . | |
| 5,408,996 | 4/1995 | Salb | 128/633 |
| 5,413,108 | 5/1995 | Alfano . | |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,421,346 | 6/1995 | Sanyal | 128/750 |
| 5,450,857 | 9/1995 | Garfield et al. | 128/778 |
| 5,452,723 | 9/1995 | Wu et al. | 128/664 |
| 5,467,767 | 11/1995 | Alfano et al. | 128/665 |
| 5,498,875 | 3/1996 | Obremski et al. . | |
| 5,590,660 | 1/1997 | MacAulay et al. . | |
| 5,596,992 | 1/1997 | Haaland et al. . | |

OTHER PUBLICATIONS

R. Cothren et al., "Gastrointestinal Tissue Diagnosis by Laser–Induced Fluorescence Spectroscopy at Endoscopy," *Gastrointestinal Endoscopy*, 36:105–111, 1990.

S. Andersson–Engels et al., "Fluorescence Imaging and Points Measurements of Tissue: Appliations to the Demarcation of Malignant Tumors and Atherosclerotic Lesions from Normal Tissue," *Photochemistry and Photobiology*, 53:807–814, 1991.

R. Rava et al., "Early Detection of Dysplasia in Colon and Bladder Tissue Using Laser–Induced Fluorescence," *SPIE, Optical Methods for Tumor Treatment and Early Diagnosis: Mechanisms and Techniques*, 1426:68–78, 1991.

R. Cothren et al., "Argon Ion Laser–Induced Tissue Fluorescence: Clinical Spectroscopic Studies," *SPIE, Optical Fibers in Medicine III*, vol. 906, Abstract only, 1988.

S. Lam et al., "Detection of Dysplasia and Carcinoma In Situ by Ratio Fluorometry," *Am. Rev. Respir. Dis.*, 146:1458–1461, 1992.

R.R. Alfano et al., "Optical Spectroscopic Diagnosis of Cancer in Normal Breast Tissues," *J. Opt. Soc. Am. B.*, 6:1015–1023, May 1989.

R.R. Alfano et al., "Fluorescence Spectra from Cancerous and Normal Human Breast and Lung Tissues," *IEEE Journal of Quantum Electronics*, QE–23:1806–1811, Oct. 1987.

J. Hung et al., "Autofluorescenceof Normal and Malignant Bronchial Tissue," *Lasers in Surgery and Medicine*, 11:99–105, 1991.

R. Richards–Kortum et al., "Spectroscopic Diagnosis of Colonic Dysplasia," *Photochemistry and Photobiology*, 53:777–786, 1991.

C. Kapadia et al., "Laser–Induced Spectroscopy of Human Colonic Mucosa: Detection of Adenomatous Transformation," *Gastroenterology*, 99:150–157, 1990.

P. Wong et al., "Infrared Spectroscopy of Exfoliated Human Cervical Cells: Evidence of Extensive Structural Changes During Carcinogensis," *Proc. Natl. Acad. Sci. USA*, 88:10988–10992, 1991.

W. Glassman, "Ultraviolet Excited Fluorescent Spectra from Non–Malignant and Malignant Tissues of the Gynecological Tract," *Lasers in the Lifesciences*, 49–58, 1992.

W. Lohmann et al., "Native Fluorescence of the Cervix Uteri as a Marker for Dysplasia and Invasive Carcinoma," *European Journal of Obstetrics & Gynecology and Reproductive Biology*, 31:249–253, 1989.

N. Ramanujam et al., "Diagnosis of Cervical Intraepithelial Neoplasia Using Laser–Induced Fluorescence," *Poster Presentation at Future Directions of Lasers in Surgery and Medicine III*, 1993.

R. Walpole and R. Myers, *Tests of Hypotheses, In: Probability and Statistics for Engineers and Scientists, 2nd Ed.*, Chapter 7:v, 238–259, 1978.

W. Dillon and M. Goldstein, *Principal Components Analysis, In: Multivariate Analysis, Methods and Applications*, Chapter 2:23–392, 1984.

C. Liu et al., "Raman, Fluorescence, and Time–Resolved Light Scattering as Optical Diagnostic Techniques to Separate Diseased and Normal Biomedical Media," *J. Photochem. Photobiol. B: Biol.*, 16:187–209, 1992.

D. Redd et al., "Raman Spectroscopic Characterization of Human Breast Tissues: Implications for Breast Cancer Diagnosis," *Applied Spectroscopy*, 47(6):787–791, 1993.

R. Alfano et al., "Human Breast Tissues Studied by IR Fourier Transform Raman Spectroscopy," *Lasers in the Life Sciences*, 4(1):23–28, 1991.

G. Small et al., "Strategies for Coupling Digital Filtering with Partial Least–Squares Regression: Application to the Determinationof Glucose in Plasma by Fourier Transform Near–Infrared Spectroscopy," *Anal. Chem.*, 65:3279–3289, 1993.

International Search Report dated Jul. 17, 1996 (TUUT:003P).

International Search Report dated Jul. 12, 1996 (TUUT:004P).

International Search Report dated Jul. 12, 1996 (TUUT:005P).

Alfano et al., "Laser Induced Fluorescence Spectroscopy from Native Cancerous and Normal Tissue," *IEEE Journal of Quantum Electronics*, QE–20(12):1507–1511, 1984.

Avrillier et al., "XeCl Excimer Laser–Induced Autofluorescence Spectroscopy for Human Cerebral Tumours Diagnosis: Preliminary Study," *SPIE*, 1894:177–186, 1993.

Bergeron et al., "Complete Fluorescence Spectrum of a Normal and Atherosclerotic Aorta," *Can. J. Phys.*, 66:1035–1039, 1988.

Bosshart et al., "Fluorescence Spectroscopy for Identification of Atherosclerotic Tissue," *Cardiovascular Research*, 26:620–625, 1992.

Bottiroli et al., "Natural Fluorescence of Normal and Neoplastic Human Colon: A Comprehensive "ex vivo" Study," *Lasers in Surgery & Medicine*, 16(1):48–60, 1995.

Clarke et al., "Spectroscopic Characterization of Cardiovascular Tissue," *Lasers in Surgery and Medicine*, 8:45–49, 1988.

Deckelbaum et al., "Discrimination of Normal and Atherosclerotic Aorta by Laser–Induced Fluorescence," *Lasers in Surgery and Medicine*, 7:330–335, 1987.

Deckelbaum et al., "In–vivo Fluorescence Spectroscopy of Normal and Atherosclerotic Arteries," *SPIE*, 906:314–319, 1988.

D'Hallewin et al., "In Vivo Fluorescence Detection of Human Bladder Carcinoma Without Sensitizing Agents," *Journal of the American Paraplegia Society*, 17(4):161–164, 1994.

Edholm et al., "Tissue Identification During Needle Puncture by Reflection Spectrophotometry," *Biol. Engng.*, 6:409–413, 1968.

Fiarman et al., "Differences in Laser–Induced Autofluorescence between Adenomatous and Hyperplastic Polyps and Normal Confocal Mucosa by Confocal Microscopy," *Digestive Disease & Sciences*, 40(6):11261–1268, 1995.

Fitzmaurice et al., "Argon Ion Laser–Excited Autofluorescence in Normal and Atherosclerotic Aorta and Coronary Arteries: Morphologic Studies," *American Heart Journal*, 118(5)(1):1028–1037, 1989.

Frank et al., "Characterization of Human Breast Biopsy Specimens with Near–IR Raman Spectroscopy," *Anal. Chem.*, 66:319–326, 1994.

Ghadially and Neish, "Porphyrin Fluorescence of Experimentally Produced Squamous Cell Carcinoma," *Nature*, 188:1124, 1960.

Ghadially et al., "Mechanisms Involved in the Production of Red Fluorescence of Human and Experimental Tumours," *Path. Bact.*, 85:77–92, 1963.

Glassman et al., "Excitation Spectroscopy of Malignant and Non–malignant Gynecological Tissues," *Lasers in the Life Sciences*, 6(2):99–106, 1994.

Glassman et al., "Time Resolved and Steady State Fluorescence Spectroscopy from Normal and Malignant Cultured Human Breast Cell Lines," *Lasers in the Life Sciences*, 6(2):91–98, 1994.

Gmitro et al., "Measurement Depth of Laser–Induced Tissue Fluorescence with Application to Laser Angioplasty," *Applied Optics*, 27(9):1844–1849, 1988.

Harries et al., "Diagnostic Imaging of the Larynx: Autofluorescence of Laryngeal Tumours Using the Helium–Cadmium Laser," *The Journal of Laryngology and Otology*, 109:108–110, 1995.

Hoyt et al., "Remote Biomedical Spectroscopic Imaging of Human Artery Wall," *Lasers in Surgery and Medicine*, 8:1–9, 1988.

Kittrell et al., "Diagnosis of Fibrous Arterial Atherosclerosis Using Fluorescence," *Applied Optics*, 24(15):2280–2281, 1985.

Kluftinger et al., "Detection of Squamous Cell Cancer and Pre–cancerous Lesions by Imaging of Tissue Autofluorescence in the Hamster Cheek Pouch Model," *Surgical Oncology*, 1:183–188, 1992.

Laifer et al., "Biochemical Basis for the Difference Between Normal and Atherosclerotic Arterial Fluorescence," *Circulation*, 80(6):1893–1901, 1989.

Lam et al., "Detection of Dysplasia and Carcinoma is situ with a Lung Imaging Fluorescence Endoscope Device," *J. Thorac Cardiovasc. Surg.*, 105:1035–1040, 1993.

Leon et al., "Human Arterial Surface Fluorescence: Atherosclerotic Plaque Identification and Effects of Laser Atheroma Ablation," *JACC*, 12(1):94–102, 1988.

Lohmann et al., "In situ Differentiation Between Nevi and Malignant Melanomas by Fluorescence Measurements," *Naturwissenschaften*, 78:456–457, 1991.

Lohmann et al., "Fluorescence Studies on Lung Tumors," *Z. Naturforsch*, 45c:1063–1066, 1990.

Lohmann and Künzel, "Fluorescence Tomographical Studies on Breast Tissue with Cancer," *Naturwissenschaften*, 77:476–478, 1990.

Lohman, W., "Native Fluorescence of Unstained Cryo–sections of the Skin with Melanomas and Nevi," *Naturwissenschaften*, 76:424–426, 1989.

Mahadevan et al., "Optical Techniques for the Diagnosis of Cervical Precancers: A Comparison of Raman and Fluorescence Spectroscopies," *SPIE*, 2388:110–120, 1995.

Mahadevan et al., "Study of the Fluorescence Properties of Normal and Neoplastic Human Cervical Tissue," *Lasers in Surgery and Medicine*, 13:647–655, 1993.

Manoharan et al., "Ultraviolet Resonance Raman Spectroscopy for Detection of Colon Cancer," *Lasers in Life Sciences*, 6:217–227, 1995.

Manoharan et al., "Laser–induced Fluorescence Spectroscopy of Colonic Dysplasia: Prospects for Optical Histological Analysis," *SPIE*, 2388:417–421, 1995.

Montán and Strömblad, "Spectral Characterization of Brain Tumors Utilizing Laser–Induced Fluorescence," *Lasers in Life Sciences*, 1(4):275–285, 1987.

Mosier–Boss et al., "Fluorescence Rejection in Raman Spectroscopy by Shifted–Spectra, Edge Detection, and FFT Filtering Techniques," *Applied Spectroscopy*, 49(5):630–638, 1995.

Nishioka, "Laser–Induced Fluorescence Spectroscopy," *Experimental and Investigational Endoscopy*, 4(2):313–326, 1994.

Oraevsky et al., "XcCl Laser–Induced Fluorescence of Atherosclerotic Arteries. Spectral Similarities Between Lipid–Rich Lesions and Peroxidized Lipoproteins," *Circulation Research*, 72:;84–90, 1993.

Ozaki et al., "Biomedical Application of Near–Infrared Fourier Transform Raman Spectroscopy, Part I: The 1064–nm Excited Raman Spectra of Blood and Met Hemoglobin," *Applied Spectroscopy*, 46(3):533–536, 1992.

Palcic et al., "Detection and Localization of Early Lung Cancer by Imaging Techniques," *Chest*, 99:742–743, 1991.

Papazoglou et al., "Laser–Induced Fluorescence Detection of Cardiovascular Atherosclerotic Deposits via Their Natural Emission and Hypocrellin (HA) Probing," *J. Photochem. Photobiol. B: Biol.*, 22:139–144, 1994.

Ramanujam et al., "In vivo Diagnosis of Cervical Intraepithelial Neoplasia Using 337–nm–Excited Laser–Induced Fluorescence," *Proc. Natl. Acad. Sci. USA*, 91:10193–10197, 1994.

Ramanujam et al., "Fluorescence Spectroscopy: A Diagnostic Tool for Cervical Intraepithelial Neoplasia (CIN)," *Gynecologic Oncology*, 52:31–38, 1994.

Richards–Kortum et al., "476 nm Excited Laser–Induced Fluorescence Spectroscopy of Human Coronary Arteries: Applications in Cardiology," *American Heart Journal*, 122(4)(1):1141–1150, 1991.

Richards–Kortum et al., "Spectral Diagnosis of Atherosclerosis Using an Optical Fiber Laser Catheter," *American Heart Journal*, 118(2):381–391, 1989.

Richards–Kortum et al., "A One–Layer Model of Laser–Induced Fluorescence for Diagnosis of Disease in Human Tissue: Applications to Atherosclerosis," *IEEE Transactions on Biomedical Engineering*, 36(12):1222–1232, 1989.

Richards–Kortum et al., "Survey of the Uvand Visible Spectroscopic Properties of Normal and Atherosclerotic Human Artery Using Fluorescence EEMS," in *Optronic Techniques in Diagnostic and Therapeutic Medicine*, ed. R. Pratesi, Plenum, 1991, pp. 129–138.

Richards–Kortum et al., "A Model for Extraction of Diagnostic Information from Laser Induced Fluorescence Spectra of Human Artery Wall," *Spectrochimica Acta*, 45A(1):87–93, 1989.

Römer et al., "Laser–Induced Fluorescence Microscopy of Normal Colon and Dysplasia in Colonic Adenomas: Implications for Spectroscopic Diagnosis," *The American Journal of Gastroenterology*, 90(1):81–87, 1995.

Sartori et al., Autofluorescence Maps of Atherosclerotic Human Arteries–A New Technique in Medical Imaging, *IEEE Journal of Quantum Electronics*, QE–23(10):1794–1797, 1987.

Schomacker et al., "Ultraviolet Laser–Induced Fluorescence of Colonic Polyps," *Gastroenterology*, 102:1155–1160, 1992.

Sterenborg et al., "In vivo Fluorescence Spectroscopy and Imaging of Human Skin Tumours," *Lasers in Medical Science*, 9:191–201, 1994.

van Gemert et al., "Optical Properties of Human Blood Vessel Wall and Plaque," *Lasers in Surgery and Medicine*, 5:235–237, 1985.

Verbunt et al., "Characterization of Ultraviolet Laser–Induced Autofluorescence of Ceroid Deposits and Other Structures in Atherosclerotic Plaques as a Potential Diagnostic for Laser Angiosurgery," *American Heart Journal*, 123(1):208–216, 1992.

Yuanlong et al., "Characteristic Autofluorescence for Cancer Diagnosis and Its Origin," *Lasers in Surgery and Medicine*, 7:528–532, 1987.

Zeng et al., "Autofluorescence Distribution in Skin Tissue Revealed by Micropectrophotometer Measurements," *SPIE*, 1876:129–135, 1993.

Zeng et al., "A Computerized Autofluorescence and Diffuse Reflective Spectroanalyser System for in vivo Studies," *Phys. Med. Biol.*, 38:231–240, 1993.

Baraga et al., "In situ Optical Histochemistry of Human Artery Using Near Infrared Fourier Transform Raman Spectroscopy," *Proc. Natl. Acad. Sci.*, 89:3473–3477, 1992.

Bot et al, "Raman Microspectroscopy of Fixed Rabbit and Human Lenses and Lens Slices: New Potentials," *Exp. Eye Res.*, 49:161–169, 1989.

Clarke et al., "Laser Raman Spectroscopy of Calcified Atherosclerotic Lesions in Cardiovascular Tissue," *Applied Optics*, 26(16):3175–3177, 1987.

Feld et al., "Detection and Characterization of Human Tissue Lesions with Near Infrared Raman Spectroscopy," *SPIE*, 2388:99–104, 1995.

Frank et al., "Raman Spectroscopy of Normal and Diseased Human Breast Tissues," *Analytical Chemistry*, 67(5):777–783, 1995.

Frank et al., "Characterization of Human Breast Biopsy Specimens with Near–IR Raman Spectroscopy," *Analytical Chemistry*, 66(3)19–326, 1994.

Funfschilling and Williams, "CW Laser Wavelength Modulation in Raman and Site Selection Fluorescence Spectroscopy," *Applied Spectroscopy*, 30(4):443–446, 1976.

Kramer et al., "Spectral Diagnosis of Human Coronary Artery: A Clinical System for Real Time Analysis," *SPIE*, 2395:376–382, 1995.

Lewis et al., "Raman Spectrometry and Neural Networks for the Classification of Wood Types—1," *Spectrochimica Acta*, 50A(11):1943–1958, 1994.

Liu et al., "Near–IR Fourier Transform Raman Spectroscopy of Norman and Atherosclerotic Human Aorta," *Lasers in the Life Sciences*, 4(3):257–264, 1992.

Liu et al., Raman, Fluorescence, and Time–Resolved Light Scattering as Optical "Diagnostic Techniques to Separate Diseased and Normal Biomedical Media," *Journal of Photochemistry & Photobiology*, 16(2):187–209, 1992. Abstract only.

Mahadevan et al, "Optical Techniques for the Diagnosis of Cervical Precancers: A Comparison of Raman and Fluorescence Spectroscopies," *SPIE*, 2388:110–120, 1995.

Manoharan et al., "Ultraviolet Resonance Raman Spectroscopy for Detection of Colon Cancer," *Lasers in the Life Sciences*, 6(4):217–227, 1995.

Manoharan et al., "Raman Spectroscopy for Cancer Detection: Instrument Development and Tissue Diagnosis," *SPIE*, 2328, 128–132, 1994.

Mosier–Boss et al., "Fluorescence Rejection in Raman Spectroscopy by Sifted–Spectra, Edge Detection, and FFT Filtering Techniques," *Applied Spectroscopy*, 49(5):630–638, 1995.

Myrick et al., "Comparison of Some Fiber Optic Configurations for Measurement of Luminescence and Raman Scattering," *Applied Optics*, s29(9):1333–1344, 1990.

Myric and Angel "Elimination of Background in Fiber–Optic Raman Measurements," *Applied Spectroscopy*, 44(4):565–570, 1990.

Nie et al., "Applications of Near–Infrared Fourier Transform Raman Spectroscopy in Biology and Medicine," *Spectroscopy*, 5(7):24–32, 1990.

Ozaki, "Medical Application of Raman Spectroscopy," *Applied Spectroscopy Reviews*, 24(3 & 4):259–312, 1988.

Puppels et al., "Laser Irradiation and Raman Spectroscopy of Single Living Cells and Chromosomes: Sample Degradation Occurs With 514.5 nm but Not With 660 nm Laser Light," *Experimental Cell Research*, 195(2):361–367, 1991.

Puppels et al., "Raman Microspecroscopic Approach to the Study of Human Granulocytes," *Biophys. J.*, 60:1046–1056, 1991.

Brennan et al., "In situ Histochemical Analysis of Human Coronary Arteries by Raman Spectroscopy Compared with Biochemical Assay," In *Advances in Fluorescence Sensing Technology*, vol. II., ed. J.R. Lakowicz, *SPIE Proceedings*, 2388:105–109, 1995.

Schrader et al., "NIR FT Raman Spectroscopy in Medical Diagnosis," *Journal of Molecular Structure*, 348:293–296, 1995.

Schwab and McCreery, "Versatile, Efficient Raman Sampling with Fiber Optics," *Anal. Chem.*, 56:2199–2204, 1984.

Shreve et al., "Effective Rejection of Fluorescence Interference in Raman Spectroscopy Using a Shifted Excitation Difference Technique," *Applied Spectroscopy*, 46(4):707–711, 1992.

Williams and Barry, "Comparison of Fourier Transform Raman Spectra of Mammalian and Reptilian Skin," *Analyst*, 119:563–566, 1994.

Williams et al., "A Critical Comparison of Some Raman Spectroscopic Techniques for Studies of Human Stratum Corneum," *Pharmaceutical Research*, 10(11):1642–1647, 1993.

Yu et al., "Disulfide Bond Formation in the Eye Lens," *Proc. Natl. Acad. Sci. USA*, 82:7965–7968, 1985.

Angel et al., "Computer–Controlled Instrument for the Recovery of a Resonance Raman Spectrum in the Presence of Strong Luminescence," *Anal. Chem.*, 56, 3000–3001, 1984.

Keller et al., "Application of Near–Infrared–Fourier Transform Raman Spectroscopy in Medical Research," *J. Raman Spectrosc.* 25(7–8):663–671, 1994.

Mizumo et al., "Near–Infrared Fourier Transform Raman Spectroscopic Study of Human Brain Tissues and Tumours," *J. Raman Spectrosc.*, 25:25–29, 1994.

Van Duyne et al., "Mode–Locked Laser Raman Spectroscopy–A New Technique for the Rejection of Interfering Background Luminescence Signals," *Anal. Chem.*, 46, 213–222, 1974.

Yu et al., "Laser Raman Spectroscopy of the Lens In–Situ Measured in an Anesthesized Rabbit," *Curr. Eye Res.*, 1(10):615–618, 1982. Abstract only.

SPECTROSCOPIC METHOD AND APPARATUS FOR OPTICALLY DETECTING ABNORMAL MAMMALIAN EPITHELIAL TISSUE

This is a continuation of application Ser. No. 08/403,446, filed Mar. 14, 1995, now U.S. Pat. No. 5,697,373.

BACKGROUND OF THE INVENTION

The invention relates to optical methods and apparatus used for the diagnosis of cervical precancers.

Cervical cancer is the second most common malignancy in women worldwide, exceeded only by breast cancer and in the United States, it is the third most common neoplasm of the female genital tract. 15,000 new cases of invasive cervical cancer and 55,000 cases of carcinoma in situ (CIS) were reported in the U.S. in 1994. In 1994, an estimated 4,600 deaths occurred in the United States alone from cervical cancer. However, in recent years, the incidence of pre-invasive squamous carcinoma of the cervix has risen dramatically, especially among young women. 1S Women under the age of 35 years account for up to 24.5% of patients with invasive cervical cancer, and the incidence is continuing to increase for women in this age group. It has been estimated that the mortality of cervical cancer may rise by 20% in the next decade unless further improvements are made in detection techniques.

The mortality associated with cervical cancer can be reduced if this disease is detected at the early stages of development or at the pre-cancerous state (cervical intraepithelial neoplasia (CIN)). A Pap smear is used to screen for CIN and cervical cancer in the general female population. This technique has a false-negative error rate of 15–40%. An abnormal pap smear is followed by colposcopic examination, biopsy and histologic confirmation of the clinical diagnosis. Colposcopy requires extensive training and its accuracy for diagnosis is variable and limited even in expert hands. A diagnostic method that could improve the performance of colposcopy in the hands of less experienced practitioners, eliminate the need for multiple biopsies and allow more effective wide scale diagnosis could potentially reduce the mortality associated with cervical cancer.

Recently, fluorescence, infrared absorption and Raman spectroscopies have been proposed for cancer and precancer diagnosis. Many groups have successfully demonstrated their use in various organ systems. Auto and dye induced fluorescence have shown promise in recognizing atherosclerosis and various types of cancers and precancers. Many groups have demonstrated that autofluorescence may be used for differentiation of normal and abnormal tissues in the human breast and lung, bronchus and gastrointestinal tract. Fluorescence spectroscopic techniques have also been investigated for improved detection of cervical dysplasia.

An automated diagnostic method with improved diagnostic capability could allow faster, more effective patient management and potentially further reduce mortality.

SUMMARY OF THE INVENTION

The present invention demonstrates that fluorescence and Raman spectroscopy are promising techniques for the clinical diagnosis of cervical precancer.

Studies were conducted in vitro to establish a strategy for clinical in vivo diagnosis, and indicated that 337, 380 and 460 nm (±10 nm) are optimal excitation wavelengths for the identification of cervical precancer. In vivo fluorescence spectra collected at 337 nm from 92 patients were used to develop spectroscopic methods to differentiate normal from abnormal tissues. Using empirical parameters such as peak intensity and slope of the spectra, abnormal and normal tissues were differentiated with a sensitivity and specificity of 85% and 75%. Using multivariate statistical methods at 337 nm excitation, normal and squamous intraepithelial lesions (SILs—lesions with dysplasia and human papilloma virus (HPV)) were differentiated with a sensitivity of 91% and specificity of 82%. At 380 nm excitation, can be differentiated from columnar normal tissues and from tissues with inflammation with a sensitivity of 77% and a specificity of 72%. At 460 nm excitation, high grade SILs (moderate to severe dysplasia carcinoma) and low grade SILs (mild dysplasia, HPV) were differentiated with a sensitivity and specificity of 73% and 85%. As used herein the calculations of sensitivity and specificity are presented in detail in Appendix I.

The present invention also contemplates the use of Raman spectroscopy for the diagnosis of disease in tissue. Raman scattering signals are weak compared to fluorescence. However, Raman spectroscopy provides molecular specific information and can be applied towards tissue diagnosis. The present invention exploits the capabilities of near infrared (NIR) Raman spectroscopy and fluorescence spectroscopy to differentiate normal, metaplastic and inflammatory tissues from SILs. Further, the ability of these techniques to separate high grade dysplastic lesions from low grade lesions is also exploited.

The invention also contemplates the use of fluorescence spectroscopy in combination with Raman spectroscopy for the diagnosis of disease in tissue.

More particularly, the present invention contemplates methods and apparatus for the optical diagnosis of cervical precancers. Specifically, one embodiment of the method of the present invention detects tissue abnormality in a tissue sample by illuminating a tissue sample with a first electromagnetic radiation wavelength selected to cause the tissue sample to produce a fluorescence intensity spectrum indicative of tissue abnormality. Then, a first fluorescence intensity spectrum emitted from the tissue sample as a result of illumination with the first wavelength is detected. The tissue sample is then illuminated with a second electromagnetic radiation wavelength selected to cause the tissue sample to produce a fluorescence intensity spectrum indicative of tissue abnormality, and a second fluorescence intensity spectrum emitted from the tissue sample as a result of illumination with the second wavelength is detected. Finally, a probability that the tissue sample is normal or abnormal is calculated from the first fluorescence intensity spectrum, and a degree of abnormality of the cervical tissue sample is calculated from the second fluorescence intensity spectrum.

The invention further contemplates that each of the calculations include principal component analysis of the first and second spectra, relative to a plurality of preprocessed spectra obtained from tissue samples of known diagnosis. The invention also contemplates normalizing the first and second spectra, relative to a maximum intensity within the spectra, and mean-scaling the first and second spectra as a function of a mean intensity of the first and second spectra.

Another embodiment of the invention includes detecting tissue abnormality in a diagnostic tissue sample by illuminating the tissue sample with an illumination wavelength of electromagnetic radiation selected to cause the tissue sample to emit a Raman spectrum comprising a plurality of wavelengths shifted from the illumination wavelength. A plurality of peak intensities of the Raman spectrum at wavelength shifts selected for their ability to distinguish normal tissue from abnormal tissue are detected, and each of the plurality of detected peak intensities at the wavelength shifts are compared with intensities of a Raman spectrum from known normal tissue at corresponding wavelength shifts. Abnormality of the tissue sample is assessed as a function of the comparison. This embodiment also contemplates calculating a ratio between selected intensities of the Raman spectrum, and detecting abnormality of the tissue sample as a function of the ratio.

The invention also contemplates calculating a second ratio between another two of the plurality of peak intensities, and detecting a degree of tissue abnormality as a function of the second ratio.

In yet another embodiment of the method of the present invention, calculation of one or more ratios between Raman spectrum intensities is used alone to detect tissue abnormality without comparing individual intensities with those of known normal tissue.

The present invention also contemplates the combination of Raman and fluorescence spectroscopy to detect tissue abnormality.

The apparatus of the present invention includes a controllable illumination device for emitting a plurality of electromagnetic radiation wavelengths selected to cause a tissue sample to produce a fluorescence intensity spectrum indicative of tissue abnormality, an optical system for applying the plurality of radiation wavelengths to a tissue sample, a fluorescence intensity spectrum detecting device for detecting an intensity of fluorescence spectra emitted by the sample as a result of illumination by the plurality of electromagnetic radiation wavelengths, a data processor, connected to the detecting device, for analyzing detected fluorescence spectra to calculate a probability that the sample is abnormal.

A Raman spectroscopy apparatus in accordance with the present invention includes an illumination device for generating at least one illumination wavelength of electromagnetic radiation selected to cause a tissue sample to emit a Raman spectrum comprising a plurality of wavelengths shifted from the illumination wavelength, a Raman spectrum detector for detecting a plurality of peak intensities of the Raman spectrum at selected wavelength shifts, and a programmed computer connected to the Raman spectrum detector, programmed to compare each of the plurality of detected peak intensities with corresponding peak intensities of a Raman spectrum from known normal tissue, to detect tissue abnormality.

These and other features and advantages of the present invention will become apparent to those of ordinary skill in this art with reference to the appended drawings and following detailed description.

DETAILED DESCRIPTION

I. Introduction

To illustrate the advantages of the present invention fluorescence spectra were collected in vivo at colposcopy from 20 patients. Fluorescence spectra were measured from three to four colposcopically normal and three to four colposcopically abnormal sites as identified by the practitioner using techniques known in the art. Specifically, in cervical tissue, nonacetowhite epithelium is considered normal, whereas acetowhite epithelium and the presence of vascular atypias (such as punctuation, mosaicism, and atypical vessels) are considered abnormal. One normal and abnormal site from those investigated were biopsied from each patient. These biopsies were snap frozen in liquid nitrogen and stored in an ultra low temperature freezer at −85° C. until Raman measurements were made.

II. Diagnostic Apparatus

1. Fluorescence Spectroscopy Diagnostic Apparatus

Fluorescence spectra were recorded with a spectroscopic system incorporating a pulsed nitrogen pumped dye laser, an optical fiber probe and an optical multi-channel analyzer at colposcopy. The laser characteristics for the study were: 337, 380 and 460 nm wavelengths, transmitted pulse energy of 50 uJ, a pulse duration of 5 ns and a repetition rate of 30 Hz. The probe includes 2 excitation fibers, one for each wavelength and 5 collection fibers. Rhodamine 6G (8 mg/ml) was used as a standard to calibrate for day to day variations in the detector throughput. The spectra were background subtracted and normalized to the peak intensity of rhodamine. The spectra were also calibrated for the wavelength dependence of the system.

Figure 1:
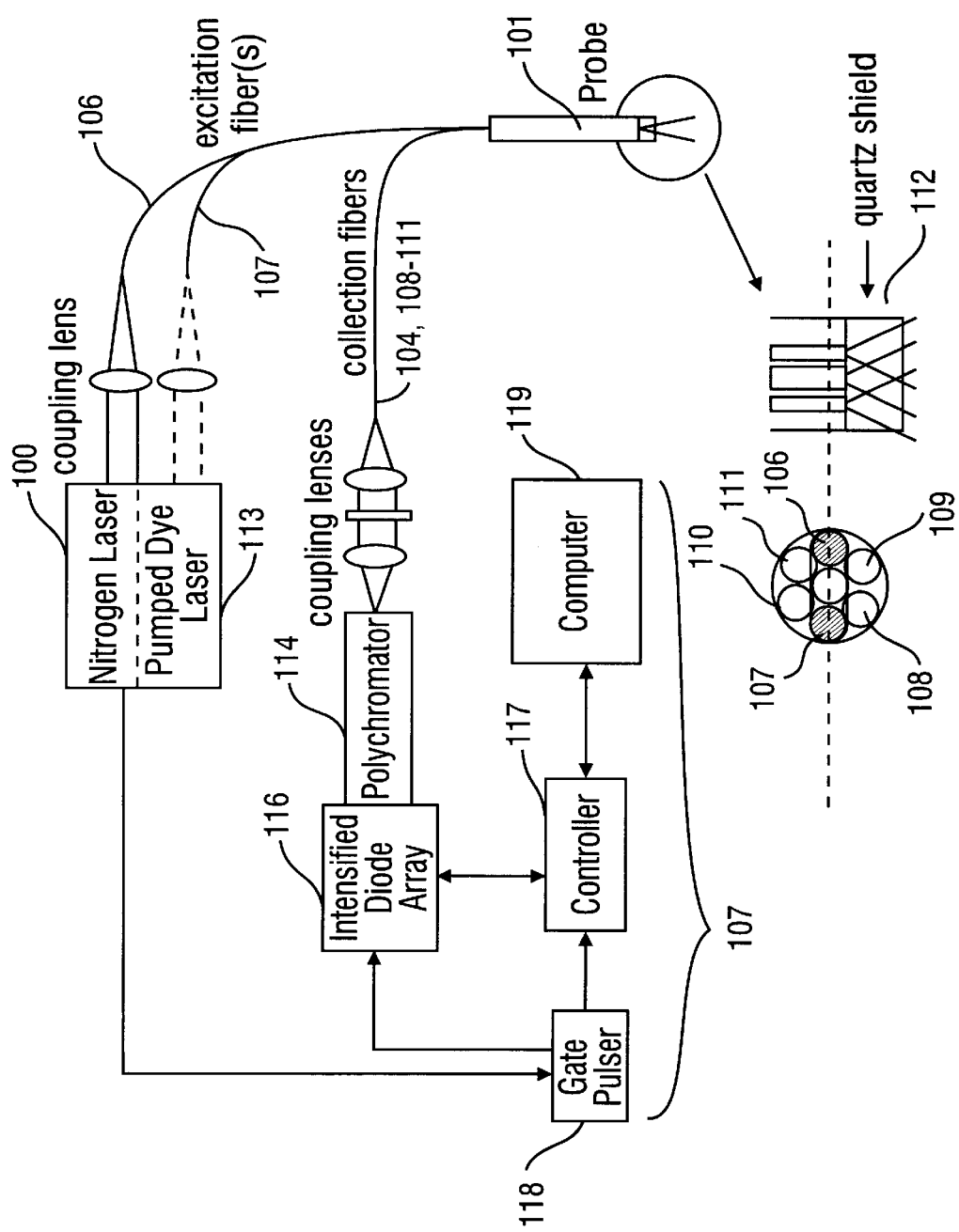
FIG. 1 is a block diagram of an exemplary fluorescence spectroscopy diagnostic apparatus, in accordance with the present invention.

FIG. 1 is an exemplary spectroscopic system for collecting and analyzing fluorescence spectra from cervical tissue, in accordance with the present invention, incorporating a pulsed nitrogen pumped dye laser 100, an optical fiber probe 101 and an optical multi-channel analyzer 103 utilized to record fluorescence spectra from the intact cervix at colposcopy. The probe 101 comprises a central fiber 104 surrounded by a circular array of six fibers. All seven fibers have the same characteristics (0.22 NA, 200 micron core diameter). Two of the peripheral fibers, 106 and 107, deliver excitation light to the tissue surface; fiber 106 delivers excitation light from the nitrogen laser and fiber 107 delivers light from the dye module (overlap of the illumination area viewed by both optical fibers 106, 107 is greater than 85%). The purpose of the remaining five fibers (104 and 108–111) is to collect the emitted fluorescence from the tissue surface directly illuminated by each excitation fibers 106, 107. A quartz shield 112 is placed at the tip of the probe 101 to provide a substantially fixed distance between the fibers and the tissue surface, so fluorescence intensity can be reported in calibrated units.

Excitation light at 337 nm excitation was focused into the proximal end of excitation fiber 106 to produce a 1 mm diameter spot at the outer face of the shield 112. Excitation light from the dye module 113, coupled into excitation fiber 107 was produced by using appropriate fluorescence dyes; in this example, BBQ (1E-03M in 7 parts toluene and 3 parts ethanol) was used to generate light at 380 nm excitation, and Coumarin 460 (1E-02 M in ethanol) was used to generate light at 460 nm excitation. The average transmitted pulse energy at 337, 380 and 460 nm excitation were 20, 12 and 25 mJ, respectively. The laser characteristics for this embodiment are: a 5 ns pulse duration and a repetition rate of 30 Hz, however other characteristics would also be acceptable. Excitation fluences should remain low enough so that cervical tissue is not vaporized and so that significant photo-bleaching does not occur. In arterial tissue, for example, significant photo-bleaching occurs above excitation fluences of 80 mJ/mm.

The proximal ends of the collection fibers 104, 108–111 are arranged in a circular array and imaged at the entrance slit of a polychromator 114 (Jarrell Ash, Monospec 18) coupled to an intensified 1024-diode array 116 controlled by a multi-channel analyzer 117 (Princeton Instruments, OMA). 370, 400 and 470 nm long pass filters were used to block scattered excitation light at 337, 380 and 460 nm excitation respectively. A 205 ns collection gate, synchronized to the leading edge of the laser pulse using a pulser 118 (Princeton Instruments, PG200), effectively eliminated the effects of the colposcope's white light illumination during fluorescence measurements. Data acquisition and analysis were controlled by computer 119 in accordance with the fluorescence diagnostic method described below in more detail with reference to the flowcharts of FIGS. 3A–3C.

2. Raman Spectroscopy Diagnostic Apparatus

Figure 2:
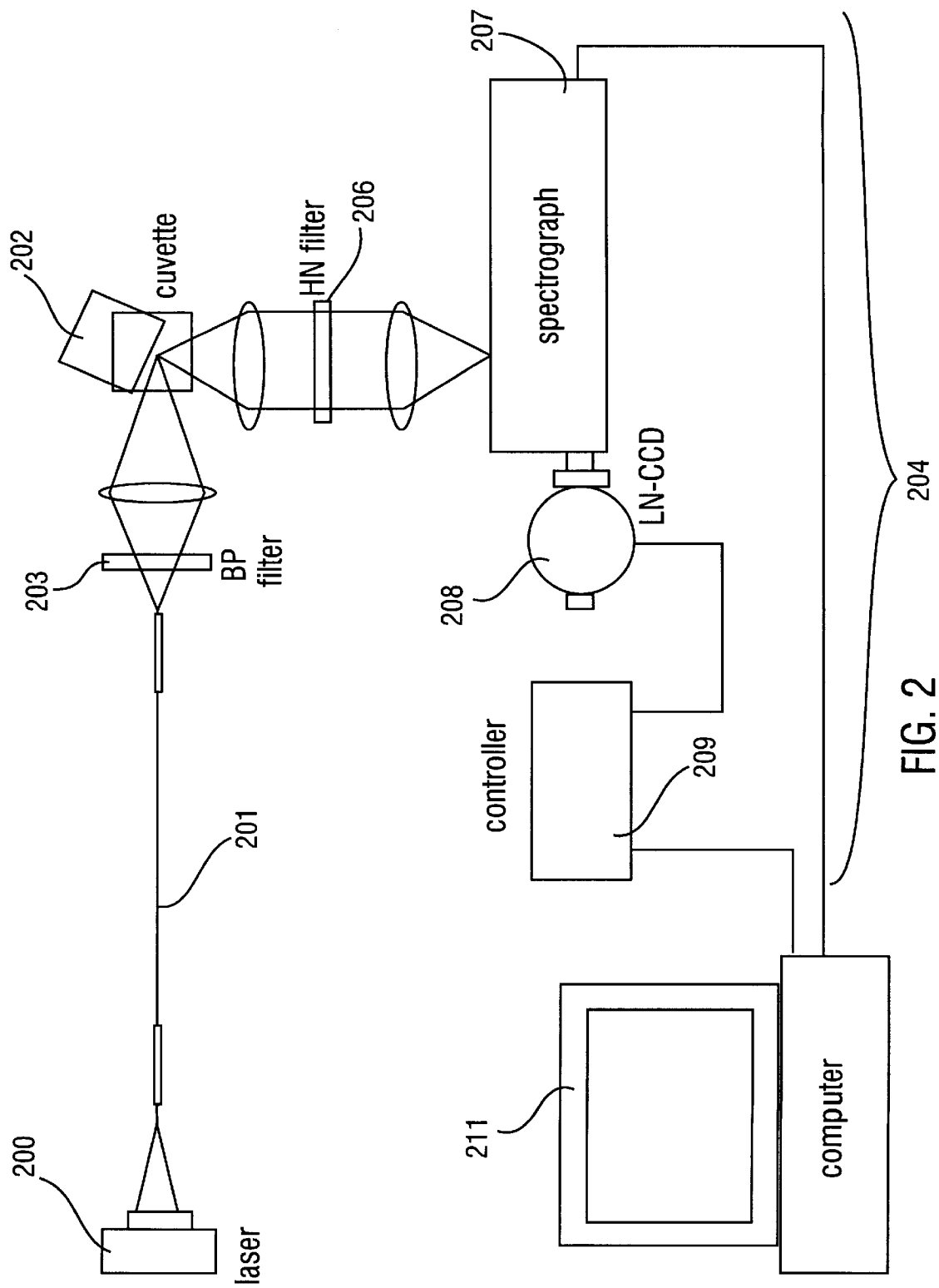
FIG. 2 is a block diagram an exemplary Raman spectroscopy diagnostic apparatus, in accordance with the present invention.

FIG. 2 is an exemplary apparatus for the collection of near-IR Raman spectra in accordance with the present invention. Near-IR Raman measurements were made in vitro using the system shown in FIG. 2, however the system of FIG. 2 could be readily adapted for use in vivo, for example by increasing laser power and by using a probe structure similar to that of probe 101 shown in FIGS. 1A and 1B. A 40 m W GaAlAs diode laser 200 (Diolite 800, LiCONix, CA) excites the samples near 789 nm through a 200 micron glass fiber 201. The biopsies measuring about 2×1×1 mm are placed moist in a quartz cuvette 202 with the epithelium towards the face of the cuvette 202 and the beam. The excitation beam is incident at an angle of approximately 75 degrees to avoid specular reflection and is focused to a spot size of 200 $\mu$m at the tissue surface. A bandpass (BP) filter 203 with a transmission of 85% at 789 nm is used to clean up the output of the laser 200. The laser power at the sample is maintained at approximately 25 mW. The scattered Raman signal is collected at an angle of 90° from the excitation beam and imaged on the entrance slit of the detection system 204, however other angles would also be acceptable. A holographic notch (HN) filter 206 (HSNF 789, Kaiger Optical Systems, MI) with an optical density >6 at 789 nm is used to attenuate the elastic scattering. The detection system 204 includes an imaging spectrograph 207 (500IS, Chromex Inc. NM) and a liquid nitrogen cooled CCD camera 208 with associated camera controller 209 (LN-1152E, Princeton Instruments, NJ). The spectrograph 207 was used with a 300 gr/mm grating blazed at 500 nm which yielded a spectral resolution of 10 $cm^{-1}$ with an entrance slit of 100 $\mu$m.

Detection system 204 is controlled by computer 211 which is programmed in accordance with the Raman spectroscopy diagnostic method described below in detail with reference to the flowcharts of FIGS. 4A–4D.

Raman spectra were measured over a range of 500–2000 $cm^{-1}$ with respect to the excitation frequency and each sample spectrum was integrated for 15 minutes, however, shorter integration times would also be acceptable combined with higher laser intensity. Each background subtracted spectrum was corrected for wavelength dependent response of the spectrograph 207, camera 208, grating and filters 203 and 206. The system was calibrated for day to day throughput variations using naphthalene, rhodamine 6G and carbon tetrachloride. The Raman shift was found to be accurate to $\pm 7$ $cm^{-1}$ and the intensity was found to be constant within 12% of the mean.

The systems of FIGS. 1 and 2 are exemplary embodiments and should not be considered to limit the invention as claimed. It will be understood that apparatus other than that depicted in FIGS. 1 and 2 may be used without departing from the scope of the invention.

III. Diagnostic Methods

1. Development of Diagnostic Methods

A. Two-Stage Method Development at 337 nm Excitation

The parameters for stage 1 of the two-stage method: relative peak intensity (peak intensity of each sample divided by the average peak intensity of corresponding normal (squamous) samples from the same patient) and a linear approximation of slope of the spectrum from 420–440 nm were calculated from the fluorescence spectrum of each sample in the calibration set. The relative peak intensity accounts for the inter-patient variation of normal tissue fluorescence intensity. A two-dimensional scattergram of the two diagnostic parameters was plotted for all the samples in the calibration set. A linear decision line was developed to minimize misclassification (non diseased vs. diseased). Similarly, the parameters for stage 2 of the method: slope of the spectrum from 440–460 nm of each diseased sample and average slope from 420–440 nm of spectra of corresponding normal (squamous) samples were calculated from the calibration set. A scattergram of the these two diagnostic parameters was plotted for all diseased samples. Again, a linear decision line was developed to minimize misclassification (low grade SIL vs. high grade SIL). The optimized method was implemented on spectra of each sample in the prediction set. The optimal decision lines developed from the data in the calibration set were compared to that developed in the initial clinical study for both stages of the method. The two-stage fluorescence diagnostic method is disclosed in more detail in application Ser. No. 08/060,432, filed May 12, 1993, assigned to the same assignee as the present invention. The disclosure of this prior application is expressly incorporated herein by reference.

B. Multi-Variate Statistical Method Development

The five primary steps involved in the multivariate statistical method are 1) preprocessing of spectral data from each patient to account for inter-patient variation, 2) partitioning of the preprocessed spectral data from all patients into calibration and prediction sets, 3) dimension reduction of the preprocessed spectra in the calibration set using principal component analysis, 4) selection of the diagnostically most useful principal components using a two-sided unpaired t-test and 5) development of an optimal classification scheme based on Bayes theorem using the diagnostically useful principal component scores of the calibration set as inputs. These five individual steps of the multivariate statistical method are presented below in more detail.

1) Preprocessing: The objective of preprocessing is to calibrate tissue spectra for inter-patient variation which might obscure differences in the spectra of different tissue types. Four methods of preprocessing were invoked on the spectral data: 1) normalization 2) mean scaling 3) a combination of normalization and mean scaling and 4) median scaling.

Spectra were normalized by dividing the fluorescence intensity at each emission wavelength by the maximum fluorescence intensity of that sample. Normalizing a fluorescence spectrum removes absolute intensity information; methods developed from normalized fluorescence spectra rely on differences in spectral line shape information for diagnosis. If the contribution of the absolute intensity information is not significant, two advantages are realized by utilizing normalized spectra: 1) it is no longer necessary to calibrate for inter-patient variation of normal tissue fluorescence intensity as in the two-stage method, and 2) identification of a colposcopically normal reference site in each patient prior to spectroscopic analysis is no longer needed.

Mean scaling was performed by calculating the mean spectrum for a patient (using all spectra obtained from cervical sites in that patient) and subtracting it from each spectrum in that patient. Mean-scaling can be performed on both unnormalized (original) and normalized spectra. Mean-scaling does not require colposcopy to identify a reference normal site in each patient prior to spectroscopic analysis. However, unlike normalization, mean-scaling displays the differences in the fluorescence spectrum from a particular site with respect to the average spectrum from that patient. Therefore this method can enhance differences in fluorescence spectra between tissue categories most effectively when spectra are acquired from approximately equal numbers of non diseased and diseased sites from each patient.

Median scaling is performed by calculating the median spectrum for a patient (using all spectra obtained from cervical sites in that patient) and subtracting it from each spectrum in that patient. Like mean scaling, median scaling can be performed on both unnormalized (original) and normalized spectra, and median scaling does not require colposcopy to identify a reference normal site in each patient prior to spectroscopic analysis. However, unlike mean scaling, median scaling does not require the acquisition of spectra from equal numbers of non diseased and diseased sites from each patient.

2) Calibration and Prediction Data Sets: The preprocessed spectral data were randomly assigned into either a calibration or prediction set. The multivariate statistical method was developed and optimized using the calibration set. It was then tested prospectively on the prediction data set.

3) Principal Component Analysis: Principal component analysis (PCA) is a linear model which transforms the original variables of a fluorescence emission spectrum into a smaller set of linear combinations of the original variables called principal components that account for most of the variance of the original data set. Principal component analysis is described in Dillon W. R., Goldstein M., *Multivariate Analysis: Methods and Applications*, John Wiley and Sons, 1984, pp. 23–52, the disclosure of which is expressly incorporated herein by reference. While PCA may not provide direct insight to the morphologic and biochemical basis of tissue spectra, it provides a novel approach of condensing all the spectral information into a few manageable components, with minimal information loss. Furthermore, each principal component can be easily related to the original emission spectrum, thus providing insight into diagnostically useful emission variables.

Prior to PCA, a data matrix is created where each row of the matrix contains the preprocessed fluorescence spectrum of a sample and each column contains the pre-processed fluorescence intensity at each emission wavelength. The data matrix D (r×c), consisting of r rows (corresponding to r total samples from all patients in the training set) and c columns (corresponding to intensity at c emission wavelengths) can be written as:

$$D = \begin{pmatrix} D_{11} & D_{12} & \ldots & D_{1c} \\ D_{21} & D_{22} & \ldots & D_{2c} \\ & & & \\ D_{r1} & D_{r2} & \ldots & D_{rc} \end{pmatrix} \quad (1)$$

The first step in PCA is to calculate the covariance matrix, Z. First, each column of the preprocessed data matrix D is mean-scaled. The mean-scaled preprocessed data matrix, $D_m$ is then multiplied by its transpose and each element of the resulting square matrix is divided by (r−1), where r is the total number of samples. The equation for calculating Z is defined as:

$$Z = \frac{1}{r-1}(D_m'D_m) \quad (2)$$

The square covariance matrix, Z (c×c) is decomposed into its respective eigenvalues and eigenvectors. Because of experimental error, the total number of eigenvalues will always equal the total number of columns (c) in the data matrix D assuming that c<r. The goal is to select n<c eigenvalues that can describe most of the variance of the original data matrix to within experimental error. The variance, V accounted for by the first n eigenvalues can be calculated as follows:

$$V = 100 \left( \frac{\sum_{j=1}^{n} \lambda_j}{\sum_{j=1}^{c} \lambda_j} \right) \quad (3)$$

The criterion used in this analysis was to retain the first n eigenvalues and corresponding eigenvectors that account for 99% of the variance in the original data set.

Next, the principal component score matrix can be calculated according to the following equation:

$$R = D\,C \quad (4)$$

where, D (r×c) is the preprocessed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal to each other.

Finally, the component loading is calculated for each principal component. The component loading represents the correlation between the principal component and the variables of the original fluorescence emission spectrum. The component loading can be calculated as shown below:

$$CL_{ij} = \frac{C_{ij}}{\sqrt{S_{ii}}}\sqrt{\lambda_j} \quad (5)$$

where, $CL_{ij}$ represents the correlation between the ith variable (preprocessed intensity at ith emission wavelength) and the jth principal component. $C_{ij}$ is the ith component of the jth eigenvector, $\lambda_j$ is the jth eigenvalue and $S_{ii}$ is the variance of the ith variable.

Principal component analysis was performed on each type of preprocessed data matrix, described above. Eigenvalues accounting for 99% of the variance in the original preprocessed data set were retained The corresponding eigenvectors were then multiplied by the original data matrix to obtain the principal component score matrix R.

4) Student's T-Test: Average values of principal component scores were calculated for each histo-pathologic tissue category for each principal component obtained from the preprocessed data matrix. A two-sided unpaired student's t-test was employed to determine the diagnostic contribution of each principal component. Such a test is disclosed in Devore J. L., *Probability and Statistics for Engineering and the Sciences*, Brooks/Cole, 1992, and in Walpole R. E., Myers R. H., *Probability and Statistics for Engineers and Scientists*, Macmillan Publishing Co., 1978, Chapter 7, the disclosures of which are expressly incorporated herein by reference. The hypothesis that the means of the principal component scores of two tissue categories are different were tested for 1) normal squamous epithelia and SILs, 2) columnar normal epithelia and SILs and 3) inflammation and SILs. The t-test was extended a step further to determine if there are any statistically significant differences between the means of the principal component scores of high grade SILs and low grade SILs. Principal components for which the hypothesis stated above were true below the 0.05 level of significance were retained for further analysis.

5) Logistic Discrimination: Logistic discriminant analysis is a statistical technique that can be used to develop diagnostic methods based on posterior probabilities, overcoming the drawback of the binary decision scheme employed in the two-stage method. This statistical classification method is based on Bayes theorem and can be used to calculate the posterior probability that an unknown sample belongs to each of the possible tissue categories identified. Logistic discrimination is discussed in Albert A., Harris E. K., *Multivariate Interpretation of Clinical Laboratory Data*, Marcel Dekker, 1987, the disclosure of which is expressly incorporated herein by reference. Classifying the unknown sample into the tissue category for which its posterior probability is highest results in a classification scheme that minimizes the rate of misclassification.

For two diagnostic categories, $G_1$ and $G_2$, the posterior probability of being a member of $G_1$, given measurement x, according to Bayes theorem is:

$$P(G_1 \mid X) = \frac{P(x \mid G_1)P(G_1)C(2 \mid 1)}{P(x \mid G_1)P(G_1)C(2 \mid 1) + P(x \mid G_2)P(G_2)C(1 \mid 2)} \quad (6)$$

where $P(x|G_i)$ is the conditional joint probability that a tissue sample of type i will have principal component score x, and $P(G_i)$ is the prior probability of finding tissue type i in the sample population. C(j|i) is the cost of misclassifying a sample into group j when the actual membership is group i.

The prior probability $P(G_i)$ is an estimate of the likelihood that a sample of type i belongs to a particular group when no information about it is available. If the sample is considered representative of the population, the observed proportions of cases in each group can serve as estimates of the prior probabilities. In a clinical setting, either historical incidence figures appropriate for the patient population can be used to generate prior probabilities, or the practitioner's colposcopic assessment of the likelihood of precancer can be used to estimate prior probabilities.

The conditional probabilities can be developed from the probability distributions of the n principal component scores for each tissue type, i. The probability distributions can be modeled using the gamma function, which is characterized by two parameters, alpha and beta, which are related to the mean and standard deviation of the data set. The Gamma function is typically used to model skewed distributions and is defined below:

$$f(x; \alpha, \beta) = \frac{1}{\beta^\alpha \Gamma(\alpha)} x^{\alpha-1} e^{-\frac{x}{\beta}} \quad (7)$$

The gamma function can be used to calculate the conditional probability that a sample from tissue type i, will exhibit the principal component score, x. If more than one principal component is needed to describe a sample population, then the conditional joint probability is simply the product of the conditional probabilities of each principal component (assuming that each principal component is an independent variable) for that sample population.

C. Multivariate Analysis of Tissue Fluorescence Spectra

1) SILs vs. Normal Squamous Tissue at 337 nm excitation

A summary of the fluorescence diagnostic method developed and tested in a previous group of 92 patients (476 sites) is presented here. The spectral data were preprocessed by normalizing each spectrum to a peak intensity of one, followed by mean-scaling. Mean scaling is performed by calculating the mean spectrum for a patient (using all spectra obtained from cervical sites in that patient) and subtracting it from each spectrum in that patient. Next, principal component analysis (PCA) is used to transform the original variables of each preprocessed fluorescence emission spectrum into a smaller set of linear combinations called principal components that account for 99% of the variance of the original data set. Only the diagnostically useful principal components are retained for further analysis. Posterior probabilities for each tissue type are determined for all samples in the data set using calculated prior and conditional joint probabilities. The prior probability is calculated as the percentage of each tissue type in the data. The conditional probability was calculated from the gamma function which modeled the probability distributions of the retained principal components scores for each tissue category. The entire data set was split in two groups: calibration and prediction data set such that their prior probabilities were approximately equal. The method is optimized using the calibration set and then implemented on the prediction set to estimate its performance in an unbiased manner. The methods using PCA and Bayes theorem were developed using the calibration set consisting of previously collected spectra from 46 patients (239 sites). These methods were then applied to the prediction set (previously collected spectra from another 46 patients; 237 sites) and the current data set of 36 samples.

More specifically, at 337 nm excitation, fluorescence spectra were acquired from a total of 476 sites in 92 patients. The data were randomly assigned to either a calibration set or prediction set with the condition that both sets contain roughly equal number of samples from each histopathologic category, as shown in Table 1.

TABLE 1

(a) Histo-pathologic classification of samples in the training and the validation set examined at 337 nm excitation and (b) histological classification of cervical samples spectroscopically interrogated in vivo from 40 patients at 380 nm excitation and 24 patients in 460 nm excitation.

(a)

| Histology | Training Set | Validation Set |
| --- | --- | --- |
| Squamous Normal | 127 | 126 |
| Columnar Normal | 25 | 25 |
| Inflammation | 16 | 16 |
| Low Grade SIL | 40 | 40 |
| High Grade SIL | 31 | 30 |

(b)

| Histology | 380 nm excitation (40 patients) | 460 nm excitation (24 patients) |
| --- | --- | --- |
| Squamous Normal | 82 | 76 |
| Columnar Normal | 20 | 24 |
| Inflammation | 10 | 11 |
| Low Grade SIL | 28 | 14 |
| High Grade SIL | 15 | 22 |

The random assignment ensured that not all spectra from a single patient were contained in the same data set. The purpose of the calibration set is to develop and optimize the method and the purpose of the prediction set is to prospectively test its accuracy in an unbiased manner. The two-stage method and the multivariate statistical method were optimized using the calibration set. The performance of these methods were then tested prospectively on the prediction set.

Principal component analysis of mean-scaled normalized spectra at 337 nm excitation from the calibration data set resulted in 3 principal components accounting for 99% of the total variance. Only, the first two principal components obtained from the preprocessed data matrix containing mean-scaled normalized spectra demonstrate the statistically most significant differences (P<0.05) between normal squamous tissues and SILs (PC1: P<1E-25, PC2: P<0.006). The two-tail P values of the scores of the third principal component were not statistically significant (P<0.2). Therefore, the rest of the analysis was performed using these two principal components. All of the principal components are included in Appendix II.

For excitation at 337 nm, the prior probability was determined by calculating the percentage of each tissue type in the calibration set: 65% normal squamous tissues and 35% SILs. More generally, prior probabilities should be selected to describe the patient population under study; the values used here are appropriate as they describe the prediction set as well.

Figure 5:
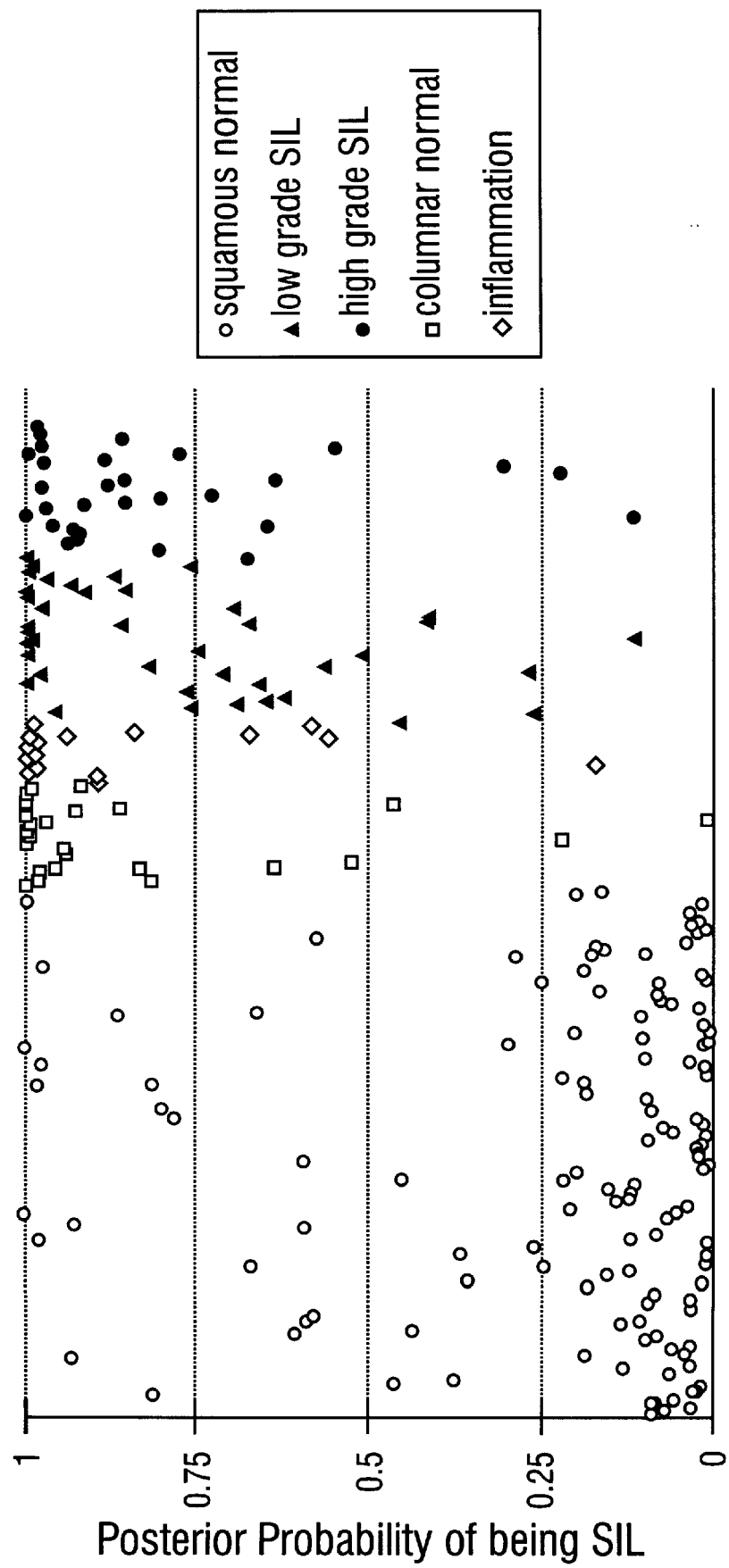
FIGS. 5 and 6 are graphs depicting the performance of the fluorescence diagnostic method of the present invention, with 337 nm excitation.

Posterior probabilities of belonging to each tissue type (normal squamous or SIL) were calculated for all samples in the calibration set, using the known prior probabilities and the conditional probabilities calculated from the gamma function. A cost of misclassification of SILs equal to 0.5 was assumed. FIG. 5 illustrates the posterior probability of belonging to the SIL category. The posterior probability is plotted for all samples in the calibration set. This plot indicates that 75% of the high grade SILs have a posterior probability greater than 0.75 and almost 90% of high grade SILs have a posterior probability greater than 0.6. While 85% of low grade SILs have a posterior probability greater than 0.5, only 60% of low grade SILs have a posterior probability greater than 0.75. More than 80% of normal squamous epithelia have a posterior probability less than 0.25. Note that evaluation of normal columnar epithelia and samples with inflammation using this method results in classifying them as SILs.

Figure 6:
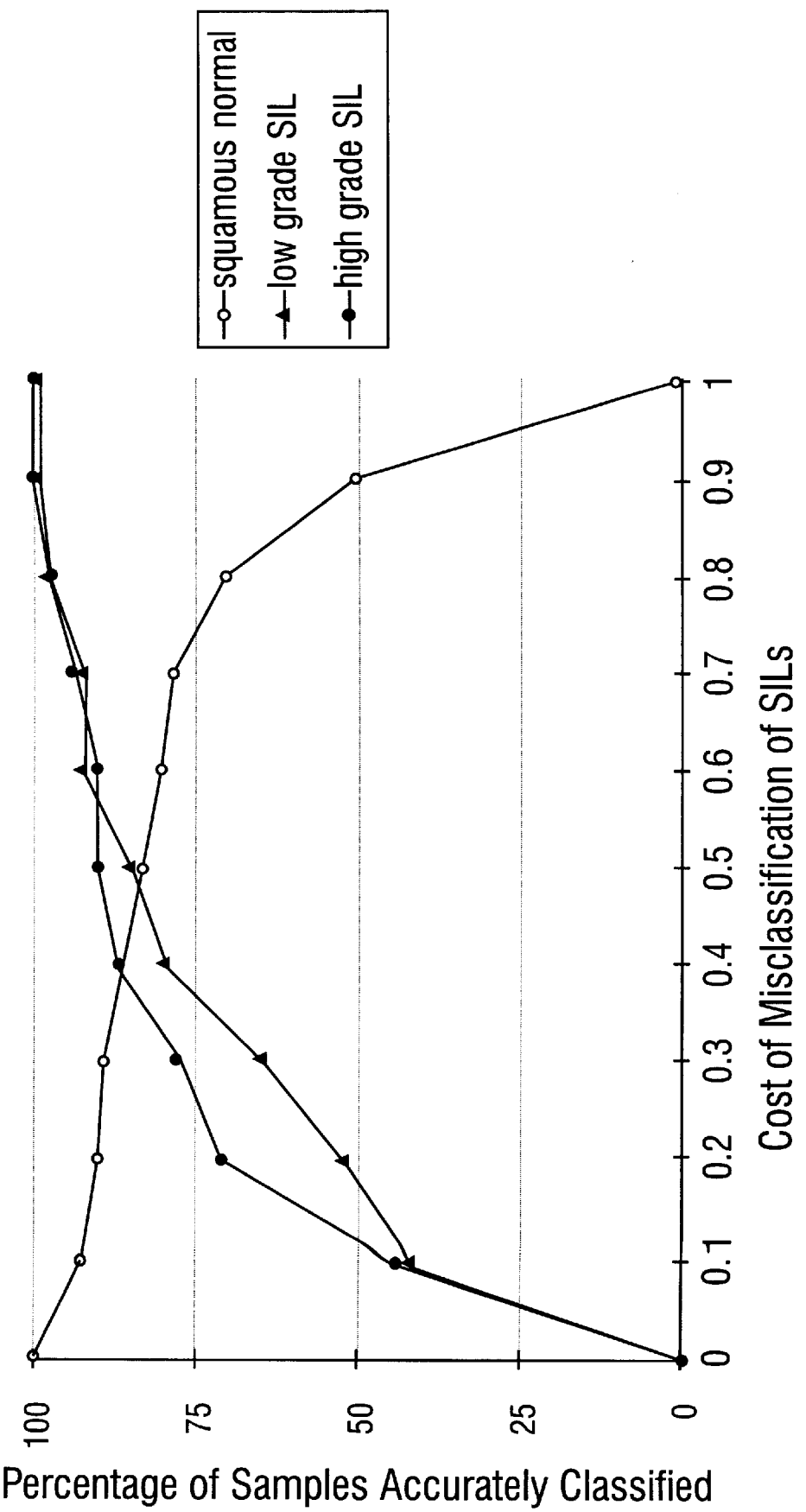

FIG. 6 shows the percentage of normal squamous tissues and SILs correctly classified versus cost of misclassification of SILs for the data from the calibration set. An increase in the SIL misclassification cost results in an increase in the proportion of correctly classified SILs and a decrease in the proportion of correctly classified normal squamous tissues. Note, that varying the cost from 0.4 to 0.6 alters the classification accuracy of both SILs and normal tissues by less than 15% indicating that a small change in the cost does not significantly alter the performance of the method. An optimal cost of misclassification would be 0.6–0.7 as this correctly classifies almost 95% of SILs and 80% of normal squamous epithelia, for the prior probabilities used and is not sensitivity to small changes in prior probability.

The method was implemented on mean-scaled spectra of the prediction set, to obtain an unbiased estimate of its accuracy. The two eigenvectors obtained from the calibration set were multiplied by the prediction matrix to obtain the new principal component score matrix. Using the same prior probabilities, a cost of misclassification of SILs equal to 0.5, and conditional joint probabilities calculated from the gamma function, developed from the calibration set, Bayes rule was used to calculate the posterior probabilities for all samples in the prediction set.

Confusion matrices in Tables 2(a) and 2(b) show the spectroscopic classification using this method for the calibration set and the prediction set, respectively. A comparison of the sample classification between the prediction and calibration sets indicates that the method performs within 7% on an unknown data set of approximately equal prior probability.

TABLE 2

Results of multivariate statiatical method applied to the entire fluorescence emission spectra of squamous normal tissues and SILs at 337 nm excitation in (a) calibration set and (b) prediction set.

| Classification | Squamous Normal | Low Grade SIL | High Grade SIL |
| --- | --- | --- | --- |
| (a) | | | |
| Squamous Normal | 83% | 15% | 10% |
| SIL | 17% | 85% | 90% |
| (b) | | | |
| Squamous Normal | 81% | 22% | 6% |
| SIL | 19% | 78% | 94% |

The utility of another parameter called the component loadings was explored for reducing the number of emission variables required to achieve classification with minimal decrease in predictive ability. Portions of the emission spectrum most highly correlated (correlation >0.9 or <0.9) with the component loadings were selected and the reduced data matrix was used to regenerate and evaluate the method. Using intensity at 2 emission wavelengths, the method was developed in an identical manner as was done with the entire emission spectrum. It was optimized using the calibration set and implemented on the prediction set. A comparison of the sample classification based on the method using the entire emission spectrum to that using intensity at 2 emission wavelengths indicates that the latter method performs equally well in classifying normal squamous epithelia and low grade SILs. The performance of the latter method is 6% lower for classifying high grade SILs.

2) SILs vs. Normal Columnar Epithelia and Inflammation at 380 nm Excitation

Principal components obtained from the preprocessed data matrix containing mean-scaled normalized spectra at 380 nm excitation could be used to differentiate SILs from non diseased tissues (normal columnar epithelia and inflammation). The principal components are included in Appendix II. Furthermore, a two-sided unpaired t-test indicated that only principal component 2 (PC2) and principal component 5 (PC5) demonstrated the statistically most significant differences ($p \leq 0.05$) between SILs and non diseased tissues (normal columnar epithelia and inflammation). The p values of the remaining principal component scores were not statistically significant (p>0.13) Therefore, the rest of the analysis was performed using these three principal components which account collectively for 32% of the variation in the original data set.

Figure 7A:
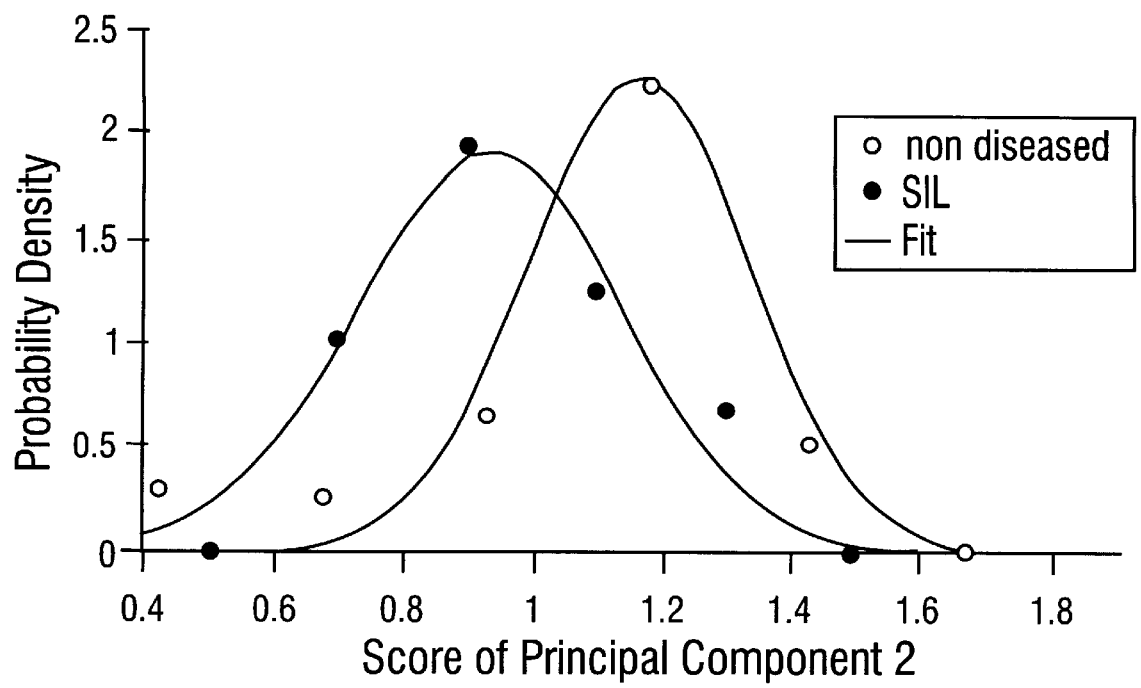
FIGS. 7A, 7B and 8 are graphs illustrating the performance of the fluorescence spectrum diagnostic method of the present invention at 380 nm excitation.
Figure 7B:
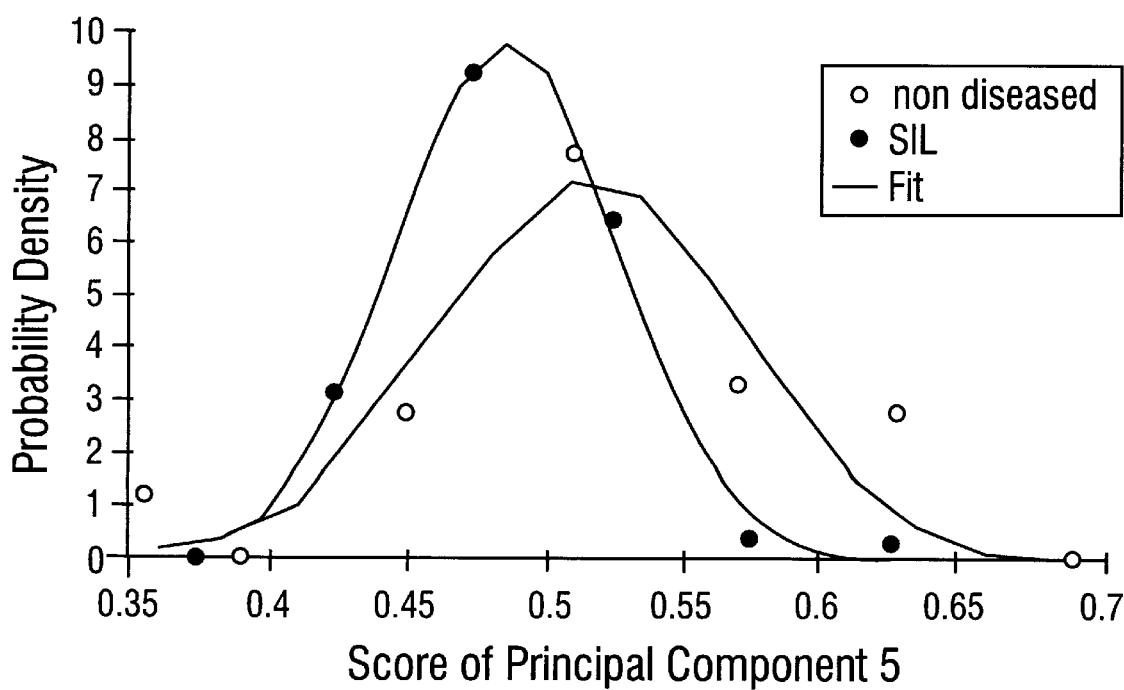
Figure 8:
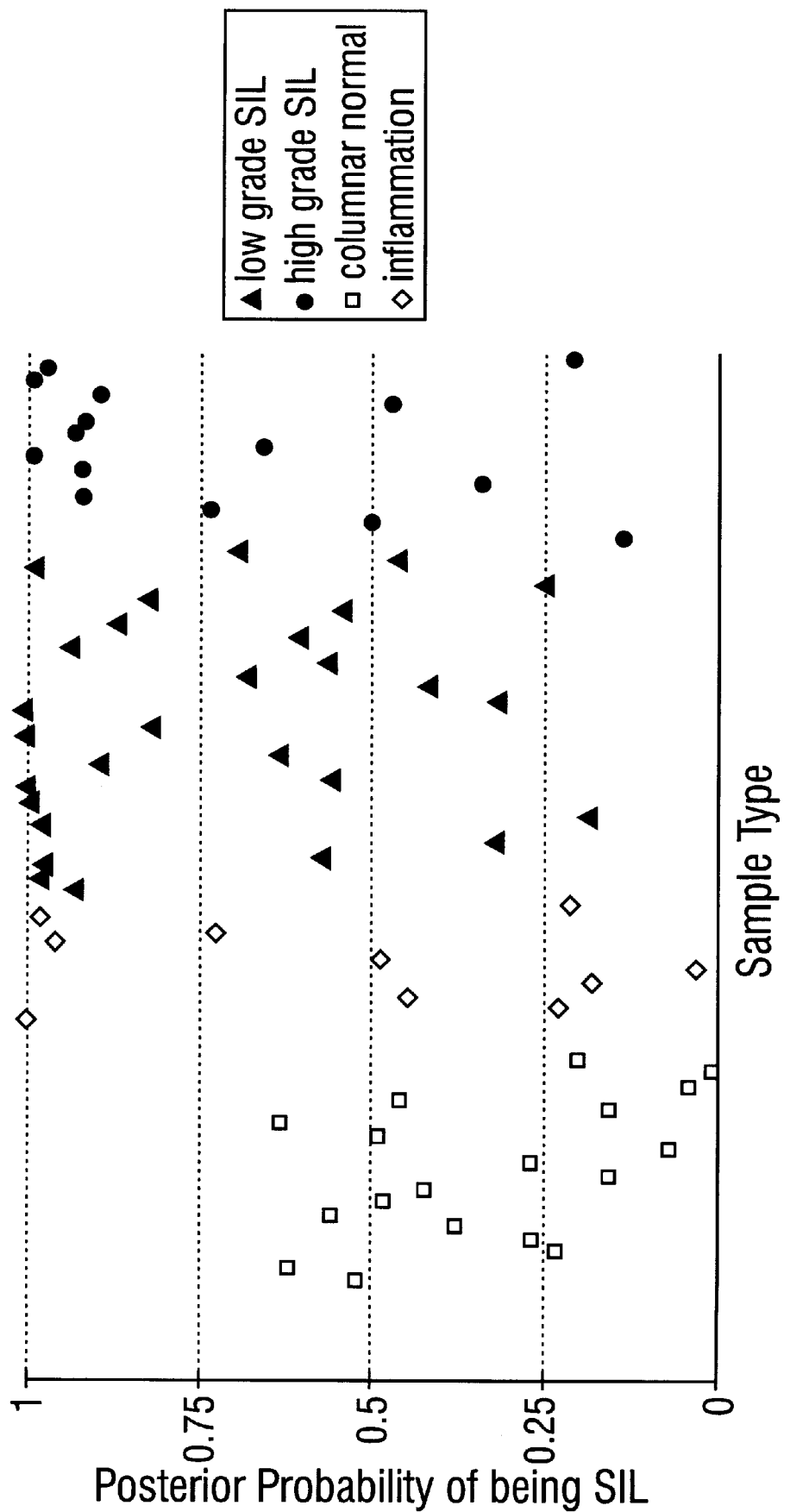

FIGS. 7A and 7B illustrate the measured probability distribution and the best fit of the normal probability density function to PC2 and PC5 of non diseased tissues and SILs, respectively. There is reasonable agreement between the measured and calculated probability distribution, for each case. The prior probability was determined by calculating the percentage of each tissue type in the data set: 41% non diseased tissues and 59% SILs. Posterior probabilities of belonging to each tissue type were calculated for all samples in the data set, using the known prior probabilities and the conditional joint probabilities calculated from the normal probability density function. FIG. 8 illustrates the retrospective performance of the diagnostic method on the same data set used to optimize it. The posterior probability of being classified into the SIL category is plotted for all samples evaluated. The results shown are for a cost of misclassification of SILs equal to 50%. FIG. 8 indicates that 78% of SILs have a posterior probability greater than 0.5, 78% of normal columnar tissues have a posterior probability less than 0.5 and 60% of samples with inflammation have a posterior probability less than 0.5. Note that, there are only 10 samples with inflammation in this study.

Tables 3 (a) and (b) compare (a) the retrospective performance of the diagnostic method on the data set used to optimize it to (b) a prospective estimate of the method's performance using cross-validation. Table 3(a) indicates that for a cost of misclassification of 50%, 74% of high grade SILs, 78% of low grade SILs, 78% of normal columnar samples and 60% of samples with inflammation are correctly classified. The unbiased estimate of the method's performance (Table 3(b)) indicates that there is no change in the percentage of correctly classified SILs and approximately only a 10% decrease in the proportion of correctly classified normal columnar samples.

TABLE 3

(a) A retrospective and (b) prospective estimate of the multivariate statistical method's performance using mean-scaled normalized spectra at 380 nm excitation to differentiate SILs from non diseased tissues (normal columnar epithelia and inflammation).

| Classification | Normal Columnar | Inflammation | Low Grade SIL | High Grade SIL |
|---|---|---|---|---|
| | | (a) | | |
| Non diseased | 78% | 60% | 21% | 26% |
| SIL | 22% | 40% | 79% | 74% |
| | | (b) | | |
| Non diseased | 65% | 30% | 22% | 26% |
| SIL | 35% | 70% | 78% | 74% |

3) Squamous Normal Tissue vs. SILs at 460 nm Excitation

Principal components obtained from the preprocessed data matrix containing mean-scaled normalized spectra at 460 nm excitation could be used to differentiate SIL from normal squamous tissue. These principal components are included in Appendix II. Only principal components 1 and 2 demonstrated the statistically most significant differences ($p \leq 0.05$) between SILs and normal squamous tissues. The p values of the remaining principal component scores, were not statistically significant (p>0.06). Therefore, the rest of the analysis was performed using these two principal components which account collectively for 75% of the variation in the original data set.

Figure 9A:
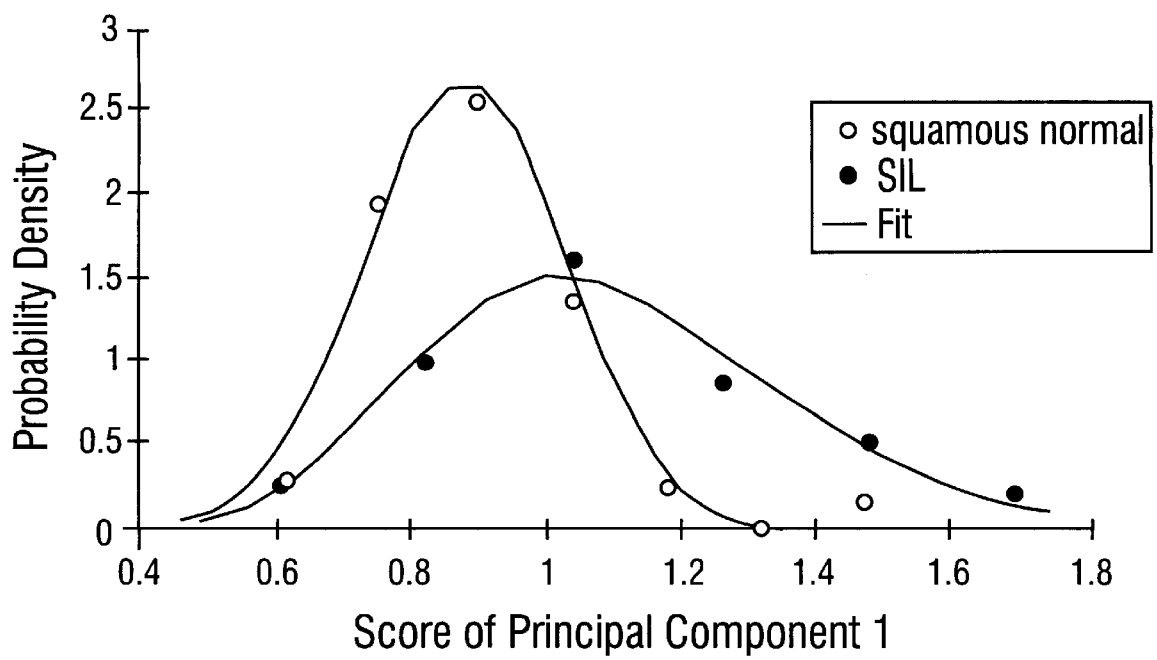
FIGS. 9A, 9B and 10 are graphs illustrating the performance of the fluorescence spectrum diagnostic method of the present invention to distinguish squamous normal tissue from SIL at 460 nm excitation.
Figure 9B:
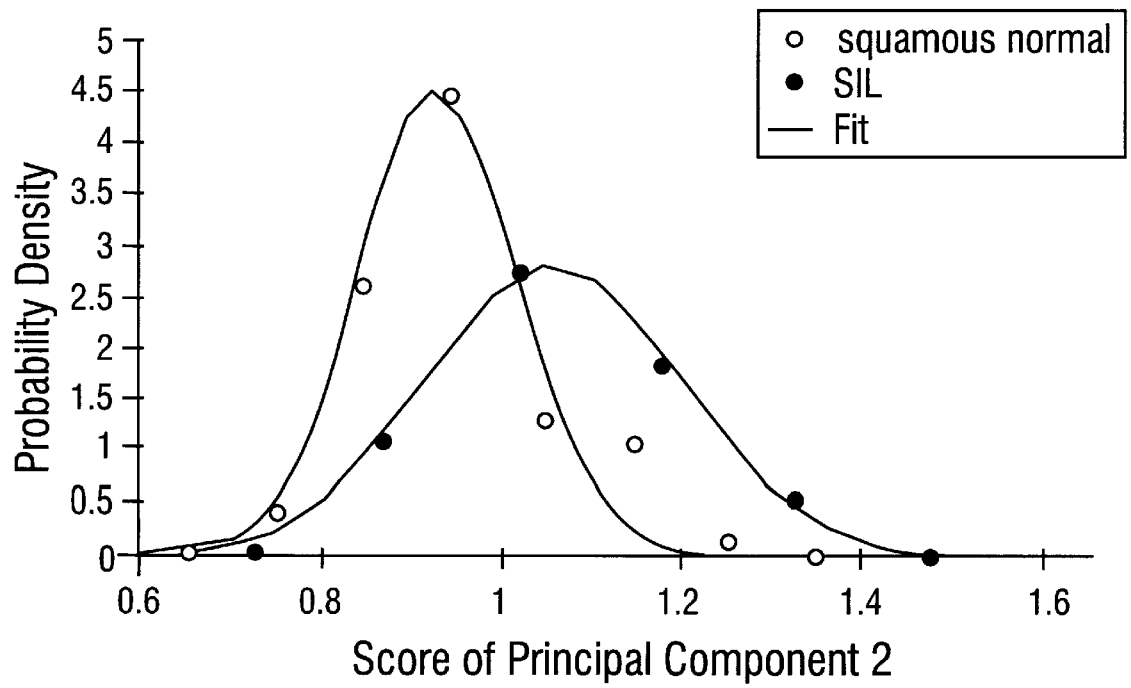
Figure 10:
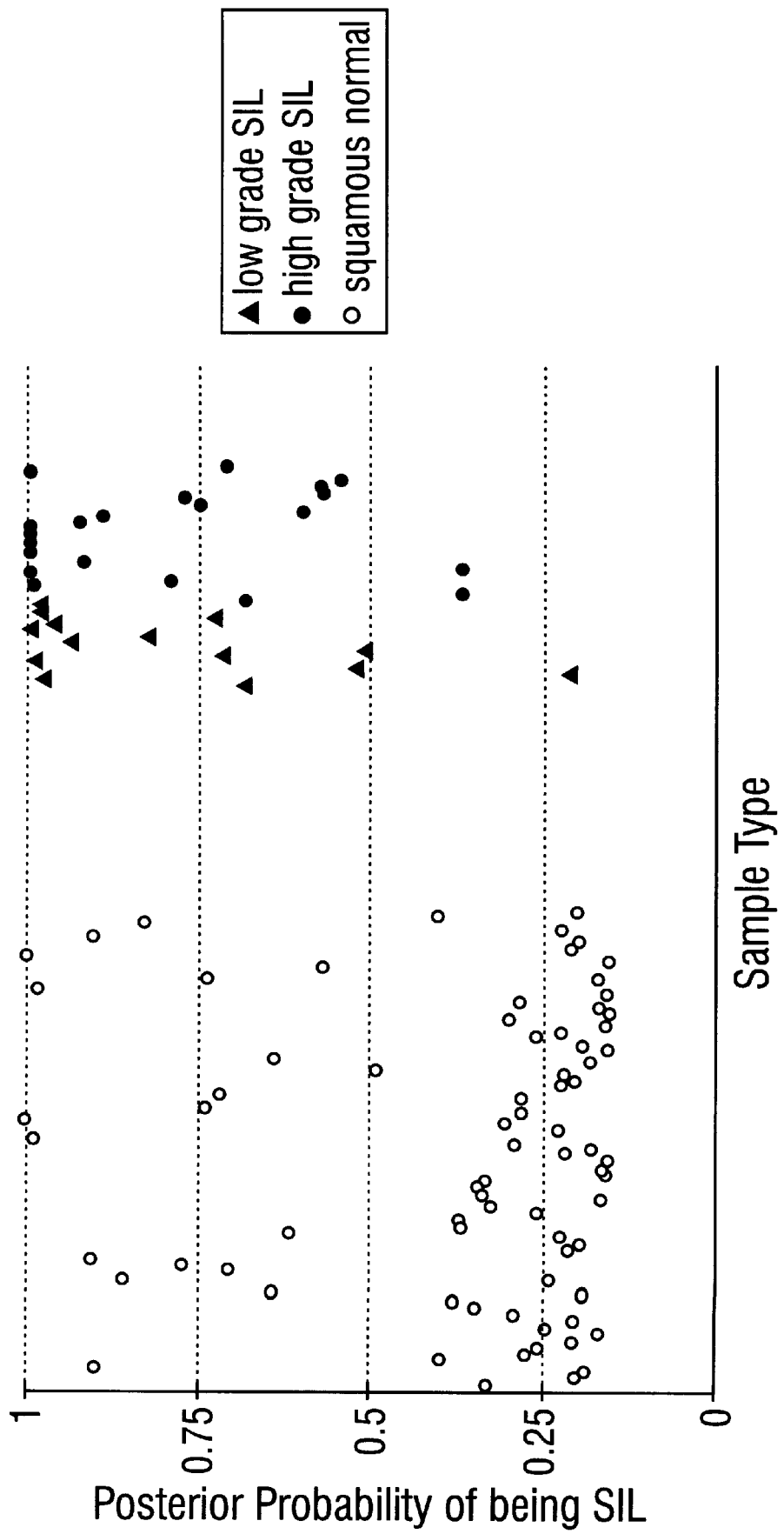

FIGS. 9A and 9B illustrate the measured probability distribution and the best fit of the normal probability density function to PC1 and PC2 of normal squamous tissues and SILs, respectively. There is reasonable agreement between the measured and calculated probability distribution, for each case. The prior probabilities were determined to be: 67% normal squamous tissues and 33% SILs. Next, posterior probabilities of belonging to each tissue type were calculated for all samples in the data set. FIG. 10 illustrates the retrospective performance of the diagnostic method on the same data set used to optimize it. The posterior probability of being classified into the SIL category is plotted for all samples evaluated. The results shown are for a cost of misclassification of SILs equal to 55%. FIG. 10 indicates that 92% of SILs have a posterior probability greater than 0.5, and 76% of normal squamous tissues have a posterior probability less than 0.5.

A prospective estimate of the method's performance was obtained using cross-validation. Table 4 (a) and (b) compares (a) the retrospective performance of the method on the data set used to optimize it to (b) the prospective estimate of the method's performance using cross-validation. Table 4(a) indicates that for a cost of misclassification of SILs equal to 55%, 92% of high grade SILs, 90% of low grade SILs, and 76% of normal squamous samples are correctly classified. The unbiased estimate of the method's performance (Table 4(b)) indicates that there is no change in the percentage of correctly classified high grade SILs or normal squamous tissue; there is a 5% decrease in the proportion of correctly classified low grade SILs.

TABLE 4

(a) A retrospective and (b) prospective
estimate of the multivariate statistical method's
performance using mean-scaled normalized spectra at 460.
nm excitation to differentiate SILs from normal squamous tissues

| Classification | Normal Squamous | Low Grade SIL | High Grade SIL |
|---|---|---|---|
| (a) | | | |
| Normal Squamous | 76% | 7% | 9% |
| SIL | 24% | 93% | 91% |
| (b) | | | |
| Normal Squamous | 75% | 14% | 9% |
| SIL | 25% | 86% | 91% |

4) Low Grade SILs vs. High Grade SILs at 460 nm Excitation

Principal components obtained from the preprocessed data matrix containing normalized spectra at 460 nm excitation could be used to differentiate high grade SILs from low grade SILs. These principal components are included in Appendix II. Principal component 4 (PC4) and principal component 7 (PC7) demonstrated the statistically most significant differences (p<0.05) between high grade SILs and low grade SILs. The p values of the remaining principal component scores were not statistically significant (p>0.09). Therefore, the rest of the analysis was performed using these two principal components which account collectively for 8% of the variation in the original data set.

Figure 11A:
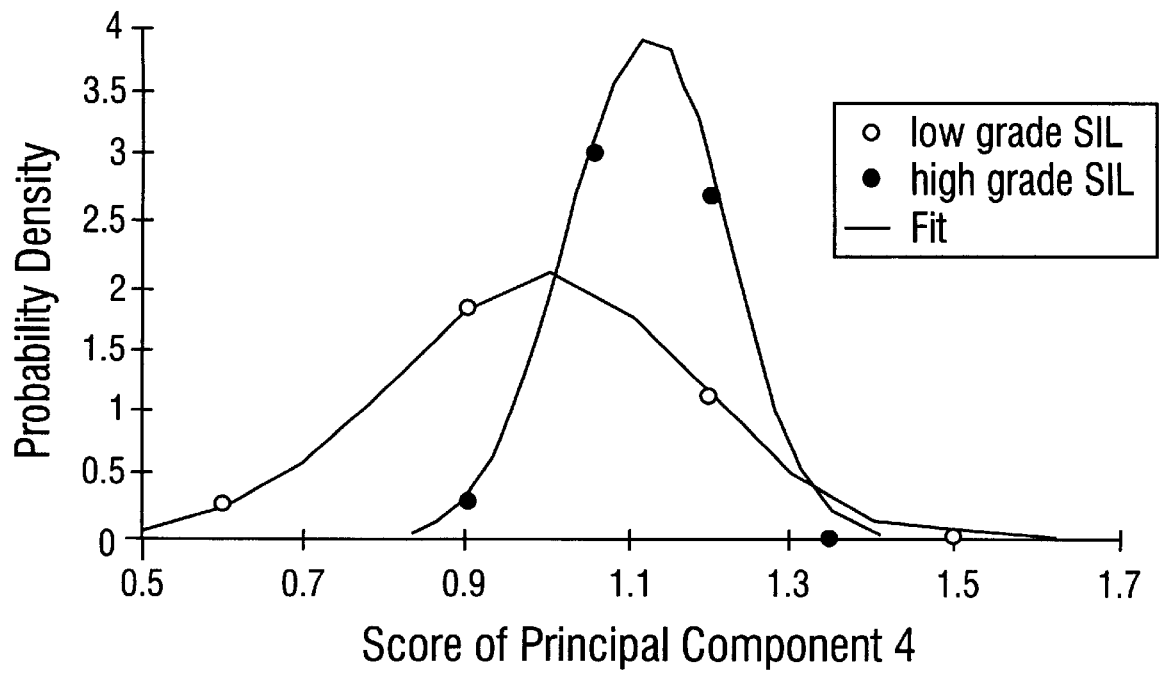
FIGS. 11A, 11B and 12 are graphs illustrating the performance of the fluorescence spectrum diagnostic method of the present invention, to distinguish low grade SIL from high grade SIL at 460 nm excitation.
Figure 11B:
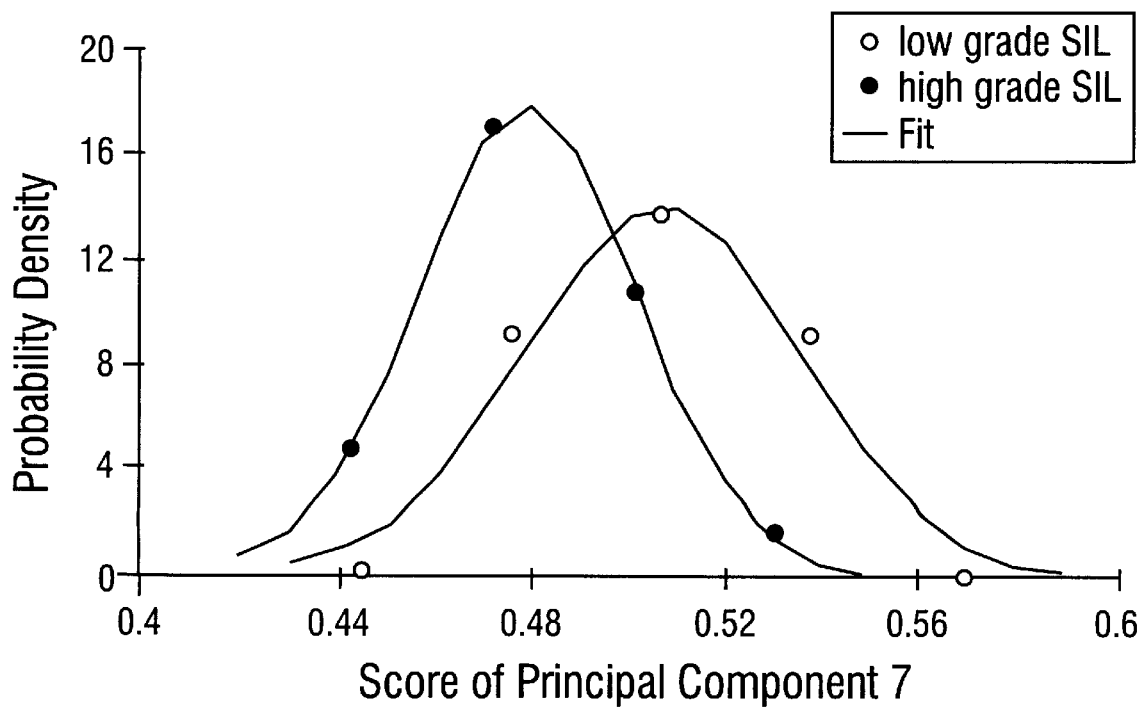
Figure 12:
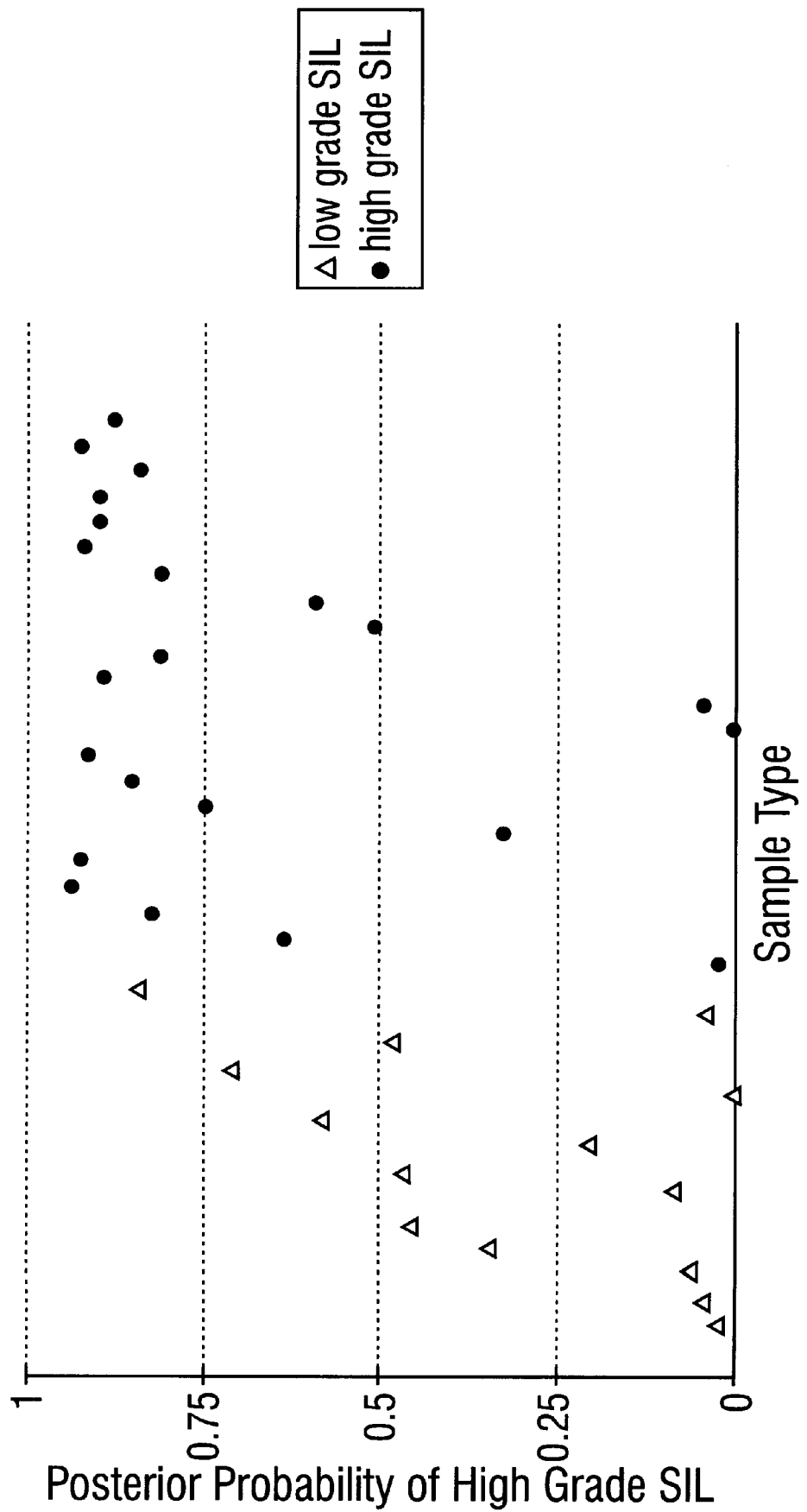

FIGS. 11A and 11B illustrate the measured probability distribution and the best fit of the normal probability density function of PC4 and PC7 for normal squamous tissues and SILs, respectively. There is reasonable agreement between the measured and calculated probability distribution, for each case. The prior probability was determined to be: 39% low grade SILs and 61% high grade SILs. Posterior probabilities of belonging to each tissue type were calculated. FIG. 12 illustrates the retrospective performance of the diagnostic method on the same data set used to optimize it. The posterior probability of being classified into the SIL category is plotted for all samples evaluated. The results shown are for a cost of misclassification of SILs equal to 65%. FIG. 12 indicates that 82% of high grade SILs have a posterior probability greater than 0.5, and 78% of low grade SILs have a posterior probability less than 0.5.

A prospective estimate of the method's performance was obtained using cross-validation. Table 5 (a) and (b) compares (a) the retrospective performance of the method on the data set used to optimize it to (b) the unbiased estimate of the method's performance using cross-validation. Table 5(a) indicates that for a cost of misclassification of 65% 82% of high grade SILs and 78% of low grade SILs are correctly classified. The unbiased estimate of the method's performance (Table 5(b)) indicates that there is a 5% decrease in the percentage of correctly classified high grade SILs and low grade SILs.

TABLE 5

(a) A retrospective and (b) prospective
estimate of the multivariate statistical method's
performance using mean-scaled normalized spectra at 460
nm excitation to differentiate high grade from low grade SILs.

| Classification | Low Grade SIL | High Grade SIL |
|---|---|---|
| (a) | | |
| Low Grade SIL | 79% | 18% |
| High Grade SIL | 21% | 82% |
| (b) | | |
| Low Grade SIL | 72% | 27% |
| High Grade SIL | 21% | 77% |

Figure 3A:
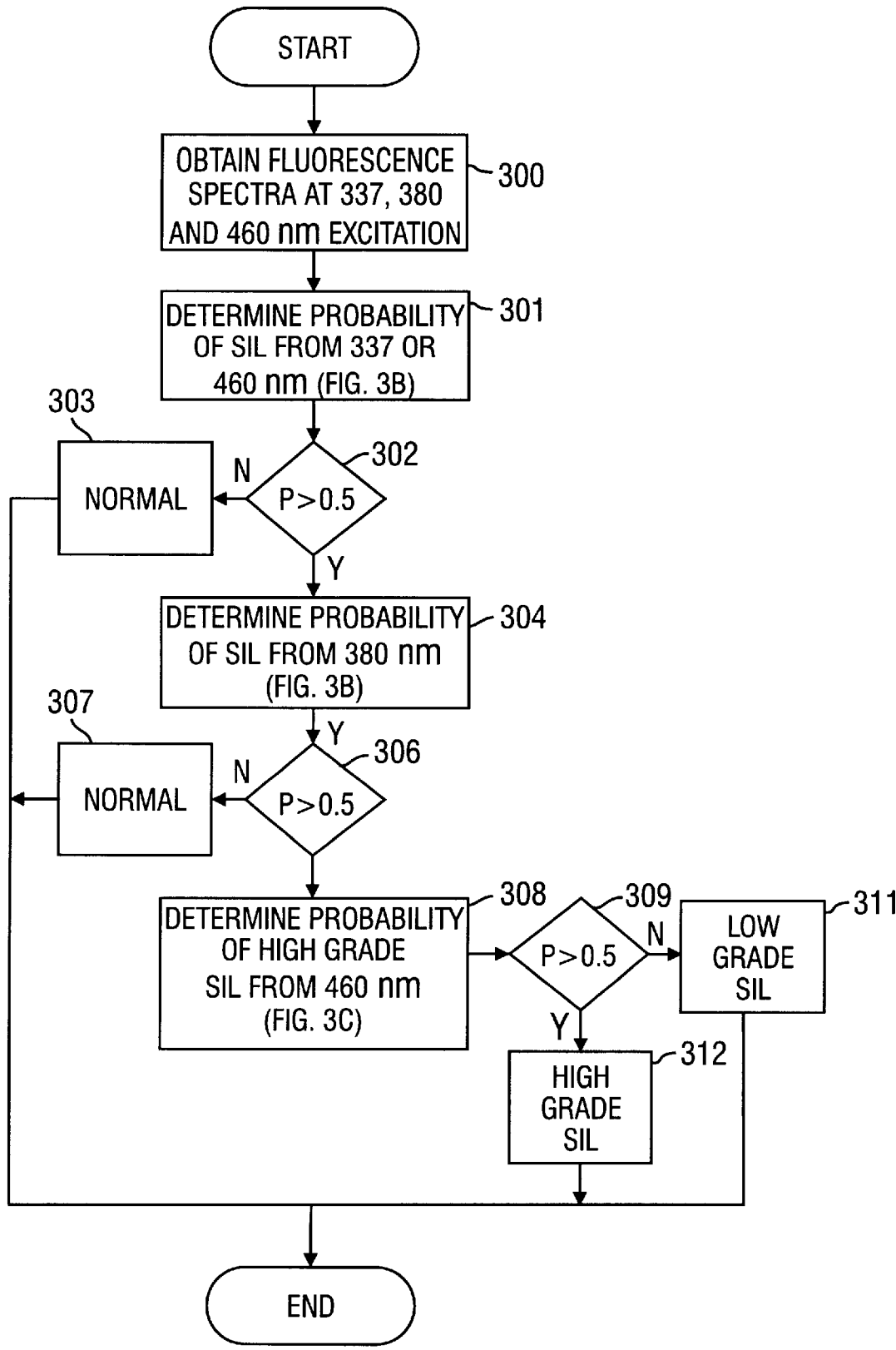
FIGS. 3A–3C are flowcharts of exemplary fluorescence spectroscopy diagnostic methods, in accordance with the present invention.
Figure 3B:
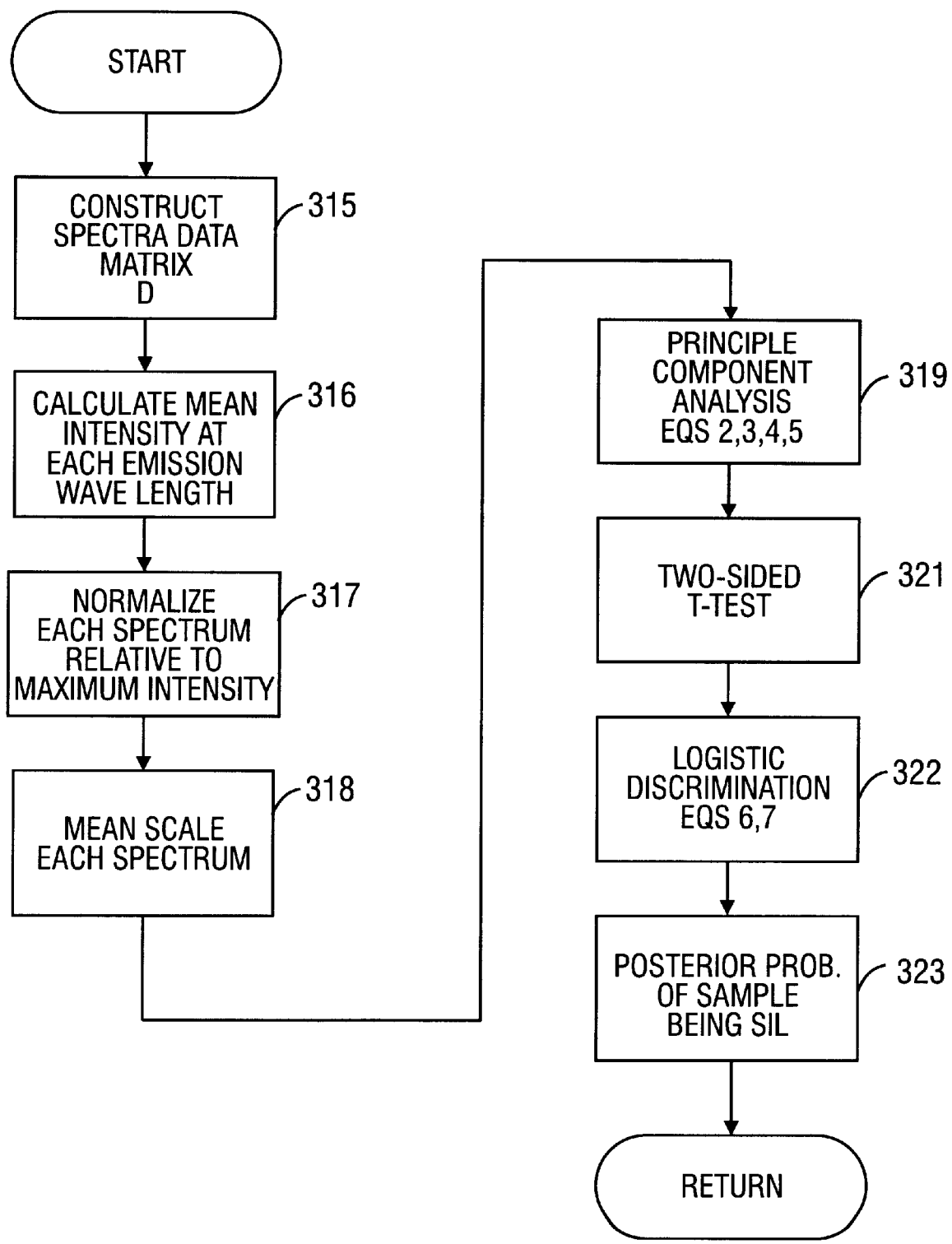
Figure 3C:
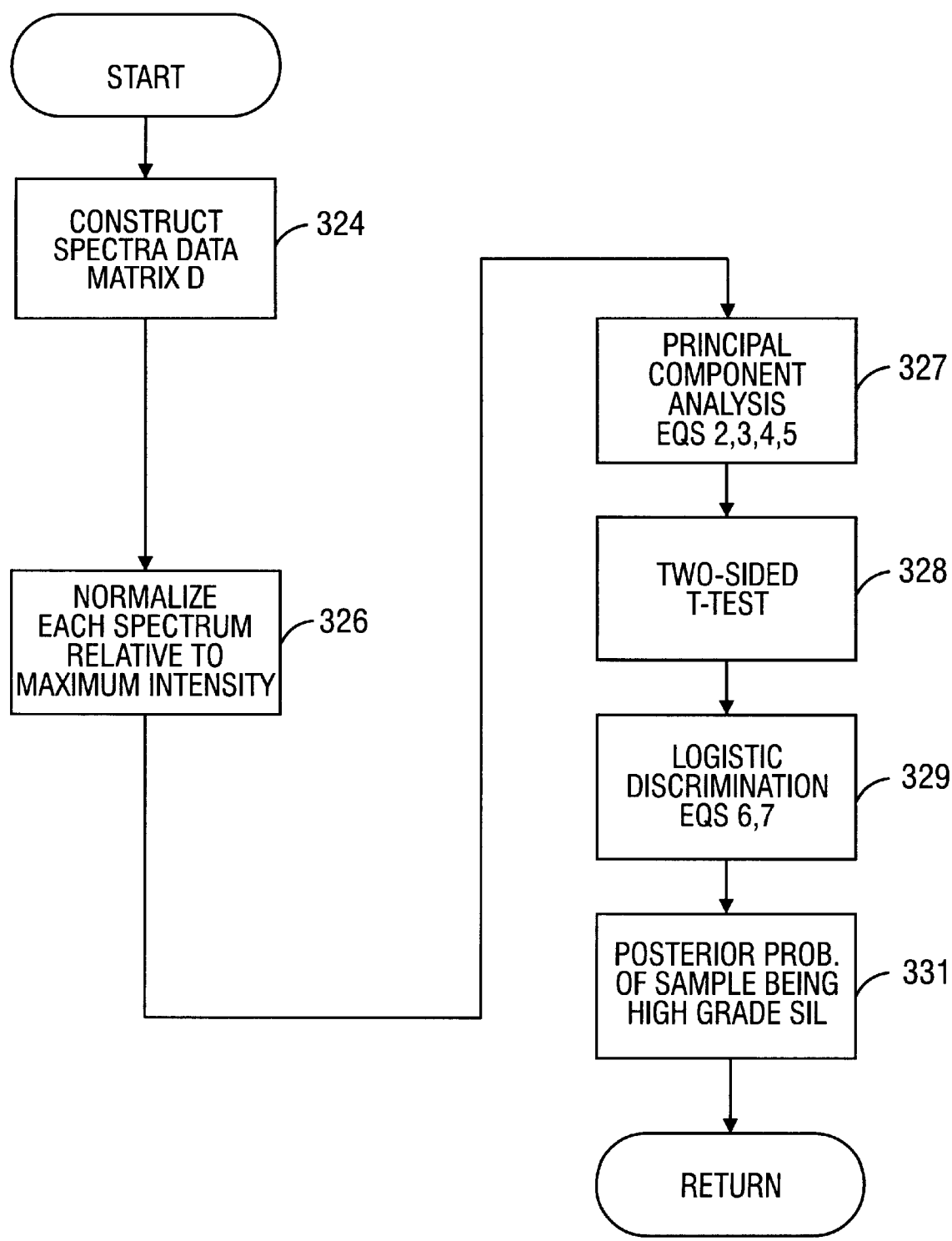

FIGS. 3A–3C are flowcharts of the above-described fluorescence spectroscopy diagnostic methods. In practice, the flowcharts of FIGS. 3A–3C are coded into appropriate form and are loaded into the program memory of computer 119 (FIG. 1) which then controls the apparatus of FIG. 1 to cause the performance of the diagnostic method of the present invention.

Referring first to FIG. 3A, control begin in block 300 where fluorescence spectra are obtained from the patient at 337, 380 and 460 nm excitation. Control then passes to block 301 where the probability of the tissue sample under consideration being SIL is calculated from the spectra obtained from the patient at 337 or 460 nm. This method is shown in more detail with reference to FIG. 3B.

Control then passes to decision block 302 where the probability of SIL calculated in block 301 is compared against a threshold of 0.5. If the probability is not greater than 0.5, control passes to block 303 where the tissue sample is diagnosed normal, and the routine is ended. On the other hand, if the probability calculated in block 301 is greater than 0.5, control passes to block 304 where the probability of the tissue containing SIL is calculated based upon the emission spectra obtained from excitation at 380 nm. This method is identical to the method used to calculate probability of SIL from fluorescence spectra due to 337 or 460 nm, and is also presented below in more detail with reference to FIG. 3B.

Control then passes to decision block 306 where the probability of SIL calculated in block 304 is compared against a threshold of 0.5. If the probability calculated in block 304 is not greater than 0.5, control passes to block 307 where normal tissue is diagnosed and the routine is ended. Otherwise, if decision block 306 determines that the probability calculated in block 304 is greater than 0.5, control passes to block 308 where the probability of high grade SIL is calculated from the fluorescence emission spectra obtained from a 460 nm excitation. This method is discussed below in greater detail with reference to FIG. 3C.

Control then passes to decision block 309 where the probability of high grade SIL calculated in block 308 is compared with a threshold of 0.5. If the probability calculated in block 308 is not greater than 0.5, low grade SIL is diagnosed (block 311), otherwise high grade SIL is diagnosed (block 312).

Referring now to FIG. 3B, the conditioning of the fluorescence spectra by blocks 301 and 304 is presented in more detail. It should be noted that while the processing of block 301 and 304 is identical, block 301 operates on spectra obtained from a 337 or 460 nm excitation, whereas block 304 operates on spectra obtain from a 380 nm excitation. In either case, control begins in block 315 where the fluorescence spectra data matrix, D, is constructed, each row of which corresponds to a sample fluorescence spectrum taken from the patient. Control then passes to block 316 where the mean intensity at each emission wavelength of the detected fluorescence spectra is calculated. Then, in block 317, each spectrum of the data matrix is normalized relative to a maximum of each spectrum. Then, in block 318, each spectrum of the data matrix is mean scaled relative the mean calculated in block 316. The output of block 318 is a preprocessed data matrix, comprising preprocessed spectra for the patient under examination.

Control then passes to block 319 where principal component analysis is conducted, as discussed above, with reference to equations 2, 3, 4 and 5. During principal component analysis, the covariance matrix Z (equation (2)), is calculated using a preprocessed data matrix, the rows of which comprise normalized, mean scaled spectra obtained from all patients, including the patient presently under consideration. The result of block 319 is applied to block 321 where a two-sided Student's T-test is conducted, which results in selection of only diagnostic principal components. Control then passes to block 322 where logistic discrimination is conducted, which was discussed above with reference to equations 6 and 7.

The quantity calculated by block 322 is the posterior probability of the sample belonging to the SIL category (block 323).

Referring now to FIG. 3C, presented are the details of the determination of the probability of high grade SIL from excitation at 460 nm (block 308, FIG. 3A). Control begins in block 324 where the fluorescence spectra data matrix, D, is constructed, each row of which corresponds to a sample fluorescence spectrum taken from the patient. Control then passes to block 326 where each spectrum of the data matrix is normalized relative to a maximum of each spectrum. The output of block 326 is a preprocessed data matrix, comprising preprocessed spectra for the patient under examination. It should be noted that, in contrast to the preprocessing performed in the SIL probability calculating routine of FIG. 3B, there is no mean scaling performed when calculating the probability of high grade SIL.

Control then passes to block 327 where principal component analysis is conducted, as discussed above, with reference to equations 2, 3, 4 and 5. During principal component analysis, the covariance matrix Z (equation (2)), is calculated using a preprocessed data matrix, the rows of which comprise normalized, mean scaled spectra obtained from all patients, including the patient presently under consideration. The result of block 327 is applied to block 328 where a two-sided Student's T-test is conducted, which results in selection of only diagnostic principal components. Control then passes to block 329 where logistic discrimination is conducted, which was discussed above with reference to equations 6 and 7.

The quantity calculated by block 329 is the posterior probability of the sample belonging to the high grade SIL category (block 331).

2. Raman Spectroscopy Diagnostic Method

To illustrate the efficacy of the present invention, twenty colposcopically normal and twenty colposcopically abnormal samples were studied. Two sample pairs were discarded due to experimental errors. Histologically, there were 19 normal, 2 metaplasia, 4 inflammation, 2 HPV and 9 dysplasia samples (2 mild and 7 moderate to severe dysplasias). For the purposes of this study the samples are classified as follows: normal, metaplasia, inflammation, low grade SIL and high grade SIL. Two types of differentiation are of interest clinically: (1) SILs from all other tissues and (2) high grade SILs from low grade SILs. The diagnostic methods developed using fluorescence and Raman spectroscopy are targeted towards achieving optimal sensitivity in this differentiation.

Figure 13:
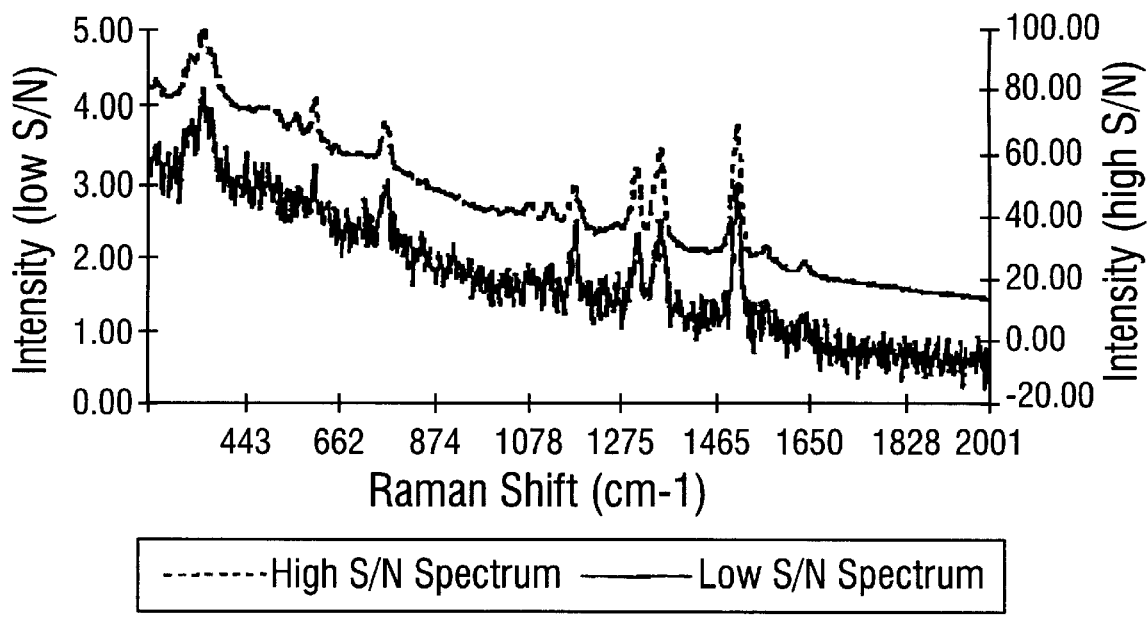
FIG. 13 is a graph depicting measured rhodamine Raman spectra with high and low signal to noise ratios.

Near infrared spectra of cervical tissues were obtained using the system shown in FIG. 2. These spectra are distorted by noise and autofluorescence and are preferably processed to yield the tissue vibrational spectrum. Rhodamine 6G powder packed in a quartz cuvette was used for calibration purposes since it has well documented Raman and fluorescent properties. A rhodamine spectrum with high signal to noise ratio was obtained using a 20 second integration time and a rhodamine spectrum with low signal to noise ratio was obtained using 1 second integration FIG. 13 is a graph showing measured rhodamine spectra with high and low S/N ratios respectively.

Figure 14:
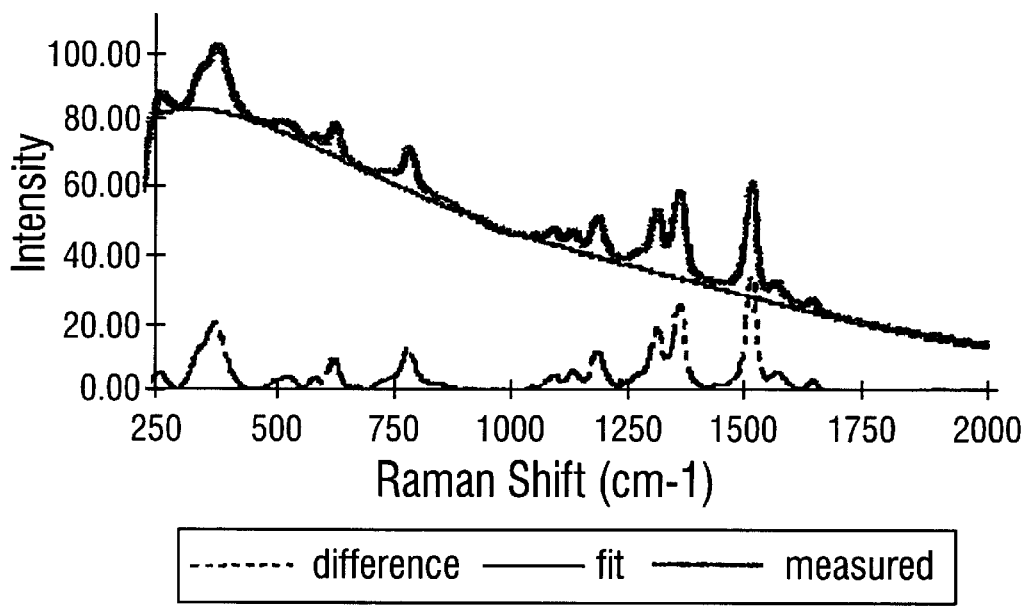
FIG. 14 is a graph depicting the elimination of fluorescence from a Raman spectrum, using a polynomial fit.

The observed noise in the spectra was established to be approximately gaussian. This implies that the use of simple filtering techniques would be effective in smoothing the curves. Using a moving average window on median filter yields acceptable results. However, optimal results are obtained when the spectrum is convolved with a gaussian whose full width half maximum equals the resolution of the system. This technique discards any signal with bandwidth less than the resolution of the system. The filtered scattering signal is still distorted by the residual fluorescence. A simple but accurate method to eliminate this fluorescence is to fit the spectrum containing both Raman and fluorescence information to a polynomial of high enough order to capture the fluorescence line shape but not the higher frequency Raman signal. A 5th degree polynomial was used. The polynomial was then subtracted from the spectrum to yield the Raman signal alone. In FIG. 14, the efficiency of eliminating fluorescence from a Raman signal using a polynomial fit is illustrated.

Figure 15:
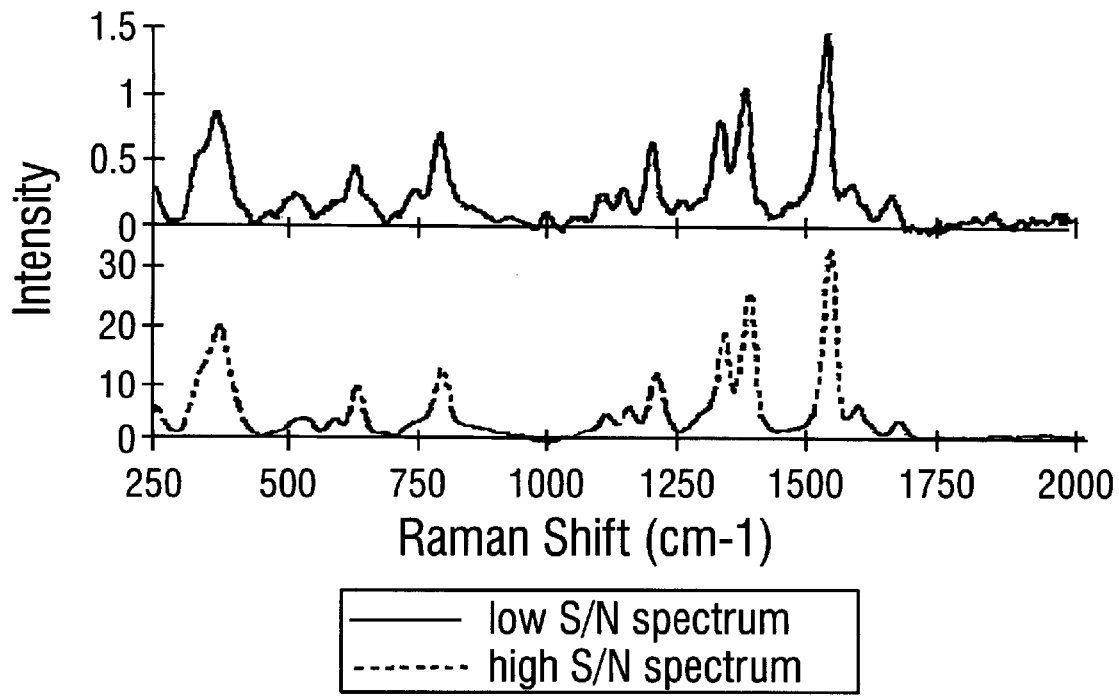
FIG. 15 is a graph comparing low and high signal to noise ratio rhodamine Raman spectra.

FIG. 15 is a graph showing that the processed low S/N rhodamine spectrum is similar to the high S/N rhodamine spectrum and is not distorted by the filtering process. Referring to FIG. 15, in comparison, it can be seen at that the initially noisy spectrum of the low S/N rhodamine once processed show the same principle and secondary peaks at the spectrum of high S/N rhodamine. This validates the signal processing techniques used and indicates that the technique does not distort the resultant spectrum. Each tissue spectrum was thus processed. Peak intensities of relevant bands from these spectra were measured and used for diagnosis.

Figure 16:
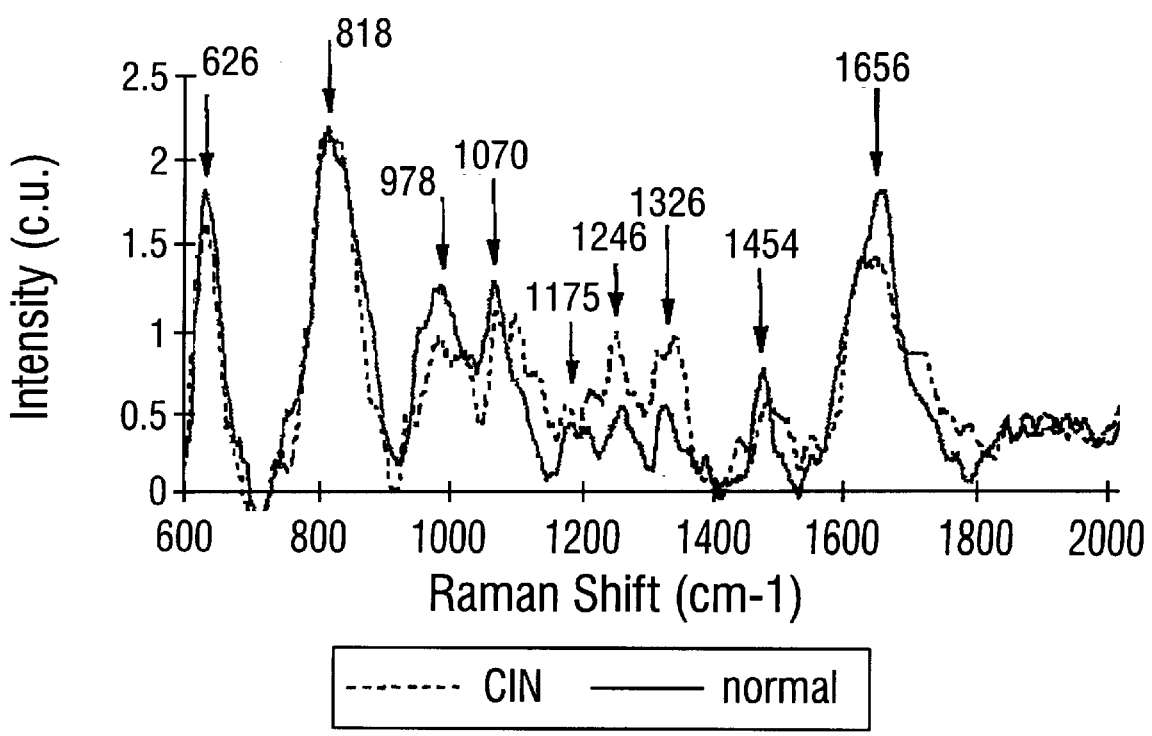
FIG. 16 is a graph depicting a typical pair of Raman spectra obtained from a patient with dysplasia.
Figure 17:
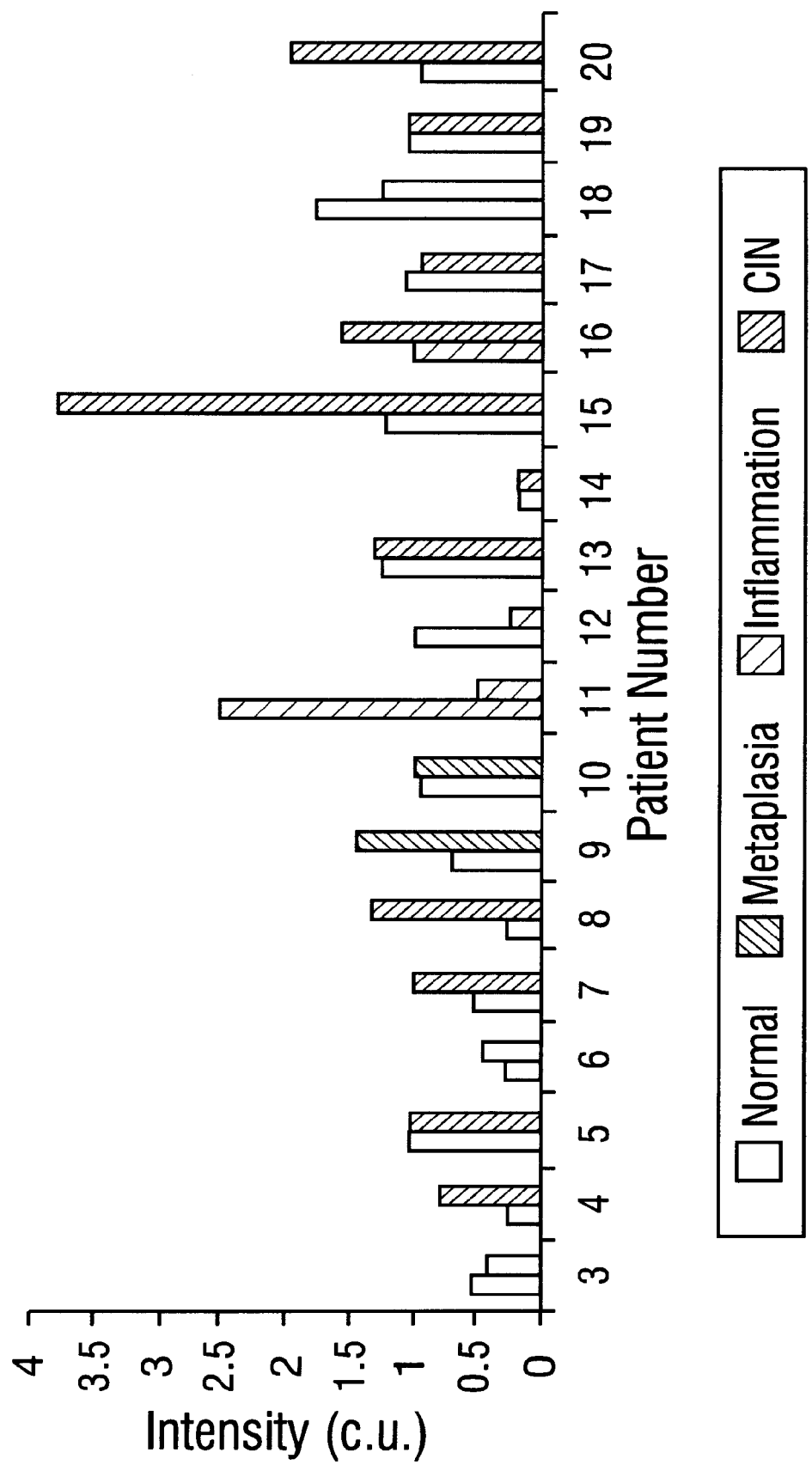
FIG. 17 is a histogram of the Raman band at 1325 $cm^1$ illustrating patient to patient variation.

Typical processed spectra for a pair of normal and abnormal samples from the same patient are shown in FIG. 16 which is a graph of a typical pair of processed spectra from a patient with dysplasia showing the different peaks observed. Several peaks are observed at 626, 818, 978, 1070, 1175, 1246, 1325, 1454 and 1656 cm$^{-1}$ (±11 cm$^{-1}$). Several of the peaks observed have been cited in studies on gynecologic tissues by other groups such as Lui et al., "Fluorescence and Time-Resolved Light Scattering as Optical Diagnostic Techniques to Separate Diseased and Normal Biomedical Media", *J Photochem Photobiol B: Biol,* 16, 187–209, 1992, on colon tissues, and in IR absorption studies on cervical cells by Wong et al., "Infrared Spectroscopy of Human Cervical Cells: Evidence of Extensive Structural Changes during Carcinogenesis", *Proc Natl Acad Sci USA,* 88, 10988–10992, 1991. FIG. 17 is a graph of the intensity of the band at 1325 cm$^{-1}$ for all biopsies to illustrate the patient to patient variation in the intensities of the Raman bands. The intensity of the various Raman bands show a significant patient to patient variability. In FIG. 17, the samples are plotted as pairs from each patient. To account for this patient to patient variability, each peak in a spectrum was normalized to the corresponding peak of the colposcopic and histologic normal sample from the same patient. Thus all colposcopic normal samples that are histologically normal have a peak intensity of one. Normalized and unnormalized spectra were analyzed for diagnostic information.

Each of the bands observed contains some diagnostic information and can differentiate between tissue types with varying accuracy. Clinically, the separation of SILs from all other tissues and high grade SILs from low grade SILs is of interest. Because of the patient to patient variability more significant differentiation was obtained using paired analysis. The bands at 626, 1070 and 1656 cm$^{-1}$ can each differentiate SILs from all other tissues. At all three bands, the intensity of the normal is greater than the intensity of the SIL. This is illustrated in FIGS. 18 and 19.

Figure 18A:
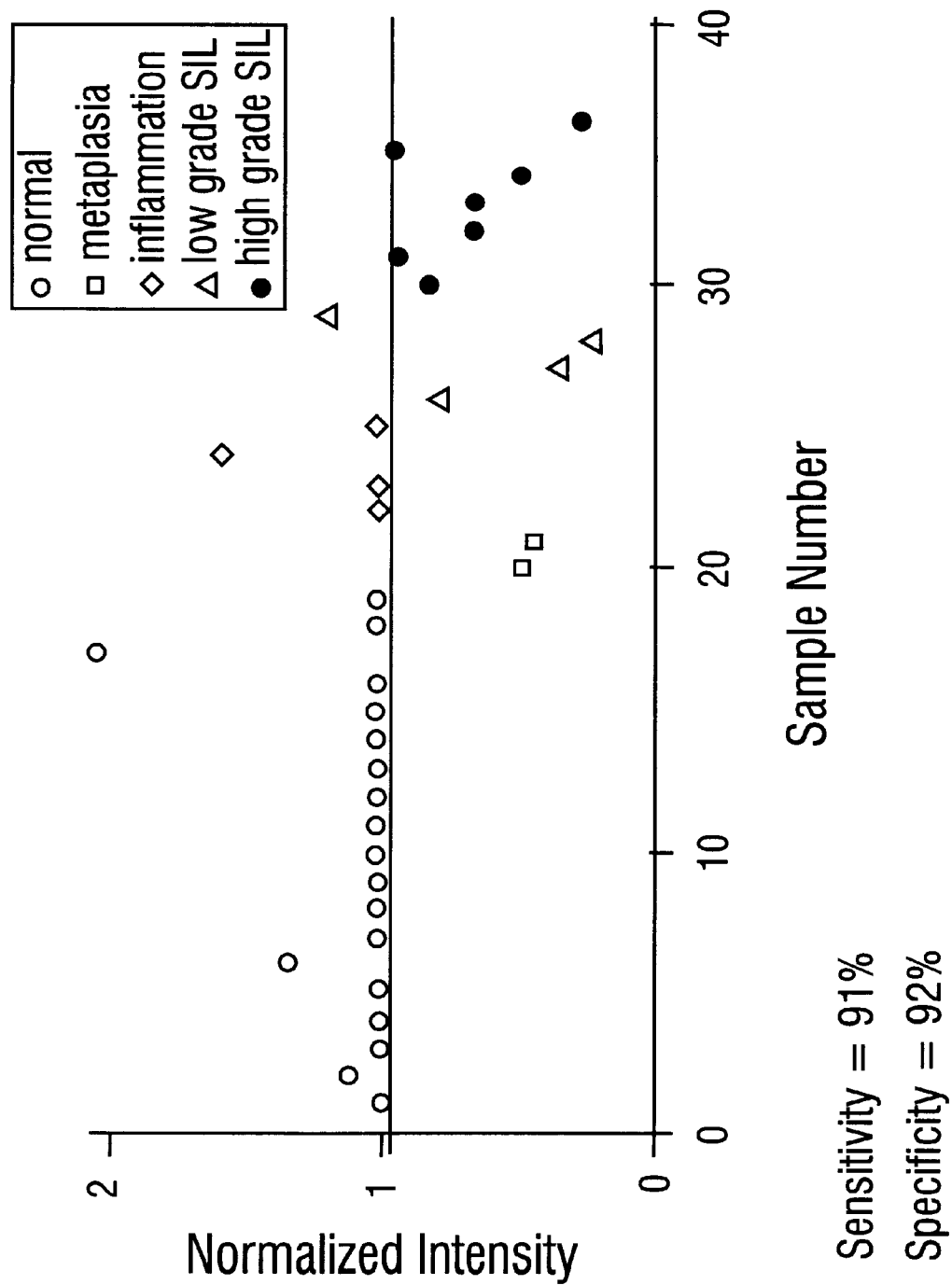
FIGS. 18A and 18B are graphs illustrating the diagnostic capability of the Raman spectroscopy diagnostic method of the present invention.
Figure 18B:
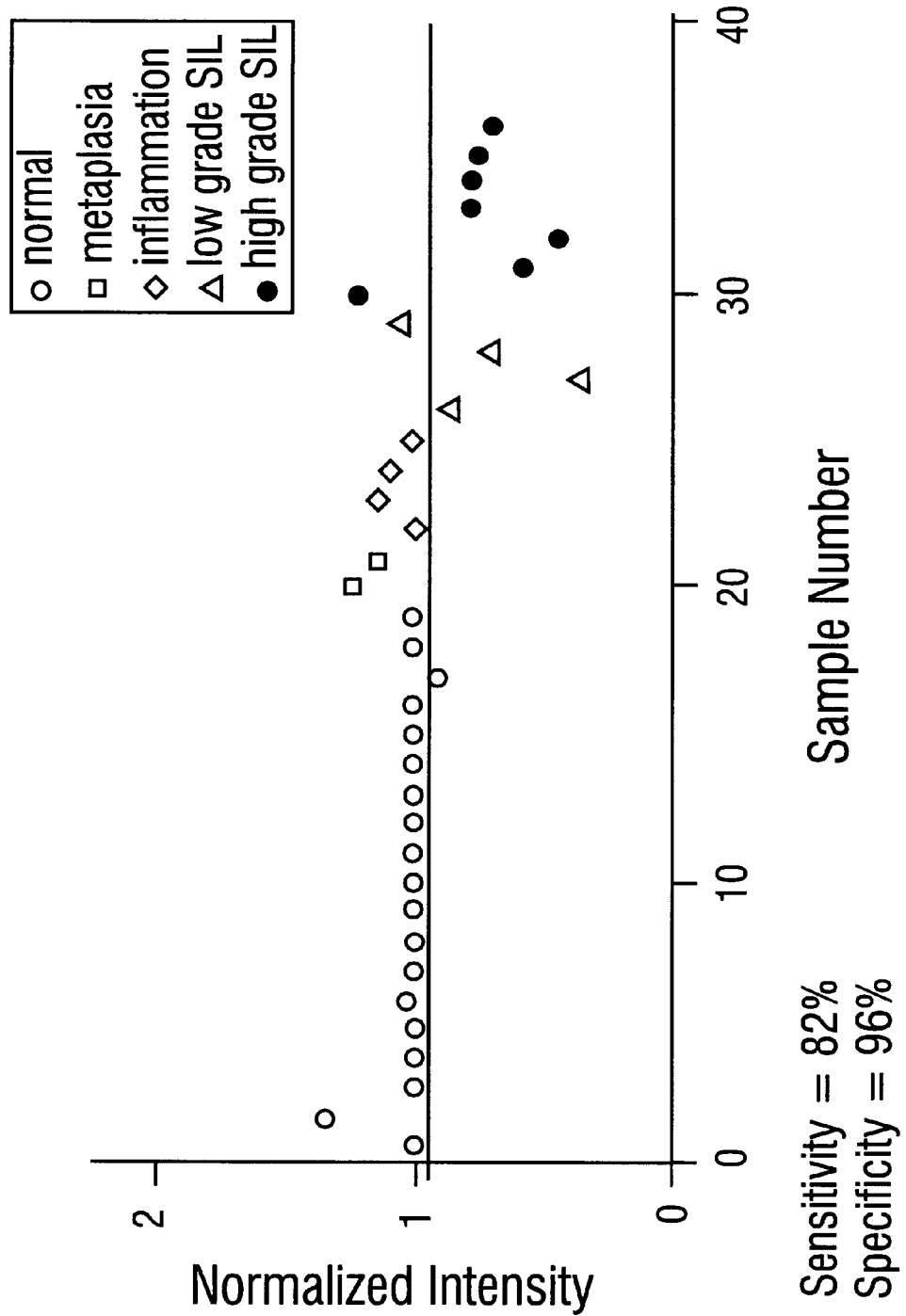

FIGS. 18A and 18B are graphs showing diagnostic capability of normalized peak intensity of Raman bands at 626 cm$^{-1}$, and 1070 cm$^{-1}$, respectively. The band at 626 cm$^{-1}$ which is due to ring deformations differentiates SILs from all other tissues with a sensitivity and specificity of 91% and 92% (FIG. 18A). One SIL sample (focal HPV) is misclassified. The metaplasia samples are incorrectly classified as SILs at this band. However, using the intensity at the C-O stretching and bending vibrational band of about 1070 cm$^{-1}$ for a similar classification, all metaplasia and inflammation samples are correctly classified as non-SILs (FIG. 18B). Of the two samples incorrectly classified, it was determined that one has focal dysplasia and the other is the same sample with focal HPV that was misclassified at 626 cm$^{-1}$. Only one normal sample is misclassified as SIL. A sensitivity and specificity of 82% and 96% is achieved. This band has been attributed to glycogen and cellular lipids/phosphate by Wong et al., "Infrared Spectroscopy of Human Cervical Cells: Evidence of Extensive Structural Changes during Carcinogenesis," *Proc Natl Acad Sci USA*, 88, 10988–10992, 1991.

Figure 19:
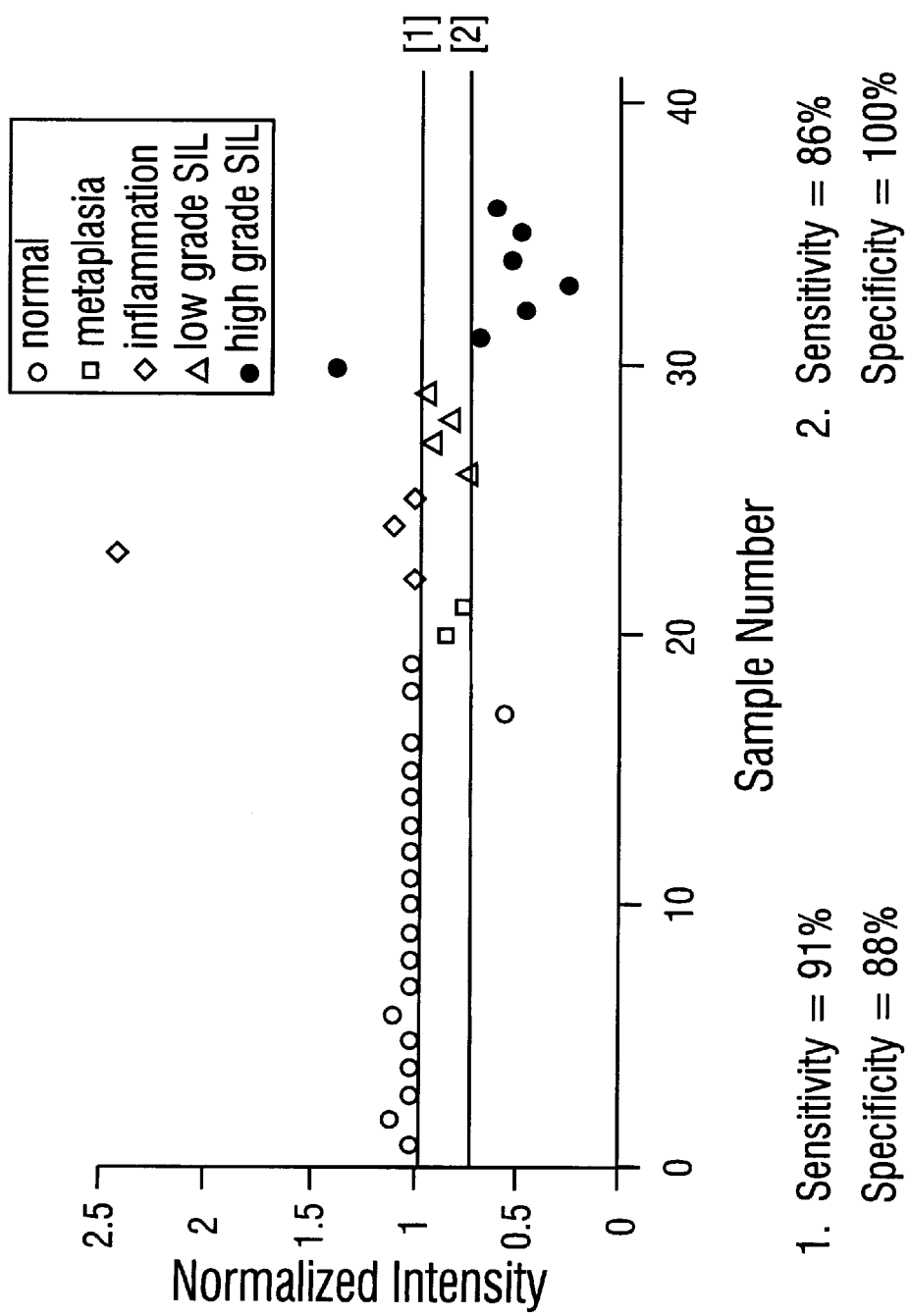
FIG. 19 is another graph depicting the diagnostic capability of the Raman spectroscopy diagnostic method of the present invention.

FIG. 19 is a graph showing the diagnostic capability of the band at 1656 cm$^{-1}$. Decision line (1) separates SILs from all other tissues. Decision line (2) separates high grade from low grade SILs. The normalized peak intensity at 1656 cm$^{-1}$ can differentiate SILs from other tissues using line (1) as the decision line with a sensitivity and specificity of 91% and 88%. The focal dysplasia sample incorrectly classified at 1070 cm$^{-1}$ is again misclassified. The metaplastic samples are again classified as SILs. The advantage of using this peak is that it can also differentiate between high grade and low grade SILs. Using line (2) as a decision line, this peak can separate high and low grade SILs with a sensitivity of 86%. The metaplasia samples misclassified as SILs are separated from the high grade samples. Only one normal sample is misclassified. In the cervix, this peak has been associated with cellular proteins from the nuclei of the epithelial cells. These proteins have been suggested to be primarily collagen and elastin by Lui et al., "Fluorescence and Time-Resolved Light Scattering as Optical Diagnostic Techniques to Separate Diseased and Normal Biomedical Media," *J Photochem Photobiol B: Biol*, 16, 187–209, 1992.

Of the other features observed in the Raman spectra of cervical tissues, the band at 818 cm$^{-1}$ is associated with ring 'breathing' and is attributed to blood. The intensity of this band is greater in dysplasia samples relative to respect to normal samples. The peak at 978 cm$^{-1}$ is associated with phosphorylated proteins and nucleic acids. This band differentiates SILs from other tissues with a sensitivity and specificity of 82% and 80%. The band at 1175 cm$^{-1}$ can separate normal from dysplasia samples with a sensitivity of 88%. The decrease in intensity of this band with dysplasia has been reported by Wong et al., "Infrared Spectroscopy of Human Cervical Cells: Evidence of Extensive Structural Changes during Carcinogenesis", *Proc Natl Acad Sci USA*, 88, 10988–10992, 1991, as well. This band around 1175 cm$^{-1}$ has been associated with C-O stretching and in cervical cells, this band consists of three overlapping lines at 1153, 1161 and 1172 cm$^{-1}$. A similar trend is also observed in cervical tissue samples. These bands have been attributed to C-O stretching of cell proteins such as tyrosine and carbohydrates. The Raman line at 1246 cm$^{-1}$ is assigned to the stretching vibrations of C-N (amide III). The line at 1325 cm$^{-1}$ is due to ring vibrations and is associated with tryptophan by Lui et al., "Fluorescence and Time-Resolved Light Scattering as Optical Diagnostic Techniques to Separate Diseased and Normal Biomedical Media", *J Photochem Photobiol B: Biol*, 16, 187–209, 1992, and nucleic acids. An increase in the intensity of this peak in the SILs with respect to the other tissues is observed. This has been associated with increased cellular nuclear content in the colon. The lines at 1401 and 1454 cm$^{-1}$ are due to symmetric and asymmetric $CH_3$ bending modes of proteins (methyl group). The line at 1454 cm$^{-1}$ differentiates high grade from low grade SILs with a 91% accuracy. These lines have been associated with elastin and collagen by Lui et al., "Fluorescence and Time-Resolved Light Scattering as Optical Diagnostic Techniques to Separate Diseased and Normal Biomedical Media", *J Photochem Photobiol B: Biol*, 16, 187–209, 1992.

Analyzing the diagnostic information from the tissue Raman spectra in a paired manner, SILs may be differentiated from all other tissues at several peaks with an average sensitivity of 88% (±6%) and a specificity 92% (±7%). The best sensitivity is achieved at 91% with the bands at 626 and 1656 cm$^{-1}$. The best specificity is achieved at 100% using a combination of the bands at 1070 and 626 cm$^{-1}$. In differentiating SILs from normals, the sensitivity and specificity of the Raman methods are greater than those of the fluorescence based methods for the 36 samples but are similar when compared to the fluorescence results from the larger sample study. Inflammation and metaplasia samples can be separated from the SILs using the Raman band at 1070 cm$^{-1}$ and at 1656 cm$^{-1}$. Raman spectra are successful in differentiating high grade SILs from low grade SILs with an average sensitivity of 86% (±4%). The sensitivity is improved when compared to fluorescence based diagnosis of the same 36 samples as well as the larger sample population. The invention also accommodates patient to patient variability in the intensities of the Raman lines by use of paired analysis as presented above. In addition, unpaired differentiation may be done by using the peaks at 1325, 1454 and 1656 cm$^{-1}$ with a comparable sensitivity.

Figure 20:
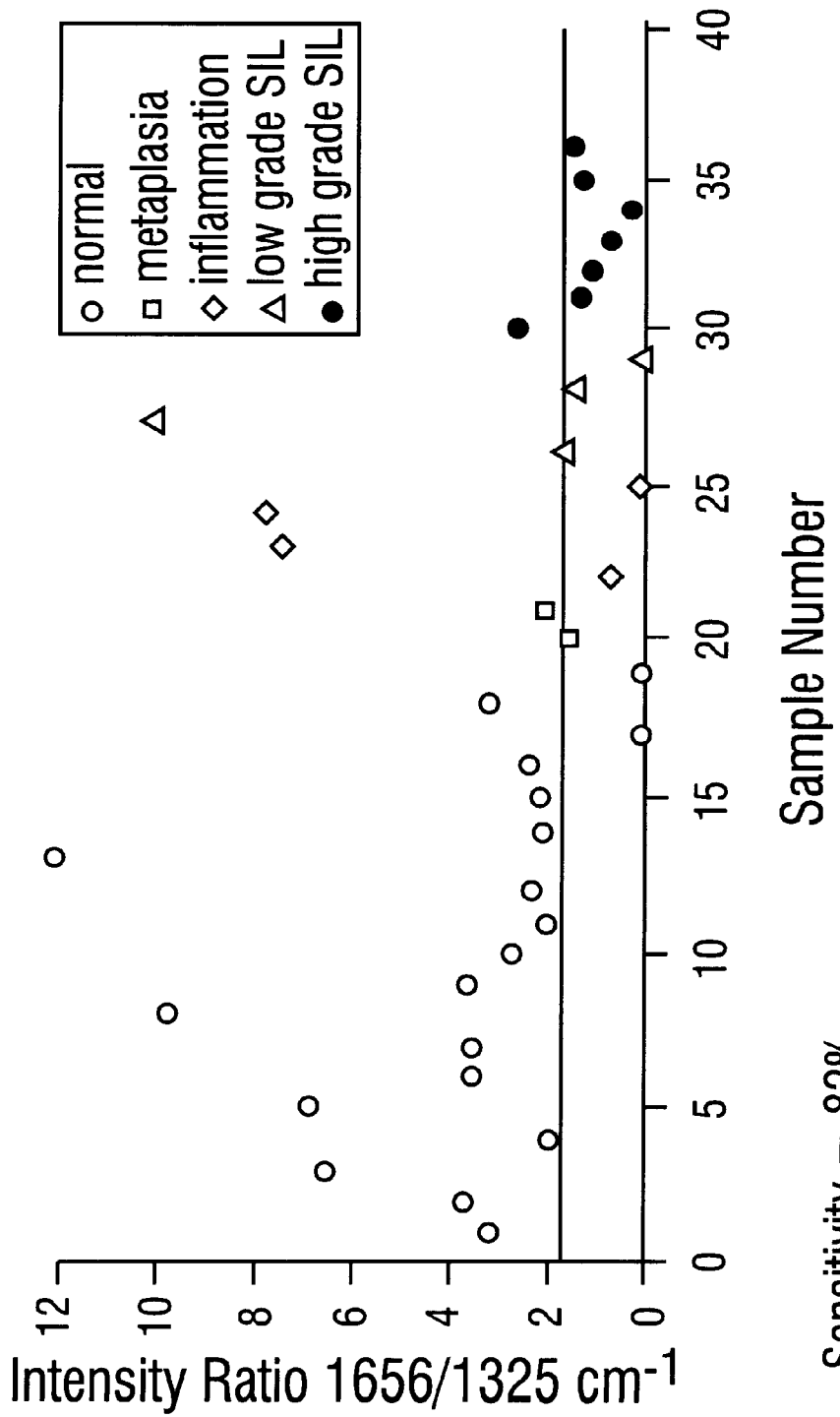
FIGS. 20 and 21 are graphs illustrating the diagnostic capability of the Raman spectroscopy diagnostic method of the present invention.
Figure 21:
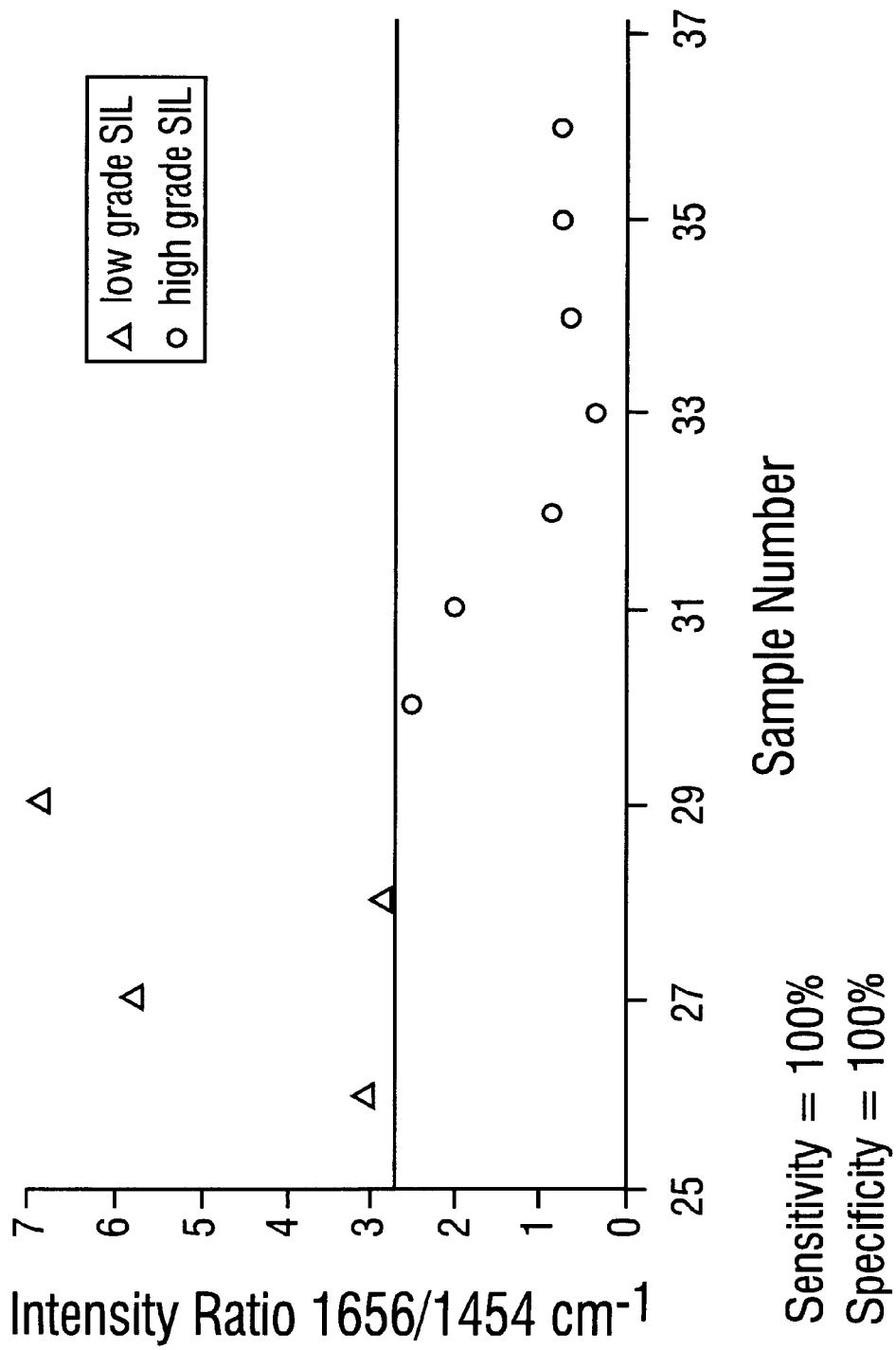

For unpaired differentiation, the ratio of intensities at 1656 and 1325 cm$^{-1}$ differentiate SILs from all other tissues with a sensitivity and a specificity of 82% and 80%, respectively (FIG. 20). In addition, the ratio of the intensities at 1656 and 1454 cm$^{-1}$ may be used in an unpaired manner to differentiate high grade SILs from low grade SILs with a sensitivity and specificity of 100% and 100% (FIG. 21).

Further, as mentioned above, each of these specified peaks of the Raman spectrum contain some diagnostic information for tissue differentiation. Multivariate techniques using principal component analysis and Baye's theorem, similar to the conditioning of the fluorescence spectra described above, would use information from all of the peaks of the Raman spectrum, and would thus improve the diagnostic performance of the Raman signals. The methods using Raman signals presented here have been optimized for the 36 sample data set and are thus a bias estimate of their performance. A true estimate of the diagnostic capability of Raman spectroscopy would require an unbiased assessment of the performance of the method which for the small number of samples could be obtained using cross validation techniques, or other types of validation techniques.

The present invention exploits several potential advantages of Raman spectroscopy over fluorescence. The Raman diagnostic methods used in the invention reiterate the simplicity of Raman spectroscopy for diagnosis and indicate the potential of improved diagnostic capability using this technique.

FIGS. 4A–4D are flowcharts of the above-described Raman spectroscopy diagnostic method. In practice, the flowcharts of FIGS. 4A–4D are coded into appropriate form and are loaded into the program memory of computer 211 (FIG. 2) which then controls the apparatus of FIG. 2 to cause the performance of the Raman spectroscopy diagnostic method of the present invention.

Figure 4A:
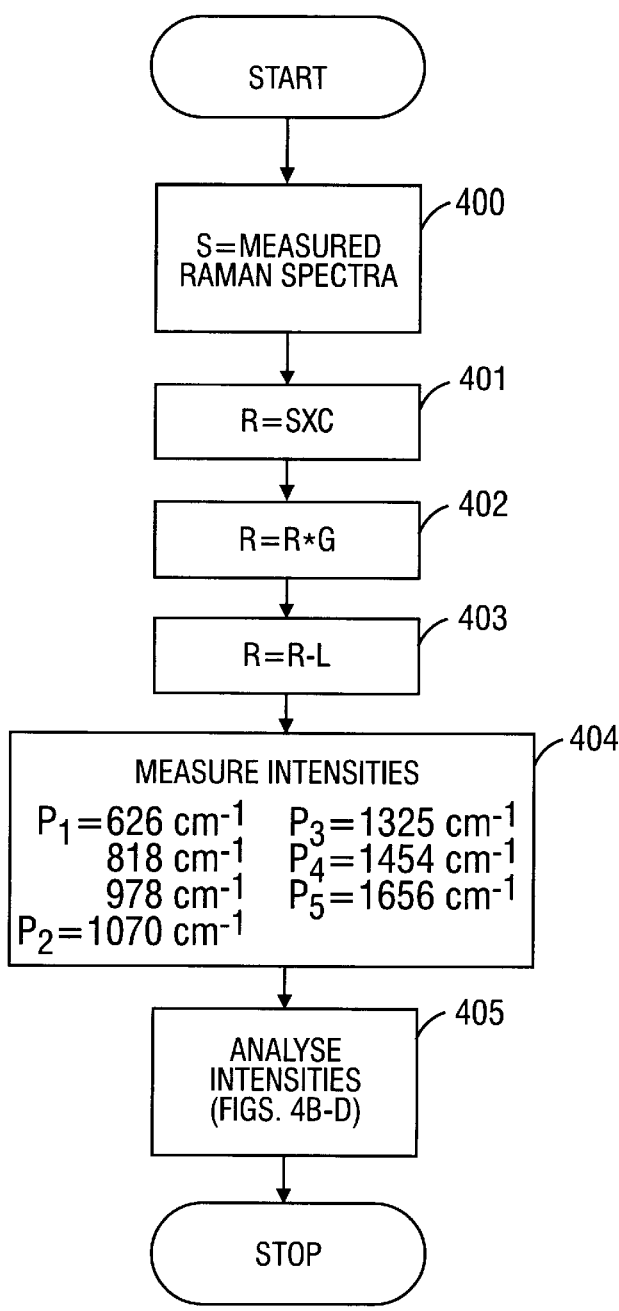
FIGS. 4A–4D are flowcharts of an exemplary Raman spectroscopy diagnostic method, in accordance with the present invention.

Referring first to FIG. 4A, after the method is started, the NIR Raman spectrum is acquired from the cervical tissue sample of unknown diagnosis in step 400. Then, in step 401, the acquired spectrum is corrected as a function of the rhodamine calibration process. Then, in block 402, the spectrum is convolved with a gaussian G having a full width half maximum of 11 wavenumbers, thus providing a corrected noise spectrum R. In step 403, the broad band baseline of the noise corrected spectrum is fit to a polynomial L, and the polynomial is subtracted from the spectrum to give the Raman signal for the sample under consideration.

Control then passes to step 404 where the maximum intensities at 626, 818, 978, 1070, 1175, 1246, 1325, 1454 and 1656 wavenumbers (in units of $cm^{-1}$) are noted. Also in block 404, maximum intensities at five selected wavenumbers are stored. These include:

$P_1$=intensity at 626 $cm^{-1}$
$P_2$=intensity at 1070 $cm^{-1}$
$P_3$=intensity at 1325 $cm^{-1}$
$P_4$=intensity at 1454 $cm^{-1}$
$P_5$=intensity at 1656 $cm^{-1}$ Control then passes to block 405 where the stored intensities are analyzed in order to diagnose the tissue sample. This analysis is presented below in more detail with reference to FIGS. 4B–D.

Figure 4B:
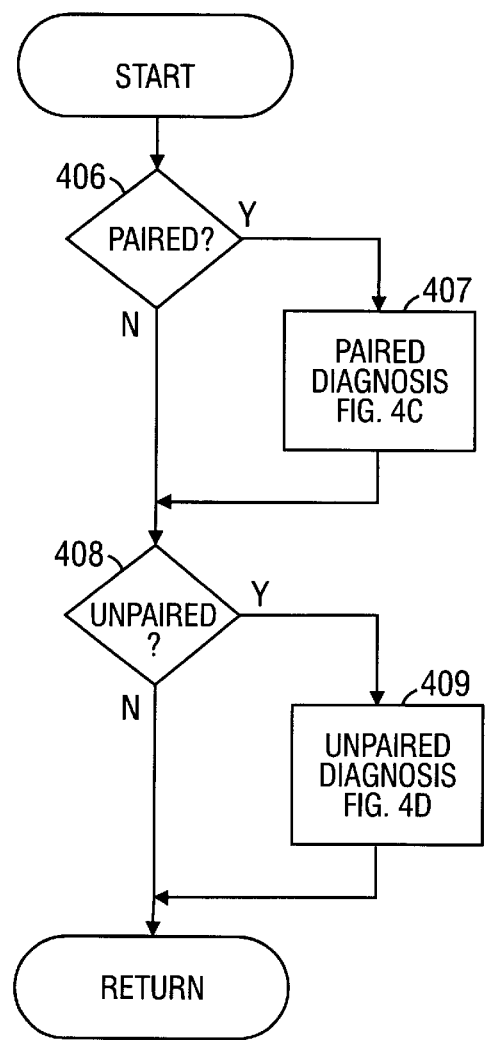

Referring to FIG. 4B, decision block 406 determines whether paired analysis is desired, and if so control passes to block 407 where the paired diagnostic method is conducted. This is presented below in more detail with reference to FIG. 4C.

Control then passes to decision block 408 where it determined whether unpaired analysis is desired. If so, control passes to block 409 where the unpaired diagnostic method is conducted.

Figure 4C:
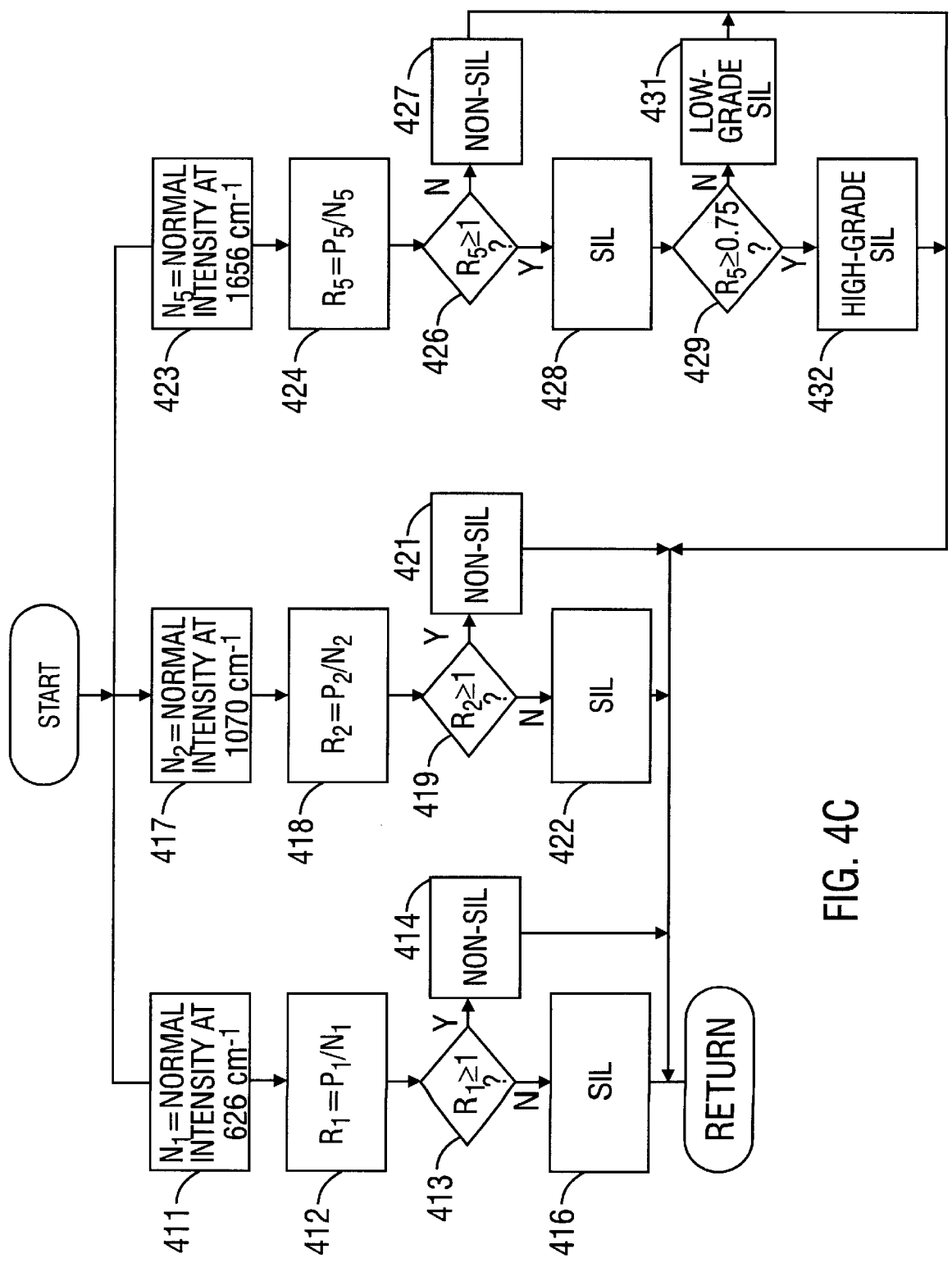

Referring to the paired diagnostic method, presented with reference to FIG. 4C, three parallel analyses may be conducted, one with respect to intensity $P_1$, one with respect to intensity $P_2$, and one with respect to intensity $P_5$. For intensity $P_1$, control begins in block 411 where quantity $N_1$ is set equal to the intensity at the selected wavenumber for a normal tissue sample of the patient under consideration. Control then passes to block 412 where the ratio between measured intensity $P_1$ and normal intensity $N_1$ is calculated.

In block 413, the ratio is compared with a threshold of 1. If the ratio is greater than or equal to 1, the diagnosis is non-SIL (step 414), whereas if the ratio is less than 1, the diagnosis is SIL (step 416).

A similar analysis is conducted with respect to intensities $P_2$ and $P_5$. Specifically, for intensity $P_2$, control begins in block 417 where quantity $N_2$ is set equal to the intensity at the selected wavenumber for a normal tissue sample of the patient under consideration. Control then passes to block 418 where the ratio between measured intensity $P_2$ and normal intensity $N_2$ is calculated. In block 419, the ratio is compared with a threshold of 1. If the ratio is greater than or equal to 1, the diagnosis is non-SIL (step 421), whereas if the ratio is less than 1, the diagnosis is SIL (step 422).

For intensity $P_5$, control begins in block 423 where quantity $N_5$ is set equal to the intensity at the selected wavenumber for a normal tissue sample of the patient under consideration. Control then passes to block 424 where the ratio between measured intensity $P_5$ and normal intensity $N_5$ is calculated. In block 426, the ratio is compared with a threshold of 1. If the ratio is greater than or equal to 1, the diagnosis is non-SIL (step 427), whereas if the ratio is less than 1, the diagnosis is SIL (step 428).

If SIL is concluded in step 428, control passes to decision block 429 where the ratio calculated in block 424 is compared against a threshold of 0.75. If the ratio is greater than or equal to 0.75, then low grade SIL is diagnosed (step 431), whereas if the ratio is less than 0.75, high grade SIL is diagnosed (step 432).

Figure 4D:
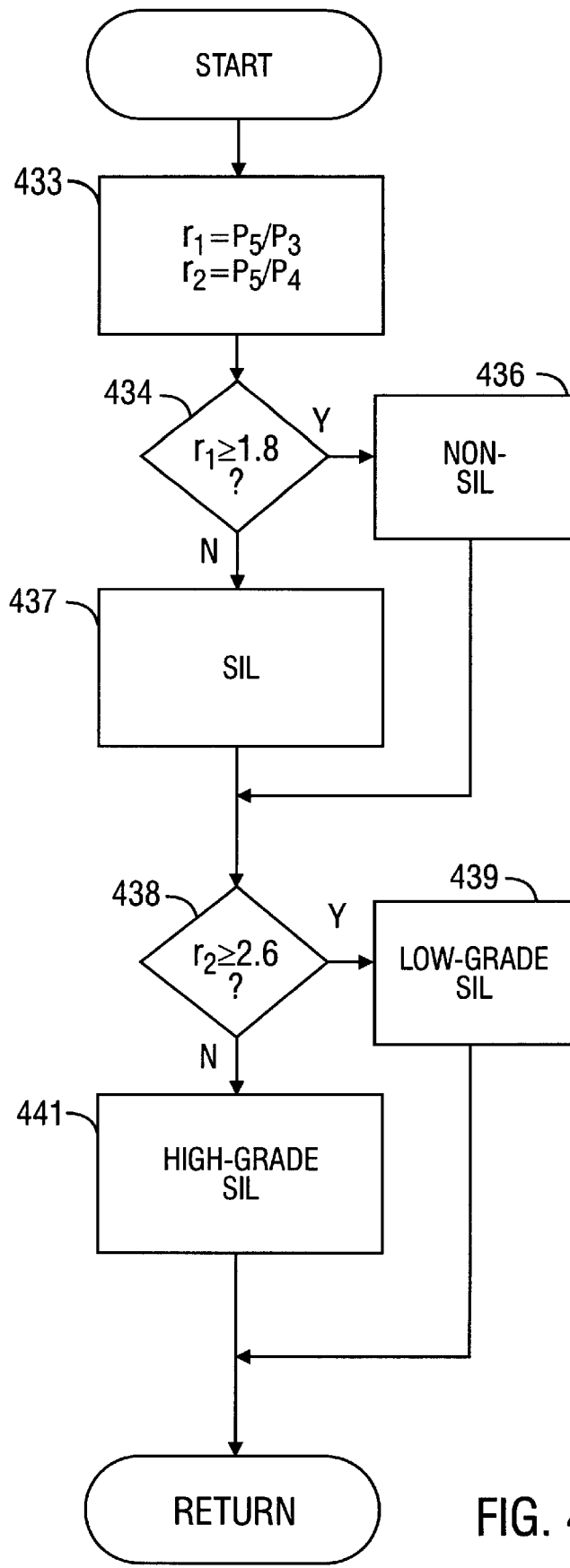

Unpaired analysis of the NIR Raman spectrum is presented in FIG. 4D. Beginning in step 432, ratio $r_1$ is calculated between intensity $P_5$ and intensity $P_3$, and ratio $r_2$ is calculated between intensity $P_5$ and intensity $P_4$. Control then passes to decision block 434 where ratio $r_1$ is compared against a threshold of 1.8. If ratio $r_1$ is greater than or equal to 1.8, the tissue sample is diagnosed as non-SIL (step 436), whereas if ratio $r_1$ is less than 1.8, the tissue is diagnosed as SIL (step 437). Control then passes to decision block 438 where ratio $r_2$ is compared against the threshold of 2.6. If ratio $r_2$ is greater than or equal to 2.6, low grade SIL is diagnosed (step 439), whereas ratio $r_2$ is less than 2.6, high grade SIL is diagnosed (step 441).

It should be noted that the various thresholds used for the decision blocks in FIGS. 4C and 4D may be adjusted without departing from the scope of the invention. The thresholds presented were chosen as a function of the training data, and other or more complete training data may result in different thresholds.

3. Combined Fluorescence and Raman Spectroscopy Method

The present invention also contemplates a system that sequentially acquires fluorescence and NIR Raman spectra in vivo through an optical probe, such as a fiber optic probe or other optical coupling system. The optical probe is selectively coupled to ultraviolet or visible sources of electromagnetic radiation to excite fluorescence, and then selectively coupled to NIR sources to excite fluorescence free Raman spectra. The fluorescence spectra may be used to improve the analytical rejection of fluorescence from the Raman spectrum.

The apparatus used for this purpose is a combination of the apparatus disclosed in FIGS. 1 and 2. A dichroic mirror or swing-away mirror is used so that each electromagnetic radiation source is selectively coupled sequentially into the optical probe. Similarly, light collected by the probe is selectively coupled to the appropriate detectors to sense the fluorescence spectra and Raman spectra.

In analyzing the spectra for diagnostic purposes, it is presently contemplated that the above-described ability of fluorescence to identify normal tissue, and low and high grade lesions, be followed by the above-described use of NIR Raman spectra to identify inflammation and metaplasia. Alternatively, information gathered about the tissue type, in accordance with the above-described fluorescence diagnosis, is used to improve the Raman diagnostic capability. This is accomplished by using fluorescence spectra to calculate the posterior probability that a tissue is normal, low or high grade SIL. Then, this classification is used as the prior probability in a Bayesian method, based on the detected Raman spectra. In yet another embodiment, information gathered with NIR Raman spectroscopy is used to calculate the posterior probability that the tissue is inflamed or metaplastic. Then, this information is used as the prior probability in a Bayesian method, based on the detected fluorescence spectrum.

While the present invention has been described with reference to several exemplary embodiments, it will be understood that modifications, additions and deletions may be made to these embodiments without departing from the spirit and scope of the present invention.

APPENDIX I: SPECIFICALLY AND SENSITIVITY

Summarized from: Albert A., Harris E. K.: *Multivariate Interpretation of Clinical Laboratory Data*, Marcel Dekker Inc., New York, pp. 75–82, (1987), the disclosure of which is expressly incorporated herein by reference.

Figure 22:
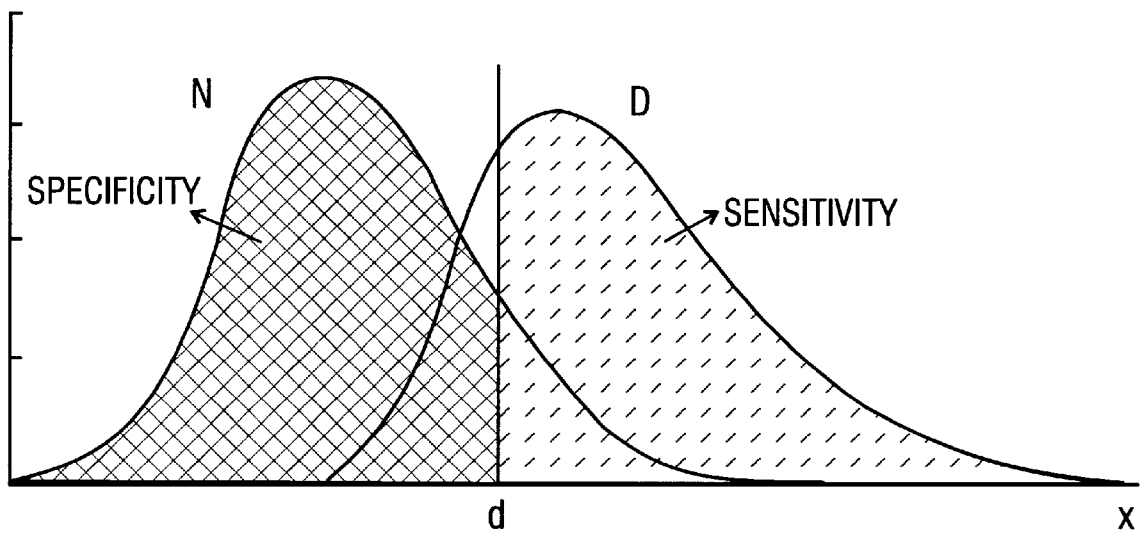
FIG. 22 is a graph of a hypothetical distribution of test values.

Assuming a group of T samples which can be categorized as normal (N samples) or diseased (D samples). A diagnostic test, designed to determine whether the sample is normal or diseased, is applied to each sample. The results of the tests is the continuous variable x, which is then used to determine the sample type. FIG. 22 illustrates a hypothetical distribution of test values for each sample type. A diagnostic method based on this test can easily be defined by choosing a cutoff point, d, such that a sample with an observed value x<d is diagnosed as normal and a sample with an observed value x≦d is diagnosed as abnormal.

Several quantitative measures have been defined to 'evaluate' the performance of this type of method. The first type evaluates the test itself (i.e. measures the ability of the test to separate the two populations, N and D). Sensitivity and specificity are two such measures. The second type is designed to aid in the interpretation of a particular test result (i.e. deciding whether the individual test measurement has come from a normal or diseased sample). Positive and negative predictive value are two measures of this type.

To define these measures, some terminology and notation must be introduced. Referring to Table 6, a sample to be tested can be either normal or diseased; the result of the test for each type of sample can be either negative or positive. True negatives represent those normal with a positive test result. In these cases, the diagnosis based on the rest result is correct. False positives are those normal samples which have a positive test result and false negatives are those diseased samples which have a negative test result. In these cases, the diagnosis based on the test result is incorrect.

TABLE 6

|  | Normal | Diseased | Total Samples |
|---|---|---|---|
| Test Negative (x < d) | True Negatives (TN) | False Negatives (FN) | Negatives (Neg) |

TABLE 6-continued

|  | Normal | Diseased | Total Samples |
|---|---|---|---|
| Test Positive (x ≧ d) | False Positives (FP) | True Positives (TP) | Positives (Pos) |
| Total Samples | N | D | T |

With this terminology, Table 7 contains a definition of sensitivity and specificity, the two measures which assess the performance of the diagnostic method. Specificity is the proportion of normal samples with a negative test result (proportion of normal samples diagnosed correctly). Sensitivity is the proportion of diseased samples with a positive test result (Proportion of diseased samples correctly diagnosed). FIG. 22 also contains a graphical representation of specificity and sensitivity. Specificity represents the area under the normal sample distribution curve to the left of the cut off point while sensitivity represent the area under the diseased sample distribution curve to the right of the cut off point.

TABLE 7

| Test Measure | Meaning | Calculation |
|---|---|---|
| Specificity | Proportion of normal samples with negative test result | Sp = TN/N |
| Sensitivity | Proportion of diseased samples with positive test result | Se = TP/D |

While sensitivity and specificity characterize the performance of a particular method, another set of statistics is required to interpret the laboratory test result for a given specimen. The positive and negative predictive value quantify the meaning of an individual test result (Table 8). The positive predictive value is the probability that if the test result is positive, the sample is diseased. The negative predictive value is the probability that if the test result is negative, the sample is normal. Positive and negative predictive value are calculated from Baye's rule as outlined in Albert and Harris. Table 8 contains two equivalent formulas for calculation positive and negative predictive value.

TABLE 8

| Measure | Meaning | Calculation 1 | Calculation 2 |
|---|---|---|---|
| Positive Predictive Value | The probability that, if the test is positive, the sample is diseased | $PV_+ = TP/Pos$ | $PV_+ = DSe/(DSe + N(1 - Sp))$ |
| Negative Predictive Value | The probability that, if the test is negative, the sample is normal | $PV_- = TN/Neg$ | $PV_- = NSp/(NSp + D(1 - Se))$ |

APPENDIX II: PRINCIPAL COMPONENTS

| 337 nm excitation | | 460 nm excitation | | 380 nm excitation | | 460 nm excitation | |
|---|---|---|---|---|---|---|---|
| E1 | E2 | E1 | E2 | E2 | E6 | E4 | E7 |
| 0.12 | 0.11 | −0.147 | −0.275 | −0.615 | 0.532 | 0.69 | 0.10 |
| 0.17 | 0.12 | −0.093 | −0.319 | −0.464 | 0.151 | 0.09 | −0.07 |
| 0.22 | 0.12 | −0.074 | −0.360 | −0.378 | −0.1 | −0.14 | −0.17 |
| 0.26 | 0.11 | −0.056 | −0.345 | −0.317 | −0.308 | −0.23 | −0.07 |
| 0.27 | 0.1 | −0.027 | −0.314 | −0.236 | −0.373 | −0.24 | 0.06 |
| 0.28 | 0.11 | −0.004 | −0.253 | −0.157 | −0.348 | −0.23 | 0.04 |
| 0.28 | 0.12 | 0.010 | −0.193 | −0.086 | −0.236 | −0.19 | 0.01 |
| 0.28 | 0.12 | 0.024 | −0.121 | −0.04 | −0.161 | −0.15 | 0.00 |
| 0.28 | 0.11 | 0.029 | −0.048 | −0.004 | −0.071 | −0.09 | −0.05 |
| 0.26 | 0.11 | 0.016 | 0.030 | 0.025 | −0.055 | −0.01 | −0.07 |
| 0.24 | 0.11 | −0.001 | 0.097 | 0.044 | 0.013 | 0.06 | −0.07 |
| 0.22 | 0.11 | −0.026 | 0.153 | 0.06 | 0.068 | 0.12 | 0.24 |
| 0.2 | 0.09 | −0.052 | 0.201 | 0.06 | 0.108 | 0.14 | 0.40 |
| 0.17 | 0.08 | −0.025 | 0.203 | 0.055 | 0.123 | 0.16 | 0.30 |
| 0.13 | 0.05 | 0.019 | 0.192 | 0.046 | 0.159 | 0.16 | 0.04 |
| 0.09 | 0.04 | 0.062 | 0.160 | 0.023 | 0.133 | 0.16 | −0.12 |
| 0.06 | 0.04 | 0.090 | 0.153 | 0.006 | 0.15 | 0.14 | −0.18 |
| 0.02 | 0.05 | 0.091 | 0.153 | −0.014 | 0.089 | 0.14 | −0.14 |
| 0.01 | 0.05 | 0.088 | 0.164 | −0.026 | 0.075 | 0.16 | −0.24 |
| −0.04 | 0.05 | 0.087 | 0.158 | −0.044 | 0.047 | 0.17 | −0.23 |
| −0.06 | 0.05 | 0.106 | 0.146 | −0.055 | 0.026 | 0.17 | −0.16 |
| −0.08 | 0.07 | 0.145 | 0.092 | −0.063 | −0.016 | 0.11 | −0.12 |
| −0.09 | 0.09 | 0.199 | 0.020 | −0.071 | −0.089 | 0.05 | −0.18 |
| −0.1 | 0.11 | 0.219 | −0.023 | −0.072 | −0.102 | 0.01 | −0.09 |
| −0.11 | 0.13 | 0.240 | −0.054 | −0.078 | −0.104 | −0.02 | −0.11 |
| −0.11 | 0.15 | 0.249 | −0.060 | −0.071 | −0.078 | −0.04 | 0.04 |
| −0.12 | 0.17 | 0.242 | −0.073 | −0.071 | −0.091 | −0.03 | −0.06 |
| −0.12 | 0.18 | 0.239 | −0.075 | −0.066 | −0.087 | −0.02 | 0.08 |
| −0.12 | 0.2 | 0.240 | −0.064 | −0.062 | −0.095 | −0.03 | 0.15 |
| −0.11 | 0.2 | 0.230 | −0.063 | −0.06 | −0.08 | −0.03 | 0.18 |
| −0.1 | 0.21 | 0.221 | −0.061 | −0.057 | −0.067 | −0.03 | 0.19 |
| −0.09 | 0.22 | 0.211 | −0.060 | −0.048 | −0.088 | −0.02 | 0.25 |
| −0.08 | 0.22 | 0.204 | −0.052 | −0.039 | −0.068 | −0.01 | 0.26 |
| −0.07 | 0.21 | 0.199 | −0.045 | −0.031 | −0.039 | 0.00 | 0.17 |
| −0.07 | 0.21 | 0.195 | −0.044 | −0.027 | −0.034 | 0.01 | 0.10 |
| −0.07 | 0.2 | 0.191 | −0.045 | −0.019 | −0.028 | 0.01 | 0.03 |
| −0.08 | 0.2 | 0.176 | −0.042 | −0.019 | −0.032 | 0.00 | −0.02 |
| −0.06 | 0.19 | 0.170 | −0.037 | −0.015 | −0.01 | 0.00 | −0.01 |
| −0.06 | 0.16 | 0.167 | −0.035 | −0.008 | −0.039 | 0.01 | −0.12 |
| −0.05 | 0.17 | 0.159 | −0.030 | −0.008 | −0.037 | 0.03 | −0.13 |
| −0.05 | 0.10 | 0.158 | −0.032 | −0.01 | −0.068 | 0.01 | −0.21 |
| −0.05 | 0.15 | 0.151 | −0.027 | −0.009 | −0.085 | 0.01 | 0.00 |
| −0.05 | 0.14 | 0.146 | −0.027 | −0.005 | −0.095 | 0.00 | −0.03 |
| −0.05 | 0.13 | 0.137 | −0.019 | −0.01 | −0.069 | 0.01 | 0.03 |
| −0.05 | 0.12 | 0.128 | −0.015 | −0.007 | −0.084 | 0.01 | 0.03 |
| −0.05 | 0.11 | | | −0.012 | −0.034 | | |
| −0.05 | 0.1 | | | −0.012 | −0.036 | | |
| −0.04 | 0.11 | | | | | | |
| −0.04 | 0.09 | | | | | | |
| −0.04 | 0.09 | | | | | | |
| −0.03 | 0.09 | | | | | | |
| −0.03 | 0.09 | | | | | | |
| −0.03 | 0.08 | | | | | | |
| −0.03 | 0.08 | | | | | | |
| −0.03 | 0.08 | | | | | | |
| −0.02 | 0.09 | | | | | | |
| −0.02 | 0.12 | | | | | | |

What is claimed is:

1. A method of detecting and quantifying abnormal tissue in a tissue sample, comprising:

providing a tissue sample;

illuminating the tissue sample with electromagnetic radiation of a first wavelength selected to cause said tissue sample to produce a fluorescence intensity spectrum indicative of a first tissue abnormality property;

detecting a first fluorescence intensity spectrum emitted from said tissue sample as a result of illumination with said first wavelength electromagnetic radiation;

calculating from the first fluorescence intensity spectrum a probability of the tissue sample having the first tissue abnormality property;

illuminating the tissue sample with electromagnetic radiation of a second wavelength selected to cause said tissue sample to produce a fluorescence intensity spectrum indicative of a second tissue abnormality property;

detecting a second fluorescence intensity spectrum emitted from said tissue sample as a result of illumination with said second wavelength electromagnetic radiation;

calculating from the second fluorescence intensity spectrum a probability of the tissue sample having the second tissue abnormality property; and quantifying the tissue sample from the first and second tissue abnormality property probability calculating steps.

2. A method as in claim 1, wherein:

the tissue sample is cervical tissue;

the first wavelength is about 337 nm and the first tissue abnormality property is squamous intraepithelial lesion as distinguished from normal squamous epithelial tissue; and the second wavelength is about 380 nm and the second tissue abnormality property is squamous intraepithelial lesion as distinguished from normal columnar epithelia and inflammation.

3. A method as in claim 1, wherein:

the tissue sample is cervical tissue;

the first wavelength is about 460 nm and the first tissue abnormality property is squamous intraepithelial lesion as distinguished from normal squamous epithelial tissue; and the second wavelength is about 380 nm and the second tissue abnormality property is squamous intraepithelial lesion as distinguished from normal columnar epithelia and inflammation.

4. A method as in claim 1, wherein:

the tissue sample is cervical tissue;

the first wavelength is further selected to cause said tissue sample to produce a fluorescence intensity spectrum indicative of a third tissue abnormality property;

the first wavelength is about 460 nm, the first tissue abnormality property is squamous intraepithelial lesion as distinguished from normal squamous epithelial tissue, and the third tissue abnormality property is high grade squamous intraepithelial lesion as distinguished from low grade squamous intraepithelial lesion; and the second wavelength is about 380 nm and the second tissue abnormality property is squamous intraepithelial lesion as distinguished from normal columnar epithelia and inflammation.

5. A method as in claim 1, further comprising:

illuminating the tissue sample with electromagnetic radiation of a third wavelength selected to cause said tissue sample to produce a fluorescence intensity spectrum indicative of a third tissue abnormality property;

detecting a third fluorescence intensity spectrum emitted from said tissue sample as a result of illumination with said second wavelength electromagnetic radiation; and calculating from the third fluorescence intensity spectrum a probability of the tissue sample having the third tissue abnormality property;

wherein the quantifying step further comprises qualifying the tissue sample from the third tissue abnormality property probability calculating step in addition to the first and second tissue abnormality property probability calculating steps.

6. A method as in claim 5, wherein:

the tissue sample is cervical tissue;

the first wavelength is about 337 nm and the first tissue abnormality property is squamous intraepithelial lesion as distinguished from normal squamous epithelial tissue;

the second wavelength is about 380 nm and the second tissue abnormality property is squamous intraepithelial lesion as distinguished from normal columnar epithelia and inflammation; and the third wavelength is about 460 nm and the third tissue abnormality property is high grade squamous intraepithelial lesion as distinguished from low grade squamous intraepithelial lesion. sample belongs to the particular tissue category.

7. A method of probabilistically classifying a sample of tissue, comprising:

illuminating the tissue sample with electromagnetic radiation having wavelengths of about 337 nm, about 380 nm, and about 460 nm to excite the tissue sample into producing first, second and third fluorescence intensity spectra, respectively;

detecting the first, second and third fluorescence intensity spectra to obtain respective first, second and third spectral data; and calculating a probability that the tissue sample belongs to a first tissue classification from at least one of the first and third spectral data, a probability that the tissue sample belongs to the second tissue classification from the second spectral data, and a probability that the tissue sample belongs to the third tissue classification from the third spectral data.

8. A method as in claim 7, further comprising:

normalizing and mean-scaling the first spectral data prior to the calculating step;

normalizing and mean-scaling the second spectral data prior to the calculating step; and normalizing the third spectral data prior to the calculating step.

9. A method of probabilistically classifying a sample of tissue, comprising:

illuminating the tissue sample with electromagnetic radiation having wavelengths of about 380 nm and about 460 nm to excite the tissue sample into producing first, second and third fluorescence intensity spectra, respectively;

detecting the first and second fluorescence intensity spectra to obtain respective first and second spectral data; and calculating a probability that the tissue sample belongs to a first tissue classification from the second spectral data, a probability that the tissue sample belongs to the second tissue classification from the first spectral data, and a probability that the tissue sample belongs to the third tissue classification from the second spectral data.

10. A method as in claim 9, further comprising:

normalizing the second spectral data prior to the calculating step;

normalizing and mean-scaling the first spectral data prior to the calculating step; and mean-scaling the normalized second spectral data prior to the calculating step.

11. A method of developing an index for calculating a probability that a tissue belongs to one of a plurality of histo-pathologic tissue classifications, comprising:

providing a plurality of tissue samples;

illuminating the tissue samples with electromagnetic radiation having wavelengths of about 337 nm, about 380 nm, and about 460 nm to excite the tissue samples into producing fluorescence intensity spectra;

detecting the fluorescence intensity spectra to obtain first, second and third spectral data from the tissue samples illuminated at respectively the wavelengths of about 337 nm, about 380 nm and about 460 nm in the illuminating step; and forming a first set of principle components from the first spectral data that account for a significant amount of variation in the first spectral data and show statistically significant differences between first and second histo-pathologic tissue classifications;

calculating first probability distribution functions for the first and second histo-pathologic tissue classifications;

forming a second set of principle components from the second spectral data that account for a significant amount of variation in the second spectral data and show statistically significant differences between third and fourth histo-pathologic tissue classifications;

calculating second probability distribution functions for the third and fourth histo-pathologic tissue classifications;

forming a third set of principle components from the third spectral data that account for a significant amount of variation in the third spectral data and show statistically significant differences between fifth and sixth histo-pathologic tissue classifications;

calculating third probability distribution functions for the fifth and sixth histo-pathologic tissue classifications.

12. A method of assigning a probability that a tissue sample belongs to a particular tissue category, comprising:

providing a tissue sample;

illuminating the tissue sample with electromagnetic radiation having wavelengths of about 337 nm, about 380 nm, and about 460 nm to excite the tissue sample into producing fluorescence intensity spectra;

detecting the fluorescence intensity spectra to obtain spectral data; obtaining principal components PC1, PC2, PC4, PC5, and PC7 from said spectral data, and calculating from principal components PC1 and PC2 from spectral data at about 337 nm a probability of squamous intraepithelial lesion as distinguished from normal squamous epithelial tissue, from principal components PC2 and PC5 from spectral data at about 380 rn a probability of squamous intraepithelial lesion as distinguished from normal columnar epithelia and inflammation, and from principal components PC4 and PC7 from spectral data at about 460 nm a probability of high grade squamous intraepithelial lesion as distinguished from low grade squamous intraepithelial lesion.

13. A method of assigning a probability that a tissue sample belongs to a particular tissue category, comprising:

providing a tissue sample;

illuminating the tissue sample with electromagnetic radiation having wavelengths of about 380 nm and about 460 nm to excite the tissue sample into producing fluorescence intensity spectra;

detecting the fluorescence intensity spectra to obtain spectral data;

obtaining principal components PC1, PC2, PC4, PC5, and PC7 from said spectral data; and calculating from principal components PC1 and PC2 from spectral data at about 460 nm a probability of squamous intraepithelial lesion as distinguished from normal squamous epithelial tissue, from principal components PC2 and PC5 from spectral data at about 380 nm a probability of squamous intraepithelial lesion as distinguished from normal columnar epithelia and inflammation, and from principal components PC4 and PC7 from spectral data at about 460 nm a probability of high grade squamous intraepithelial lesion as distinguished from low grade squamous intraepithelial lesion.

14. A method of detecting abnormal epithelial tissue in or from an anatomical feature of a mammal, comprising:

identifying a plurality of individuals having the anatomical feature from a population of interest, the respective anatomical features of the individuals collectively having a diversity of epithelial tissue categories, including normal and abnormal epithelial tissue categories, that is representative of the diversity of the epithelial tissue categories collectively occurring in the respective anatomical features of the population of interest;

optically applying electromagnetic energy comprising a first and second wavelengh to plural epithelial tissue regions of the respective anatomical features of the individuals, said first and second wavelengths selected to produce spectra indicative of a first and second tissue abnormality property, respectively;

optically detecting spectra from the epithelial tissue regions of the respective anatomical features of the individuals resulting from the step of optically applying electromagnetic energy to plural epithelial tissue regions;

processing the optically detected spectra into first spectral data;

transforming the first spectral data into a dimensionally reduced set of variables that significantly accounts for variance in the first spectral data and that exhibits statistically significant differences between the epithelial tissue categories;

optically applying electromagnetic energy comprising said first and second wavelength to epithelial tissue of the anatomical feature of a subject individual, said first and second wavelengths selected to produce spectra indicative of said first and second tissue abnormality properties, respectively;

optically detecting a spectrum from the epithelial tissue of the anatomical feature of the subject individual resulting from the step of optically applying electromagnetic energy to epithelial tissue;

processing the optically detected spectrum into second spectral data; and calculating the probability that the epithelial tissue of the anatomical feature of the subject individual belongs to each of one or more of the epithelial tissue categories from the second spectral data and the dimensionally reduced set.

15. A method as in claim 14, wherein:

each of the epithelial tissue categories has a prior probability of occurring in the individuals;

the first spectral data transforming step comprises calculating principal components and principle component scores; and the probability calculating step comprises classifying the epithelial tissue of the anatomical feature of the subject individual in the tissue category for which a posterior probability is highest, the posterior probability being calculated from the prior probability, the second spectral data, the principal components, and the principal component scores.

16. A method as in claim 15, further comprising:

preprocessing the first spectral data prior to the first spectral data transforming step to remove intra-patient and inter-patient variation; and preprocessing the second spectral data prior to the probability calculating step to remove intra-patient variation.

17. A method as in claim 14, wherein the optically detected spectra and the optically detected spectrum comprise fluorescence spectra.

18. A method as in claim 17, wherein:

the anatomical feature is a human cervix;

the epithelial tissue categories are squamous intraepithelial lesion and normal squamous epithelial tissue; and the electromagnetic energy comprises a wavelength of about 337 nm.

19. A method as in claim 18, further comprising the step of normalizing and mean-scaling the first spectral data prior to the transforming step.

20. A method as in claim 17, wherein:

the anatomical feature is a human cervix;

the epithelial tissue categories are squamous intraepithelial lesion and normal columnar epithelia and inflammation; and the electromagnetic energy comprises a wavelength of about 380 nm.

21. A method as in claim 20, further comprising the step of normalizing and mean-scaling the first spectral data prior to the transforming step.

22. A method as in claim 17, wherein:

the anatomical feature is a human cervix;

the epithelial tissue categories are squamous intraepithelial lesion and normal squamous epithelial tissue; and the electromagnetic energy comprises a wavelength of about 460 nm.

23. A method as in claim 22, further comprising the step of normalizing and mean-scaling the first spectral data prior to the transforming step.

24. A method as in claim 17, wherein:

the anatomical feature is a human cervix;

the epithelial tissue categories are high grade squamous intraepithelial lesion and low grade squamous intraepithelial lesion; and the electromagnetic energy comprises a wavelength of about 460 nm.

25. A method as in claim 24, further comprising the step of normalizing the first spectral data prior to the transforming step.

26. A method as in claim 17, wherein:

the anatomical feature is a human cervix;

the epithelial tissue categories are high grade squamous intraepithelial lesion, low grade squamous intraepithelial lesion, squamous intraepithelial lesion, normal squamous epithelial tissue, normal columnar epithelia, and inflammation; and the electromagnetic energy comprises wavelengths of about 337 nm, 380nm, and 460 nm.

27. A method of identifying a probable tissue category for epithelial tissue of a mammalian patient from among a plurality of epithelial tissue categories, comprising:

identifying the patient with a predetermined population having prior probabilities of the tissue categories therein;

applying electromagnetic radiation comprising a first and second wavelength to a plurality of tissue sites of subjects in the population and to the tissue of the patient, the first and second wavelengths selected to excite respectively a first autofluorescence intensity spectra indicative of first and second tissue categories and second autofluorescence intensity spectra indicative of third and fourth tissue categories;

obtaining first and second sets of subject autofluorescence spectral data from the first and second autofluorescence intensity spectra from the electromagnetic radiation applying step;

preprocessing the first and second sets of subject autofluorescence spectral data to reduce inter-subject and intra-subject variation therein;

forming a first dimensionally reduced set of emission variables from the preprocessed set of first subject autofluorescence spectral data, including a first reduced eigenvector matrix, that shows statistically significant differences between the first and second tissue categories and that significantly accounts for variation in the preprocessed set of first subject autofluorescence spectral data;

calculating first subject scores from the first dimensionally reduced set of emission variables for the first and second tissue categories;

forming a second dimensionally reduced set of emission variables from the preprocessed set of second subject autofluorescence spectral data, including a second reduced eigenvector matrix, that shows statistically significant differences between the third and fourth tissue categories and that significantly accounts for variation in the preprocessed set of second subject autofluorescence spectral data, calculating second subject scores from the second dimensionally reduced set of emission variables for the third and fourth tissue categories;

obtaining respective sets of patient autofluorescence spectral data from the electromagnetic radiation applying step;

preprocessing the sets of patient autofluorescence spectral data to reduce intra-patient variation therein;

concatenating the preprocessed patient autofluorescence spectral data into vectors;

processing the vectors with the first reduced eigenvector matrix to obtain first patient scores;

calculating posterior probabilities for the first and second tissue categories from the first subject scores, from the first patient scores, and from prior probabilities of the first and second tissue categories;

processing the vectors with the second reduced eigenvector matrix to obtain second patient scores; and calculating posterior probabilities for the third and fourth tissue categories from the second subject scores, from the second patient scores, and from prior probabilities of the third and fourth tissue categories.

28. A method as in claim 27, wherein the step of forming a first dimensionally reduced set of emission variables comprises:

forming first principal components and first principle component scores from the preprocessed set of first subject autofluorescence spectral data;

retaining first eigenvalues from the principal components forming step that account for a significant amount of the variation in the preprocessed set of first subject autofluorescence spectral data;

calculating the diagnostic contribution of each of the first principle components for the first retained eigenvalues; and retaining the eigenvalues corresponding to the first principle components identified in the diagnostic contribution calculating step as having a significant diagnostic contribution;

and wherein the step of forming a second dimensionally reduced set of emission variables comprises:

forming second principal components and second principle component scores from the preprocessed set of second subject autofluorescence spectral data;

retaining second eigenvalues from the principal components forming step that account for a significant amount of the variation in the preprocessed set of second subject autofluorescence spectral data;

calculating the diagnostic contribution of each of the second principle components for the second retained eigenvalues; and retaining the eigenvalues corresponding to the second principle components identified in the diagnostic contribution calculating step as having a significant diagnostic contribution.

29. A method as in claim 28, wherein the posterior probability calculating step comprises calculating posterior probability using logistic discrimination.

30. A method as in claim 29, wherein the diagnostic contribution calculating step comprises calculating the diagnostic contribution using a Student's T-Test.

31. A method of obtaining a probability that an epithelial tissue site of a mammalian patient contains tissue belonging to a particular tissue category, comprising:

identifying a training set of epithelial tissue sites identified with a plurality of individuals, the training set of epithelial tissue sites having tissues belonging to a plurality of tissue categories and occurring with known prior probabilities;

obtaining optical response training data from the epithelial tissue sites in the training set by illuminating said tissue sites with electromagnetic radiation comprising a first wavelength selected to produce first spectra indicative of first and second tissue categories, and a second wavelength selected to produce second spectra indicative of third and fourth tissue categories;

calculating a first dimensionally reduced set of variables from the optical response training data that shows statistically significant differences between the first and second tissue categories and that significantly accounts for variation in the first spectra;

calculating a second dimensionally reduced set of variables from the optical response training data that shows statistically significant differences between the third and fourth tissue categories and that significantly accounts for variation in the preprocessed optical response training data;

obtaining optical response patient data from the epithelial tissue site of the patient; and calculating the probability that the epithelial tissue site of the patient contains the particular tissue type using the optical response patient data, the prior probabilities, and the first and second dimensionally reduced set.

32. A method as in claim 31, wherein:

the first dimensionally reduced set calculating step comprises transforming the first spectra into first principal components that significantly accounts for variation in the first spectra, and testing the first principal components for statistically significant differences between the first and second tissue categories using a Student's T-Test;

the second dimensionally reduced set calculating step comprises transforming the second spectra into second principal components that significantly accounts for variation in the second spectra, and testing the second principal components for statistically significant differences between the third and fourth tissue categories using a Student's T-Test; and the probability calculating step comprises logistic discrimination.

33. A method as in claim 32, further comprising the step of preprocessing the optical response training data prior to the first dimensionally reduced set calculating step and the second dimensionally reduced set calculating step to remove inter-individual variations therein.

34. An index embodied on a computer-readable medium for calculating a probability that epithelial tissue in or from an anatomical feature of a mammal belongs to each of a plurality of epithelial tissue categories, the index being formed by the steps of:

identifying a plurality of individuals having the anatomical feature from a population of interest, the respective anatomical features of the individuals collectively having a diversity of the epithelial tissue categories, including normal and abnormal epithelial tissue categories, that is representative of the diversity of the epithelial tissue categories collectively occurring in the respective anatomical features of the population of interest;

optically applying electromagnetic energy comprising a first wavelength and a second wavelength to plural epithelial tissue regions of the respective anatomical features of the individuals, said first and second wavelengths selected to produce first fluorescence intensity spectra indicative of a first tissue abnormality and second fluorescence intensity spectra indicative of a second tissue abnormality, respectively;

optically detecting the first and second fluorescence intensity spectra from the epithelial tissue regions of the respective anatomical features of the individuals resulting from the step of optically applying electromagnetic energy;

processing the first and second fluorescence intensity spectra into first and second spectral data;

transforming the first spectral data into a first dimensionally reduced set of variables that significantly accounts for variance in the first spectral data and that exhibits statistically significant differences between the first tissue abnormality and at least one of the other epithelial tissue categories;

transforming the second spectral data into a second dimensionally reduced set of variables that significantly accounts for variance in the second spectral data and that exhibits statistically significant differences between the second tissue abnormality and at least one of the other epithelial tissue categories; and deriving the index from the first and second dimensionally reduced sets.

35. An index as in claim 34 wherein the first and second spectral data transforming step comprises calculating principal components and principle component scores.

36. An index as in claim 35, further comprising preprocessing the first and second spectral data prior to the first and second spectral data transforming steps to remove intra-patient and inter-patient variation.

37. An index as in claim 34, wherein the optically detected spectra comprises fluorescence spectra.

38. An index as in claim 37, wherein:

the anatomical feature is a human cervix;

the epithelial tissue categories are squamous intraepithelial lesion and normal squamous epithelial tissue; and the electromagnetic energy comprises a wavelength of about 337 nm.

39. An index as in claim 38, further comprising the step of normalizing and mean-scaling the first spectral data prior to the transforming step.

40. An index as in claim 37, wherein:

the anatomical feature is a human cervix;

the epithelial tissue categories are squamous intraepithelial lesion and normal columnar epithelia and inflammation; and the electromagnetic energy comprises a wavelength of about 380 nm.

41. An index as in claim 40, further comprising the step of normalizing and mean-scaling the first spectral data prior to the transforming step.

42. An index as in claim 37, wherein:

the anatomical feature is a human cervix;

the epithelial tissue categories are squamous intraepithelial lesion and normal squamous epithelial tissue; and the electromagnetic energy comprises a wavelength of about 460 nm.

43. An index as in claim 42, further comprising the step of normalizing and mean-scaling the first spectral data prior to the transforming step.

44. An index as in claim 37, wherein:

the anatomical feature is a human cervix;

the epithelial tissue categories are high grade squamous intraepithelial lesion and low grade squamous intraepithelial lesion; and the electromagnetic energy comprises a wavelength of about 460 nM.

45. An index as in claim 44, further comprising the step of normalizing the first spectral data prior to the transforming step.

46. An index as in claim 37, wherein:

the anatomical feature is a human cervix;

the epithelial tissue categories are high grade squamous intraepithelial lesion, low grade squamous intraepithelial lesion, squamous intraepithelial lesion, normal squamous epithelial tissue, normal columnar epithelia, and inflammation; and the electromagnetic energy comprises wavelengths of about 337 nm, 380nm, and 460 nm.

* * * * *

UNITED STATES PATENT AND TRADEMARK OFFICE
CERTIFICATE OF CORRECTION

PATENT NO. : 6,095,982
DATED : August 1, 2000
INVENTOR(S) : Richards-Kortum et al.

It is certified that error appears in the above-identified patent and that said Letters Patent is hereby corrected as shown below:

In claim 5, column 26, line 65, after 'property;' insert -- and -- therefor.

In claim 6, column 27, lines 18 - 19, after 'lesion.' please delete "sample belongs to the particular tissue category."

In claim 11, column 28, line 14, after 'step;' delete "and" therefor.

In claim 11, column 28, line 34, after 'classifications;' insert "and" therefor.

In claim 12, column 28, line 47, delete "spectral data, and" and insert --spectral data; and -- therefor.

In claim 12, column 28, line 53, delete "380 rn" and insert -- 380 nm -- therefor.

In claim 44, column 31, line 41, delete "data," and insert -- data; -- therefor.

In claim 44, column 31, line 51, delete "concatenating" and insert -- combining -- therefor.

Signed and Sealed this

Twenty-fourth Day of April, 2001

NICHOLAS P. GODICI

Attest:

Attesting Officer

Acting Director of the United States Patent and Trademark Office